US009023067B2

(12) United States Patent
Ohdaira

(10) Patent No.: US 9,023,067 B2
(45) Date of Patent: May 5, 2015

(54) SURGICAL SYSTEM FOR STOMA CLOSURE IN BIOLOGICAL DUCT

(75) Inventor: Takeshi Ohdaira, Shimotsuke (JP)

(73) Assignee: Educational Foundation Jichi Medical University, Shimotsuke-Shi Tochigi (JP)

( * ) Notice: Subject to any disclaimer, the term of this patent is extended or adjusted under 35 U.S.C. 154(b) by 637 days.

(21) Appl. No.: 13/381,436

(22) PCT Filed: Jul. 12, 2010

(86) PCT No.: PCT/JP2010/061798
§ 371 (c)(1),
(2), (4) Date: Apr. 9, 2012

(87) PCT Pub. No.: WO2011/004905
PCT Pub. Date: Jan. 13, 2011

(65) Prior Publication Data
US 2012/0190917 A1    Jul. 26, 2012

(30) Foreign Application Priority Data

Jul. 10, 2009 (JP) ................................ 2009-164056

(51) Int. Cl.
*A61B 17/04* (2006.01)
*A61B 17/068* (2006.01)
*A61B 17/00* (2006.01)
*A61B 17/064* (2006.01)

(52) U.S. Cl.
CPC ......... *A61B 17/0401* (2013.01); *A61B 17/0469* (2013.01); *A61B 17/0482* (2013.01); *A61B 17/0487* (2013.01); *A61B 17/068* (2013.01); *A61B 2017/00544* (2013.01); *A61B 2017/0409* (2013.01); *A61B 2017/0414* (2013.01); *A61B 2017/0417* (2013.01); *A61B 2017/0427* (2013.01); *A61B 2017/0464* (2013.01); *A61B 2017/047* (2013.01); *A61B 2017/0472* (2013.01); *A61B 2017/0496* (2013.01); *A61B 2017/0647* (2013.01)

(58) Field of Classification Search
CPC ............ A61B 2017/00535; A61B 2017/00544
USPC ..................... 606/139–150; 227/175.1, 176.1
See application file for complete search history.

(56) References Cited

U.S. PATENT DOCUMENTS

| | | | | |
|---|---|---|---|---|
| 2,611,366 A | * | 9/1952 | Mull | 606/146 |
| 4,422,567 A | * | 12/1983 | Haynes | 227/19 |
| 4,437,465 A | * | 3/1984 | Nomoto et al. | 606/144 |
| 4,586,502 A | * | 5/1986 | Bedi et al. | 606/144 |

(Continued)

*Primary Examiner* — Katherine Dowe
*Assistant Examiner* — Amy Shipley
(74) *Attorney, Agent, or Firm* — Greer, Burns & Crain, Ltd.

(57) ABSTRACT

A surgical system for small-pit closure in hollow organs is provided. The surgical system is provided with a surgical device for small-pit closure in hollow organs, with the surgical device including the following components: a suture-member cartridge in which a pair of parallel tubular members that accommodate respective suture members are feedably connected to the rear ends of a pair of arrow-shaped members that latch into tissue in a hollow organ; an auxiliary shooting unit having plungers respectively provided in a pair of cylinders open at both ends; a hollow-organ-insertable unit configured of a pair of flexible air tubes; and a gas shooter that sequentially discharges compressed air or high-pressure gas into the open-ended cylinders in response to operations of a trigger, for sequentially ejecting the arrow-shaped members and driving the same into tissue in the hollow organ on both sides of a small pit site.

27 Claims, 27 Drawing Sheets

(56) References Cited

U.S. PATENT DOCUMENTS

| | | | |
|---|---|---|---|
| 5,306,281 A * | 4/1994 | Beurrier | 606/144 |
| 5,308,353 A * | 5/1994 | Beurrier | 606/144 |
| 5,520,700 A * | 5/1996 | Beyar et al. | 606/139 |
| 5,797,960 A | 8/1998 | Stevens et al. | |
| 5,810,848 A | 9/1998 | Hayhurst | |
| 6,231,561 B1 | 5/2001 | Frazier et al. | |
| 6,626,930 B1 | 9/2003 | Allen et al. | |
| 7,473,258 B2 * | 1/2009 | Clauson et al. | 606/139 |
| 7,608,092 B1 * | 10/2009 | Schaffhausen | 606/232 |
| 8,449,530 B2 * | 5/2013 | Bacher et al. | 606/1 |
| 8,469,977 B2 * | 6/2013 | Balbierz et al. | 606/153 |
| 8,585,581 B2 * | 11/2013 | Narthasilpa et al. | 600/37 |
| 2004/0093023 A1 | 5/2004 | Allen et al. | |
| 2004/0138683 A1 | 7/2004 | Shelton et al. | |
| 2004/0249395 A1 * | 12/2004 | Mikkaichi et al. | 606/144 |
| 2005/0177180 A1 | 8/2005 | Kaganov et al. | |
| 2006/0064115 A1 | 3/2006 | Allen et al. | |
| 2006/0064116 A1 | 3/2006 | Allen et al. | |
| 2009/0088780 A1 | 4/2009 | Shiono et al. | |
| 2010/0114122 A1 * | 5/2010 | Dubrovsky | 606/147 |
| 2010/0292710 A1 * | 11/2010 | Daniel et al. | 606/142 |
| 2010/0292713 A1 * | 11/2010 | Cohn et al. | 606/143 |
| 2011/0092988 A1 * | 4/2011 | Cohen et al. | 606/142 |
| 2014/0276986 A1 * | 9/2014 | Hoarau et al. | 606/144 |

\* cited by examiner (a)

(b)

(a)

(b)

(c)

(a)

(b)

(a)

(b)

(a)

(b)

(a)

(b)

(a)

(b)

SURGICAL SYSTEM FOR STOMA CLOSURE IN BIOLOGICAL DUCT

TECHNICAL FIELD

The present invention relates to a surgical technique for suturing small pits (or holes) in hollow organs, including perforations at the site of a lesion and accidental piercings during treatment, and particularly to a surgical system for small-pit closure in hollow organs that reduces the invasiveness of a surgical procedure by using an endoscope or a capsule endoscope to suture the small pit and that eliminates the need for conventional major surgical procedures such as abdominal incisions.

BACKGROUND ART

In most cases when surgery has been performed on a patient to suture tissue around a small pit in a digestive tract or other hollow organ, including perforations in lesions caused by cancer or the like, accidental piercings (punctures and other surgical wounds) occurring during treatment, and perforations formed for performing endoscopic gall-bladder surgery through the patient's stomach, the surgery has conventionally involved major procedures such as abdominal incisions. Recently, however, less-invasive surgical methods involving transoral or transanal endoscopic procedures have been proposed, and practical applications of these methods are currently being researched and developed.

In the following description, the portion of a device or hollow organ that is the farthest inside the patient's body from a natural orifice, such as the mouth or anus, will be referred to as the "leading (or forward) end" or "front part" or "far end," while the portion of the device or duct closest to the outside of the body will be referred to as the "rear end" or "rear part" or "near end."

One example of a conventional transoral or transanal endoscopic instrument for small-pit closure in hollow organs is the suturing device 301 shown in FIGS. 30 through 33. The suturing device 301 sutures tissue by using a suture unit 333 that includes a suture thread 334, to whose respective ends are attached a first anchor 336 and a second anchor 337. The suturing device 301 also includes: a hollow tip (needle) 304 that houses the anchors 336 and 337; a wire 305 that has a front end that is inserted into the tip 304 for ejecting the first and second anchors 336 and 337 out of the tip 304; a flexible tube 307 that has a leading end integrally connected to the rear end of the tip 304 and through which the wire 305 is inserted and is capable of advancing and retracting in the axial direction of the flexible tube 307; a second sheath 306 that is inserted into the flexible tube 307 and is capable of advancing and retracting in the axial direction together with the wire 305; an abutting member 310 mounted on the wire 305 for maintaining a fixed relative positional relationship between the wire 305 and second sheath 306; a connecting tube 311 provided on the flexible tube 307 or the tip 304 for restricting the forward movement of the second sheath 306; and an operating part 303 provided on the rear end of the wire 305 and second sheath 306 for operating the wire 305 and second sheath 306. When the wire 305 is moved forward while the abutting member 310 holds the relative positions of the wire 305 and second sheath 306 constant, the wire 305 ejects only the first anchor 336 out of the tip 304 after the connecting tube 311 restricts the forward movement of the second sheath 306 (refer to FIGS. 1-11 in Patent Document 1, for example).

A laparoscopic surgical instrument for small-pit closure can also be readily applied when using transoral or transanal endoscopy in small-pit closure surgery of hollow organs. A typical laparoscopic suture/closure instrument includes a cannula 412 that includes: a connecting rod 420 that has an actuating mechanism for advancing or retracting in the axial direction of the cannula 412; a needle-suture complex 422 that is attached to the far end of the connecting rod 420 and that has a pair of needles 426a and 426b that, in an operative configuration, extend outward from the far end of the cannula 412 in opposite directions to each other to positions beyond the periphery of the perforated site, and a suture thread 428 that extends between the pair of needles; and a needle-trap mechanism 432 for engaging and locking with the needles 426a and 426b deployed in the operative configuration. A needle-trap mechanism 432 operates to draw needles 426a and 426b into the cannula 412, drawing the suture thread 428 that extends between the needles 426a and 426b from the perforated site and forming a closure in the perforated site (refer to FIGS. 1-8 of Patent Document 2, for example).

PRIOR ART DOCUMENTS

Patent Document 1: Japanese Unexamined Patent Application Publication No. 2009-82716
Patent Document 2: Japanese Unexamined Patent Application (Translation of PCT Application) Publication No. 2005-518862

SUMMARY OF THE INVENTION

Problems to be Solved by the Invention

The conventional suturing device 301 described in Patent Document 1 performs the following procedure in surgery to stitch a small pit or the like that has been formed, for example, in the stomach wall or other digestive tract.

First, the operator moves the leading end of an endoscope (not shown in the drawings), which has been inserted into the digestive tract of the patient, to near the tissue having the small pit or another target of the procedure. The operator then inserts the leading end of the suturing device 301 into the forceps mouth of the endoscope until the leading-end 302 of the suturing device 301 is exposed on the outside of the endoscope channel.

Next, the operator slides the slider 318 forward until the tip 304 and the suture unit 333 that is affixed to the tip 304 are exposed from the leading end of the first sheath 308, as shown in FIGS. 31(a) and 31(b). At this time, the operator adjusts the fixing position of an adjuster 316 in the forceps mouth relative to the main body 312 so that the slider 318 contacts the adjuster 316, thereby adjusting the extent to which the tip 304 protrudes from the first sheath 308.

Next, with the tip 304 protruding from the first sheath 308, the operator moves the leading end of the suturing device 301 near a target tissue T around a perforation or the like and inserts the tip 304 obliquely through the tissue T1 on one side of the perforation, as shown in FIG. 32. The operator then pushes the sheath-operating member 322 of the tip operating part 314 forward so that the second sheath 306 slides forward. Because the leading end 306a of the second sheath 306 contacts the abutting member 310 of the wire 305 at this time, the wire 305 that is pressed by the second sheath 306 moves forward together with the first sheath 308 while their relative positions remain constant. The operator continues to push the sheath-operating member 322 until the leading end 306a of the second sheath 306 contacts the rear end 311b of the connecting tube 311, which contact restricts the further forward movement of the second sheath 306. Subsequently, the pressing member 309 that is disposed on the leading end of the wire 305 pushes the first and second anchors 336 and 337 forward so that the suture unit 333 and first anchor 336 are ejected from the suture thread 334. The operator can confirm that the first anchor 336 has been ejected by the feel of the second sheath 306 contacting the connecting tube 311.

Next, the operator pulls the tip 304 out from the tissue T1. At this time, the first anchor 336 remains anchored in the tissue T1.

In a similar manner, the operator then inserts the tip 304 into the tissue T2 on the opposite side of the perforation from the tissue T1. After the tip 304 has penetrated the tissue T2, the operator removes the wire stopper 324 and operates the wire-operating knob 323 so as to push the wire 305 forward. As the wire 305 advances forward, the second anchor 337 is ejected from the tip 304, after which the operator pulls the tip 304 from the tissue T2 while leaving the second anchor 337 anchored in the tissue T2, as shown in FIG. 33.

With the suturing device 301 in this state, the operator pulls the slider 318 toward the rear end 312a of the main body 312 (see FIG. 31(a)) until the flexible tube 307 and tip 304 are drawn into the first sheath 308. Because the tip operating part 314 is retracted together with the slider 318 at this time, the wire 305 is also retracted, and the suture thread 334 of the suture unit 333 that is tied to the wire 305 is drawn into the first sheath 308 until the stopper 335 on the suture thread 334 contacts the leading end of the first sheath 308. As the operator continues to draw back the slider 318, only the suture thread 334 is drawn into the second sheath 306, while the stopper 335 remains in contact with the second sheath 306, shortening the distance between the stopper 335 and the anchors 336 and 337.

Because the anchors 336 and 337 are anchored in the respective tissues T1 and T2, the tissues T1 and T2 are pulled toward the suturing device 301 along with the anchors 336 and 337 as the stopper 335 nears the anchors 336 and 337. A suture in the target tissue T is completed when the tissues T1 and T2 contact each other.

As the suture thread 334 moves toward the midpoint 334a and is received in the first sheath 308, the engagement between the end portions 335a and 335b of the stopper 335 loosens. If the operator attempts to move the suture thread 334 toward the anchors 336 and 337, the end portions 335a and 335b become more firmly engaged to each other by the force applied to the suture thread 334, preventing the suture thread 334 from moving in that direction. In other words, because the stopper 335 can move only toward the anchors 336 and 337 and not in the opposite direction, the suture formed in the target tissue T remains intact.

Once the suture is formed, the operator pulls the wire-operating knob 323 so as to retract the wire 305 within the flexible tube 307. When the leading end of the wire 305 has moved farther rearward than the connecting tube 311, the suture thread 334 comes free from the wire 305, separating the suture unit 333 from the suturing device 301. This completes the suturing procedure.

However, the conventional suturing device 301 described above has several problems, including requiring that the operator (1) perform delicate and complex manual operations outside the endoscope in order to sequentially eject the anchors 336 and 337, and (2) engage the anchors 336 and 337 in the tissues T1 and T2, respectively, by obliquely penetrating the tissues T1 and T2 at suitable positions on the inside of the small pit. Consequently, the suturing device 301 is limited to tiny pits and requires that the operator have considerable skill to perform surgery using the suturing device 301.

Next, a surgical procedure using the suture/closure instrument disclosed in Patent Document 2 for suturing a laparoscopic port or puncture, for example, will be described.

As shown in FIG. 34, a needle-suture complex 422 is inserted through a port and deployed below the layers of skin 436, subcutaneous fat 438, fascia 440, and peritoneum (serous membrane) 442 through which the port is formed.

Once the operator has extended the needle-suture complex 422 through the far end 412a of the cannula 412, the needle-suture complex 422 shifts from its first folded configuration to a second operative configuration not shown in the drawings. When the needle-suture complex 422 is in its operative configuration, needle-holder arms 424a and 424b are pivoted outward so that the needles 426a and 426b held thereby are spread apart, extending to positions outside the opening formed in the far end 412a of the cannula 412. Here, the needle-holder arms 424a and 424b are outwardly biased through the use of springs or another biasing force. Both the needle-holder arms 424a and 424b and the needles 426a and 426b are bent inward and arranged so that the needles 426a and 426b are substantially perpendicular relative to the serous membrane 442 and fascia 440 while the suture/closure instrument is held in a prescribed orientation that is generally parallel to the cannula 412. The needle-holder arms 424a and 424b and the needles 426a and 426b are further configured to extend outward in diametrically opposed directions from the far end 412a of the cannula 412 and from the periphery of the port opening by a distance (preferably at least 1 cm) sufficient for drawing peripheral tissue together to form a secure closure.

FIG. 36 illustrates the process by which the suture thread 428 deployed by the needle-suture complex 422 becomes positioned across the puncture site. The needles 426a and 426b, which extend upward on opposing sides of the puncture, are inserted at a generally perpendicular orientation into the serous membrane 442 and fascia 440 and traverse the serous membrane 442, fascia 440, and subcutaneous fat 438 before being received in the lumen of the cannula 412. Hence, the paths of penetration defined by the opposing needles 426a and 426b achieve a substantially secure suture. In order to improve the performance of the suture/closure instrument in closing the perforation through deployment of the suture thread 428, a tapered mount 430 is formed in the lower part of the needle-suture complex 422, enabling the surrounding tissue to be radially contracted more easily.

Next, the mechanism for safely and atraumatically withdrawing the needles 426a and 426b after the suture thread 428 has been deployed around the puncture site will be described. The needle-suture complex 422 also has a third retraction configuration, whereby the needles 426a and 426b are received in the needle-trap mechanism 432 and ultimately detach from the respective needle-holder arms 424a and 424b, to be retained in the cannula 412 of the suture/closure instrument. Specifically, when the connecting rod 420 is pressed downward, a force is applied to the needle-holder arms 424a and 424b, causing those needle-holder arms to rotate inward. Consequently, the opposing needles 426a and 426b also rotate so that their tips close inwardly. The tips of the needles 426a and 426b are received in a capture area 434 formed at the far end of the needle-trap mechanism 432, which extends axially around the connecting rod 420 (see FIG. 35). After the tips of the needles 426a and 426b are captured in the needle-trap mechanism 432, the needle-trap mechanism 432, together with the needles 426a and 426b, is pulled upward through the cannula 412 by the actuation of a lever (not shown) extending outward from the near end of the cannula 412. Consequently, the needles 426a and 426b detach from the needle-holder arms 424a and 424b, separate from the needle-suture complex 422, and are ultimately retained within the lumen of the cannula 412.

The needles 426a and 426b are detached from the needle-holder arms 424a and 424b, with the ends of the suture thread 428 still attached to said needles, and then travel upward through the cannula 412. The suture thread 428, having been stitched across opposing sides of the puncture site, extends across the puncture site, then upward through piercings formed by the respective needles 426a and 426b in the peritoneum 442, fascia 440, and subcutaneous fat 438, and finally through the previously formed port channel. The suture thread 428 is then pulled out from the body by simply withdrawing the entire suture/closure instrument out of the patient.

As shown in FIG. 36, the suture thread 428 ultimately traverses the puncture (small pit) site, with the respective ends of the suture thread 428 extending out of the body from the periphery of the puncture site so as to form a suture, whereby the puncture site is closed.

However, the suture/closure instrument disclosed in Patent Document 2 has several problems, including (1) the complex structure of the needle-suture complex 422, whose pair of opposing needles 426a and 426b have a bent shape, requiring the operator to perform delicate operations manually on the outside of the endoscope, and (2) the need to pass the needle-suture complex 422 through the puncture before stitching the site with the suture thread 428 via the needles 426a and 426b. Consequently, due to the space requirements of the device, this suture/closure instrument is not suitable for a tiny pit smaller than a few millimeters in size, and the operator must have considerable skill to perform surgery using this device.

Further, both of the conventional suturing devices disclosed in Patent Documents 1 and 2 insert the tip 304 or needles 426a and 426b into the tissue on both sides of the small pit, penetrating the tissue. Hence, a fundamental problem of these devices is their high potential to cause damage to the intricate blood vessel groups present in the submucosa of the stomach, for example, as well as to nearby internal organs and the like.

In view of the foregoing problems of the conventional technologies, one objective of the present invention is to provide a surgical system for small-pit closure in hollow organs that (1) can reduce the duration and invasiveness of operations by eliminating the need for such major surgical procedures as abdominal incisions; (2) is excellent in operability, reliability, and safety; and (3) is applicable to patients having unusual conditions, such as a tendency to hemorrhage, myocardial infarction, cerebral infarction, or cirrhosis, and to patients having prosthetic valves.

Means for Solving the Problems

The above aims will be achieved by the present invention's surgical system for small-pit closure in hollow organs, with said surgical system, as described in Claim 1, having a surgical device for small-pit closure in hollow organs with said surgical device being a suturing device formed so as to be freely insertable through an operating channel of an endoscope inserted into a hollow organ so as to suture, through the operating channel, tissue at the site of a small pit in the hollow organ by using a suture member that includes (a) at least one pair of first and second arrowy-shaped members having engaging parts that engage with tissue in the hollow organ, and (b) a suture thread that is attached by one of its ends (first end) to the rear end of the first arrowy-shaped member and that is inserted into and pulled freely through the rear end of the second arrowy-shaped member, with said surgical device including: (1) a suture-member cartridge constituting the leading-end portion of the surgical device and having at least one pair of tubes arranged parallel to each other, whereby the suture thread is diverted around leading ends of the tubes or passed through small holes or slit-like openings provided in opposing side walls of the tubes and is fixed by the opposite (second) end of the suture thread to the inner surface on the leading end side of the tubular member that accommodates the second arrowy-shaped member, with the arrowy-shaped member linked by the suture thread forming a pair that are respectively accommodated in the tubes; (2) a hollow-organ-insertable unit that includes flexible air tubes that are coupled to the rear end of the suture-member cartridge; and (3) a gas shooter that is coupled to the rear end of the hollow-organ-insertable unit outside the hollow organ and that includes a cylinder unit that has (a) a piston that, through its operation, generates compressed air, and (b) a high-pressure-gas reservoir that stores high-pressure gas, with said compressed air or high-pressure gas being released through an ejection hole in response to trigger operations of the gas shooter and sequentially ejected into the suture-member cartridge via the hollow-organ-insertable unit;

and the arrowy-shaped members are sequentially ejected from the suture-member cartridge by compressed air or high-pressure gas sequentially ejected into the suture-member cartridge and are driven into tissue in the hollow organ on both sides of the small-pit site, with the rear ends of the arrowy-shaped members being drawn together via the suture thread linking those rear ends so as to tightly suture the small-pit site.

The present invention's surgical system, as described in Claim 2, for small-pit closure in hollow organs has a surgical device for small-pit closure in hollow organs, with said surgical device being a suturing device formed to be directly and freely inserted into a hollow organ so as to suture tissue at the site of a small pit in the hollow organ by using a suture member that includes (a) at least one pair of first and second arrowy-shaped members having engaging parts that engage with tissue in the hollow organ, and (b) a suture thread that is attached by one of its ends (first end) to the rear end of the first arrowy-shaped member and that is inserted into and pulled freely through the rear end of the second arrowy-shaped member; with said system also having a capsule endoscope that either is accommodated inside the leading end of the surgical device or is inserted directly into the hollow organ; and with said surgical device including: (1) a suture-member cartridge constituting the leading-end portion of the surgical device and having at least one pair of tubes arranged parallel to each other, whereby the suture thread is diverted around the leading ends of the tubes or passed through small holes or slit-like openings provided in opposing side walls of the tubes and is fixed by the opposite end (second end) of the suture thread to the inner surface of the leading-end side of the tubular member that accommodates the second arrowy-shaped member, with the arrowy-shaped member, which are linked by the suture thread to form a pair, being respectively accommodated in the tubes; (2) a hollow-organ-insertable unit that includes flexible air tubes that are coupled to the rear end of the suture-member cartridge; and (3) a gas shooter that is coupled to the rear end of the hollow-organ-insertable unit outside the hollow organ and that includes a cylinder unit having either (a) a piston that, through its operation, generates compressed air, or (b) a high-pressure-gas reservoir that stores high-pressure gas, with said compressed air or high-pressure gas being released through an ejection hole in response to trigger operations of the gas shooter and sequentially ejected into the suture-member cartridge via the hollow-organ-insertable unit; and the arrowy-shaped members are sequentially ejected from the suture-member cartridge by compressed air or high-pressure gas sequentially ejected into the suture-member cartridge and are driven into tissue in the hollow organ on both sides of a small-pit site, with the rear ends of the arrowy-shaped members being drawn together via the suture thread linking those rear ends so as to tightly suture the small-pit site.

The present invention's surgical system, as described in Claim 3, for small-pit closure in hollow organs has a surgical device for small-pit closure in hollow organs, with said surgical device being a suturing device mounted along the outer surface of an endoscope inserted into a hollow organ and extending to the leading-end portion of the endoscope so as to suture tissue at the site of a small pit in the hollow organ, by using a suture member that includes (a) at least one pair of first and second arrowy-shaped members having engaging parts that engage with tissue in the hollow organ, and (b) a suture thread that is attached by one of its ends (first end) to the rear end of the first arrowy-shaped member and is then inserted into and pulled freely through the rear end of the second arrowy-shaped member, and with said surgical device including:

(1) a suture-member cartridge constituting the leading-end portion of the surgical device and having at least one pair of tubes arranged alongside the outer surface of the leading-end portion of the endoscope, and whereby the suture thread is diverted around the leading ends of the tubes or passed through small holes or slit-like openings provided in opposing side walls of the tubes and is fixed by the opposite end (second end) of the suture thread to the inner surface of the leading-end side of the tubular member that accommodates the second arrowy-shaped member, with the arrowy-shaped members, which are linked by the suture thread to form a pair, being respectively accommodated in the tubes;

(2) a hollow-organ-insertable unit that includes flexible air tubes that are coupled to the rear end of the suture-member cartridge; and (3) a gas shooter that is coupled to the rear end of the hollow-organ-insertable unit outside the hollow organ and that includes a cylinder unit having either (a) a piston that, through its operation, generates compressed air, or (b) a high-pressure-gas reservoir that stores high-pressure gas; with said compressed air or high-pressure gas being released through an ejection hole in response to trigger operations of the gas shooter and sequentially ejected into the suture-member cartridge via the hollow-organ-insertable unit;

and the arrowy-shaped members are sequentially ejected from the suture-member cartridge by compressed air or high-pressure gas sequentially ejected into the suture-member cartridge and are driven into tissue in the hollow organ on both sides of the small-pit site, with the rear ends of the arrowy-shaped members drawn together via the suture thread linking those rear ends, so as to tightly suture the small-pit site.

The present invention's surgical system, as described in Claim 4, for small-pit closure in hollow organs has a surgical device for small-pit closure in hollow organs, with said surgical device being a suturing device mounted along the outer surface of an endoscope inserted into a hollow organ and extending to the leading-end portion of the endoscope so as to suture tissue at the site of a small pit in the hollow organ, by using a suture member that includes (a) multiple pairs of first and second arrowy-shaped members having engaging parts that engage with tissue in the hollow organ, and (b) a suture thread that is attached by one of its ends (first end) to the rear end of the first arrowy-shaped member and then is inserted into and pulled freely through the rear end of the second arrowy-shaped member; with said surgical device including:

(1) multiple pairs of suture-member cartridges constituting the leading-end portion of the surgical device and having multiple pairs of tubes arranged alongside the outer surface of the leading-end portion of the endoscope, whereby the suture thread for each pair of arrowy-shaped members is diverted around the leading ends of the corresponding pair of tubes or passed through small holes or slit-like openings provided in opposing side walls of the tubes and is fixed by the opposite end (second end) of the suture thread to the inner surface of the leading-end side of the tubular member that accommodates the second arrowy-shaped member, with the arrowy-shaped members, which are linked by the suture thread to form a pair, being respectively accommodated in the tubes;

(2) a feed-air switching mechanism coupled to the respective rear ends of the suture-member cartridges, for switching between a circulation state for supplying compressed air or high-pressure gas sequentially into each suture-member cartridge and a non-circulation state for blocking the compressed air or high-pressure gas; (3) a hollow-organ-insertable unit that includes at least one flexible air tube that is coupled to the rear end of the feed-air switching mechanism and is arranged alongside the outer surface of a hollow-organ-insertable tube of the endoscope; and (4) a gas shooter that is coupled to the rear end of the hollow-organ-insertable unit outside the hollow organ, and that includes a cylinder unit that has either (a) a piston that, through its operation, generates compressed air, or (b) a high-pressure-gas reservoir that stores high-pressure gas; with said compressed air or high-pressure gas being released through an ejection hole in response to trigger operations of the gas shooter and sequentially ejected into the suture-member cartridges via the hollow-organ-insertable unit and the feed-air switching mechanism; and the arrowy-shaped members are sequentially ejected from the suture-member cartridge by compressed air or high-pressure gas sequentially ejected into the suture-member cartridge and are driven into tissue in the hollow organ on both sides of the small-pit site, with the rear ends of the arrowy-shaped members drawn together via the suture thread linking those rear ends, so as to tightly suture the small-pit site.

The present invention's surgical system, as described in Claim 5, for small-pit closure in hollow organs has a surgical device for small-pit closure in hollow organs, with said surgical device being a suturing device mounted along the outer surface of an endoscope that is inserted into a hollow organ and that extends to the leading-end portion of the endoscope, so as to suture tissue at the site of a small pit in the hollow organ by using a suture member that includes (a) at least one pair of first and second arrowy-shaped members having engaging parts that engage with tissue in the hollow organ, and (b) a suture thread whose two ends are respectively attached to the rear ends of the arrowy-shaped members, with said surgical device including: (1) at least one pair of suture-member cartridges constituting the leading-end portion of the surgical device and having at least one pair of tubular members and a narrow tube interposed between the pair of tubular members arranged alongside the outer surface of the leading-end portion of the endoscope, whereby the suture thread is diverted around the leading ends of the tubular members or passed through small holes or slit-like openings provided in opposing side walls of the tubular members, with the middle portion of the suture thread inserted as a U-shaped loop through a threading member and accommodated in the narrow tube, with the arrowy-shaped members, which are linked by the suture thread so as to form a pair, respectively accommodated in the tubular members; (2) a hollow-organ-insertable unit that includes flexible air tubes that are coupled to the rear end of the suture-member cartridge; (3) a gas shooter that is coupled to the rear end of the hollow-organ-insertable unit outside the hollow organ and that includes a cylinder unit having either (a) a piston that, through its operation, generates compressed air, or (b) a high-pressure-gas reservoir that stores high-pressure gas, whereby the compressed air or high-pressure gas is released through an ejection hole in response to trigger operations and is sequentially ejected into the suture-member cartridge via the hollow-organ-insertable unit; and (4) pulling means having (a) a flexible guide tube whose leading-end portion can be inserted into the narrow tube, and (b) a wire on the leading end of which is provided an engaging part for engaging the U-shaped middle portion of the suture thread in the narrow tube for pulling the middle portion of the suture thread by the rear-end portion of the wire outside the hollow organ in a direction away from the hollow organ; and the arrowy-shaped members are sequentially ejected from the suture-member cartridge by compressed air or high-pressure gas sequentially ejected into the suture-member cartridge and are driven into tissue in the hollow organ on both sides of the small-pit site, with the rear ends of the arrowy-shaped members drawn together via the suture thread linking those rear ends, so as to tightly suture the small-pit site.

The invention described in Claim 6 is a surgical system for small-pit closure in hollow organs according to Claim 5, wherein the pulling means further includes a wire-take-up means that is coupled to the guide tube on the rear end outside the hollow organ, is fixed to the rear end of the wire, and that, in response to a trigger operation, rotates in the direction for taking up the wire.

The invention described in Claim 7 is a surgical system for small-pit closure in hollow organs according to any of claims 1 through 6, further including an auxiliary shooting unit that has (1) an open-ended cylinder that is coupled and interposed between the suture-member cartridge and the hollow-organ-insertable unit, and (2) a plunger accommodated in the open-ended cylinders that moves freely forward and rearward while maintaining airtight;

and compressed air or high-pressure gas is sequentially ejected into the auxiliary shooting unit via the hollow-organ-insertable unit in response to a trigger operation on the gas shooter, whereby the plungers advance rapidly in sequence and generate secondary compressed air for sequentially ejecting the arrowy-shaped members from the suture-member cartridge and driving the arrowy-shaped members into tissue in the hollow organ on both sides of the small-pit site.

The invention described in Claim 8 is a surgical system for small-pit closure in hollow organs according to any of claims 1 through 3 or 5 through 7, wherein the surgical device for small-pit closure in hollow organs includes multiple pairs of suture-member cartridges, and the air tubes are arranged parallel to each other.

The invention described in Claim 9 is a surgical system for small-pit closure in hollow organs according to any of claims 1 through 3 or 5 through 7, wherein the feed-air switching mechanism that switches between a circulation state for supplying compressed air or high-pressure gas sequentially into each air tube in the hollow-organ-insertable unit and a non-circulation state for blocking the compressed air or high-pressure gas is interposed between the rear end of the hollow-organ-insertable unit 2 on the outside of the hollow organ and the gas shooter.

The invention described in Claim 10 is a surgical system for small-pit closure in hollow organs according to Claim 4 or Claim 9, wherein the feed-air switching mechanism includes: a generally cylindrical hollow case that is interposed between the hollow-organ-insertable unit and the suture-member cartridge or the gas shooter that has front and rear walls coupled to the hollow-organ-insertable unit and the suture-member cartridge or the gas shooter and that is fitted around the leading-end of an endoscope; a rotary member rotatably accommodated in the case and having a switching plate formed adjacent to the front wall of the case; and a driving means for rotating the rotary member in association with a trigger operation on the gas shooter in order to switch sequentially the two positions for the circulation state achieved with an opening provided in the switching plate and the non-circulation state achieved through a shielding part constituting the area of the switching plate other than the opening.

The invention described in Claim 11 is a surgical system for small-pit closure in hollow organs according to Claim 10, wherein the driving means includes the following, all of which are accommodated in the case:

a knock member fitted around the generally cylindrical body of the rotary member while freely moving forward and rearward and having a piston formed on the rear end of the knock member, with pressing teeth in a number (N) equal to the number of suture-member cartridges formed on the front end of the knock member;

protruding parts formed on the outer circumference of the cylindrical body that is connected to a switching plate of the rotary member;

a cam cylinder having N/2 each of both deep first-cam grooves and shallow second-cam grooves formed alternately on the inner surface of said cam cylinder at circumferential intervals (pitch angles) corresponding to the placement of the suture-member cartridges for alternately engaging with the protruding members on the rotary member while being freely movable forward and rearward, and having a front-end face that contacts the inner surface on the front wall of the case; and a compression spring interposed between the cam cylinder and the piston, for constantly urging the piston toward the back side of the case;

and wherein said surgical system the driving means constitutes a gas-pressure rotary-knock mechanism in which compressed air or high-pressure gas ejected sequentially through the hollow-organ-insertable unit in response to trigger operations on the gas shooter pushes against the piston and advances the knock member while the pressing teeth follow along the cam grooves, and the rotary member rotates one pitch angle at a time when the pressing teeth contact and slide over the sloped surfaces formed on the end-faces of the protruding parts.

The invention described in Claim 12 is a surgical system for small-pit closure in hollow organs according to any of claims 1 through 11, wherein the gas shooter generates compressed air by driving the piston of a gas cylinder device in the retracting direction by a motor, thereby storing energy in a compression spring, and then rapidly advancing the piston by the repelling force of the compression spring by controlling, through a trigger operation, the actuation of the motor.

The invention described in Claim 13 is a surgical system for small-pit closure in hollow organs according to any one of Claims 1 through 11, wherein the piston of the gas cylinder device in the gas shooter is manually pulled in the retracting direction, thereby storing energy in a compression spring, and is then locked, with the piston rapidly advancing due to the repelling force of the compression spring when the lock is released through a trigger operation.

The invention described in Claim 14 is a surgical system for small-pit closure in hollow organs according to any of Claims 1 through 13, further provided with a feed-air-pressure controller on the side of the gas shooter, for adjusting the pressure of the compressed air or high-pressure gas so that the compressed air or high-pressure gas is ejected to a desired magnitude.

The invention described in Claim 15 is a surgical system for small-pit closure in hollow organs according to any of Claims 1 through 5, 7, or 8, wherein each arrowy-shaped member includes a linear, rod-like, or strip-like body having an engaging part that is elastic and formed in a hook shape on or near the leading end of the arrowy-shaped member and that is angled outward toward the rear.

The invention described in Claim 16 is a surgical system for small-pit closure in hollow organs according to Claim 15, further including partitioning members that are provided on or near the rear ends of the arrowy-shaped members, that are generally shaped like discs or short cylinders, that are formed of a material that is biocompatible with the hollow organ or that is either digestible or soluble or capable of being discharged from the body, and that freely slide in the tubular members in a generally hermetic state therewith.

The invention described in Claim 17 is a surgical system for small-pit closure in hollow organs according to Claim 15, further including vanes that (1) have a generally conical shape, (2) are connected to the rear ends of the arrowy-shaped members, (3) are formed of a film-like material that is biocompatible with the hollow organ or that is either digestible or soluble or capable of being discharged from the body, (4) expand outward toward the rear and (5) are freely slidable in the tubular members while maintaining a generally hermetic state therewith.

The invention described in Claim 18 is a surgical system for small-pit closure in hollow organs according to any of Claims 1 through 5, 7, or 8, wherein each of the paired arrowy-shaped members has a generally round bar-shaped or cylindrical body with a sharply formed leading end, with one or multiple elastic engaging parts formed on side surfaces near said leading end and angling outward toward the rear in a hook shape for engaging with tissue in the hollow organ.

The invention described in Claim 19 is a surgical system for small-pit closure in hollow organs according to Claim 18, wherein the engaging parts of the arrowy-shaped members are formed by cutting and spreading outward side surfaces of the generally round bar-shaped, cylindrical, or conical bodies.

The invention described in Claim 20 is a surgical system for small-pit closure in hollow organs according to Claim 18, wherein the arrowy-shaped members are generally round bar-shaped, cylindrical, or conical bodies whose side surfaces are partially cut out to form notches, and the engaging parts of the arrowy-shaped members are formed by fixing one end of a linear or strip-like body to each of the notch parts.

The invention described in Claim 21 is a surgical system for small-pit closure in hollow organs according to any of Claims 1 through 4 or 15 through 20, and further including a suture-thread-insertion part provided on the rear end of the second arrowy-shaped member, and having a ratchet mechanism through which the suture thread is inserted so that the suture thread can be pulled freely in the withdrawal direction, but restricts the suture thread from being pulled back in the return direction.

The invention described in Claim 22 is a surgical system for small-pit closure in hollow organs according to Claim 21, wherein the ratchet mechanism includes an insertion-hole unit through which the suture thread is inserted and that is supported by an elastic support member that is capable of deforming to allow the suture thread to be pulled in the withdrawal direction when the diameter of the insertion-hole increases, while preventing the suture thread from moving in the return direction when the diameter of the insertion-hole decreases.

The invention described in Claim 23 is a surgical system for small-pit closure in hollow organs according to Claim 21, wherein the ratchet mechanism includes a suture thread formed of a deformable material that is inserted through an insertion-hole unit formed slightly narrower than the diameter of the suture thread so that the suture thread is freely pulled in the withdrawal direction by contracting in diameter when constricted in the insertion-hole unit, but is restricted from moving in the return direction because the suture thread expands in diameter when the suture thread moves in the return direction, much like raised hackles, against the outer surface adjacent to the insertion-hole unit.

The invention described in Claim 24 is a surgical system for small-pit closure in hollow organs according to Claim 22 or Claim 23, wherein the inner surface of the insertion-hole unit is tapered and gradually narrows in diameter in the direction that the suture thread is pulled.

The invention described in Claim 25 is a surgical system for small-pit closure in hollow organs according to any of Claims 18 through 24, wherein an insertion hole for inserting the suture thread is provided in a side surface of the second arrowy-shaped member near the rear end thereof and communicates with the suture-thread-insertion unit.

The invention described in Claim 26 is a surgical system for small-pit closure in hollow organs according to any of Claims 1 through 25, wherein a slit-like opening for inserting each of the suture threads penetrates the tube walls in the coupled portion of the tubes from the leading end of the suture-member cartridge, and multiple pairs of the arrowy-shaped members are arranged in series at substantially regular intervals and accommodated in the tubular members; and plungers in the auxiliary shooting unit advance rapidly in sequence at a prescribed stroke when compressed air or high-pressure gas is sequentially ejected in response to a trigger operation on the gas shooter, ejecting each pair of arrowy-shaped members sequentially.

The invention described in Claim 27 is a surgical system for small-pit closure in hollow organs according to Claim 26, wherein the auxiliary shooting unit has a double-cylinder structure, including open-ended cylinders, with the inner cylinders being accommodated in the open-ended cylinders and being capable of moving forward and rearward, with the inner cylinders accommodating a pair of plungers that move freely forward and rearward while maintaining a hermetic seal with the inner cylinders; and the inner cylinders advance one pitch equivalent to the substantially regular intervals of the arrowy-shaped members each time one pair of the arrowy-shaped members is ejected, establishing a new ejection starting point.

Effects of the Invention

According to the invention of Claim 1, the hollow-organ-insertable unit on which the suture-member cartridge is coupled at the leading end of the surgical device for small-pit closure in hollow organs is inserted through a natural orifice in a body via an operating channel of an endoscope into a hollow organ having a small pit; the arrowy-shaped members are sequentially ejected from the suture-member cartridge by compressed air or high-pressure gas discharged from the gas shooter into the suture-member cartridge and are driven into tissue in the hollow organ on both sides of the small-pit site;

the rear ends of the arrowy-shaped members are drawn together via the suture tissue linking those rear ends, whereby the tissue around the small-pit site can easily be closed and held in a sutured state. Hence, it is possible to provide a surgical system and method for small-pit closure in hollow organs that reduces the duration and invasiveness of surgery by eliminating the need for conventional major surgical procedures, such as abdominal incisions, and that is excellent in operability, safety, and reliability.

The invention of Claim 2 differs from the invention of Claim 1 in that the invention of Claim 2 uses a compact capsule endoscope in place of the usual large endoscope; and the hollow-organ-insertable unit on which the suture-member cartridge is coupled on the leading end of the surgical device is inserted directly through a natural orifice into the hollow organ having a small pit in order to suture tissue in the hollow organ around the small-pit site. Hence, in addition to having effects similar to those of Claim 1, it is possible to further reduce suffering by the patient and to eliminate the potential for internal damage to the operating channels of the endoscope. It is also possible to improve the freedom in designing the surgical device of the surgical system for small-pit closure in hollow organs, because the device is not constrained by normal conditions of endoscope usage, such as the internal dimensions of the operating channels.

The invention of Claim 3 differs from the invention of Claim 1 in that the surgical device of Claim 3 is arranged along the outer surface of the endoscope up to the leading-end portion thereof. Therefore, in addition to having effects similar to those of Claim 1, it is possible to eliminate the potential for internal damage to the operating channels of the endoscope and to improve the freedom for designing the surgical device of the surgical system for small-pit closure in hollow organs, because the device is not constrained by the internal dimensions of the operating channels and the like.

The invention of Claim 4 differs from the invention of Claim 3 in that the feed-air switching mechanism and the suture-member cartridge that are provided with multiple pairs of air tubes for accommodating the arrowy-shaped members are, in the invention of Claim 4, disposed on the outer surface of the leading-end of the endoscope, and the hollow-organ-insertable unit that is configured of a single air tube is arranged along the outer surface of the hollow-organ-insertable unit's tube part. Therefore, in addition to having effects similar to those of Claim 1, the surgical system of the invention of Claim 4 can be provided with multiple pairs of air tubes accommodating arrowy-shaped members, while reducing the width of the hollow-organ-insertable unit. Hence, it is possible to further reduce the duration and invasiveness of surgery by efficiently forming multiple sutures in tissue of the hollow organ around the small pit.

The invention of Claim 5 differs from the invention of Claims 2 through 4 in that in the invention of Claim 5 each pair of the tubular members in the surgical device for small-pit closure in hollow organs and the narrow tube interposed therebetween are arranged alongside the outer surface of the leading-end portion of the endoscope; the middle portion of the suture thread is inserted into a U-shaped loop through the threading member, is accommodated in the narrow tube, and is connected to the pulling means; and the rear ends of the arrowy-shaped member that are embedded in tissue of the hollow organ on both sides of the small-pit site are drawn together by pulling the middle portion of the suture thread with the pulling means. Therefore, in addition to having effects similar to those of Claims 2 through 4, the surgical system of the invention of Claim 5, by drawing together the rear ends of the arrowy-shaped member while the suture thread is symmetrically connected to the arrowy-shaped member, can improve operability while eliminating the need to retract the endoscope when forming a suture.

According to the invention of Claim 6, the pulling means includes a wire-take-up means that rotates in the direction for taking up the wire in response to a trigger operation. Accordingly, in addition to having effects similar to those of Claim 5, the surgical system of the invention of Claim 6 can further improve operability for suturing the site of a small pit Tc in a hollow organ T by drawing together the rear ends of the arrowy-shaped member.

According to the invention of Claim 7, an auxiliary shooting unit is interposed between the suture-member cartridge and the hollow-organ-insertable unit in order to generate secondary compressed air near the suture-member cartridge. Accordingly, in addition to having effects similar to those of Claims 1 through 6, the surgical system of Claim 7 can improve the operability and reliability of sequentially ejecting arrowy-shaped members from the suture-member cartridge.

According to the invention of Claim 8, the surgical device includes multiple pairs of suture-member cartridges and air tubes that are arranged parallel to each other. Accordingly, in addition to having effects similar to those of Claims 5 through 7, because multiple suture members can be sequentially ejected from the multiple pairs of suture-member cartridges arranged parallel to each other, multiple sutures can be formed in tissue around a small-pit site by inserting the surgical device into the hollow organ one time, thereby reducing the duration and invasiveness of surgery, improving the efficiency of surgery, and reducing discomfort to the patient.

According to the invention of Claim 9, a feed-air switching mechanism is interposed between the hollow-organ-insertable unit and the gas shooter in order to switch between a circulation state for supplying compressed air or high-pressure gas sequentially into each air tube in the hollow-organ-insertable unit and a non-circulation state for blocking the compressed air or high-pressure gas. Accordingly, in addition to having effects similar to those of Claims 1 through 3 or 5 through 7, because compressed air or high-pressure gas ejected from the gas shooter is reliably supplied to each air tube of the suture-member cartridge, to each open-ended cylinder, and to each tubular member sequentially via the hollow-organ-insertable unit, it is possible to further improve operability and reliability for sequentially ejecting the arrowy-shaped members.

According to the invention of Claim 10, the feed-air switching mechanism includes driving means for rotating the rotary member in association with a trigger operation on the gas shooter, with said rotary member having a switching plate for sequentially switching the two positions of the circulation state achieved with an opening and a non-circulation state achieved with a shielding part that includes the portion of the switching plate other than the opening. Accordingly, in addition to having effects similar to those of Claim 4 or Claim 9, the surgical system of the invention of Claim 10 achieves operability for automatically and sequentially switching the two positions of the circulation state and non-circulation state for compressed air or high-pressure gas through a single trigger operation, and can further improve the operability and reliability for ejecting the arrowy-shaped members sequentially from the suture-member cartridge by discharging compressed air or high-pressure gas.

According to the invention of Claim 11, the driving means is a gas-pressure rotary-knock mechanism in which compressed air or high-pressure gas ejected sequentially from the gas shooter in response to trigger operations pushes against the piston and advances the knock member while the pressing teeth follow along the cam grooves in the cam cylinder, and the rotary member rotates one pitch angle at a time when the pressing teeth contact and slide over the sloped surfaces formed on the end-faces of the protruding parts. Accordingly, in addition to having effects similar to those of Claim 10, the surgical system of Claim 11 can achieve reliability in the feed-air switching mechanism, and through a single trigger operation can operate to automatically and sequentially switch the two positions of the circulation state and the non-circulation state for the compressed air or high-pressure gas.

According to the invention of Claim 12, compressed air is generated by controlling the actuation of a motor through trigger operations and by rapidly advancing the piston with the repelling force of a compression spring. Accordingly, in addition to having effects similar to those of Claims 1 through 11, it is possible to drive arrowy-shaped member into tissue of a hollow organ around a small-pit site automatically by a single trigger operation, thereby improving the operability and efficiency for small-pit closure surgery in hollow organs.

According to the invention of Claim 13, the gas shooter has a simple structure in which the piston of the gas cylinder device is pulled manually in the retracting direction and locked by energy accumulated in the compression spring, and compressed air is generated by releasing the lock through a trigger operation to advance the piston rapidly with the repelling force of the compression spring. Accordingly, in addition to having effects similar to those of Claims 1 through 11, the structure of the gas shooter can be further simplified and made more reliable and economical.

According to the invention of Claim 14, in addition to having effects similar to those of Claims 1 through 13, the feed-air-pressure controller can easily adjust the pressure of compressed air or high-pressure gas to a desired magnitude in accordance with circumstances relating to the tissue in the hollow organ at the small-pit site, the type and size of the arrowy-shaped member, and the like, thereby improving the operability and convenience of the surgical device.

According to the invention of Claim 15, in addition to having effects similar to those of Claims 1 through 5, 7, or 8, the arrowy-shaped member can be formed in a narrow shape configured of linear, rod-like, or strip-like bodies. Accordingly, the arrowy-shaped members readily enter tissue in the hollow organ, thereby reducing discomfort for the patient.

According to the invention of Claim 16, in addition to having effects similar to those of Claim 15, compressed air generated secondarily by compressed air gas released from the gas shooter via the auxiliary shooting unit is received fully by the generally disc-shaped or short-cylinder-shaped partitioning members and can reliably eject, one after another, arrowy-shaped member comprising linear, rod-like, or strip-like bodies.

According to the invention of Claim 17, in addition to having effects similar to those of Claim 15, compressed air generated secondarily by compressed air or high-pressure gas released from the gas shooter via the auxiliary shooting unit is received fully by the generally conical-shaped vanes and can more reliably eject, one after another, smoothly and stably, the arrowy-shaped member comprising linear, rod-like, or strip-like bodies.

According to the invention of Claim 18, in addition to having effects similar to those of Claim 7 or Claim 8, the arrowy-shaped member have generally round bar-shaped, cylindrical, or conical bodies with pointed leading ends. Accordingly, the arrowy-shaped member themselves can fully receive secondary compressed air generated by compressed air or high-pressure gas released from the gas shooter via the auxiliary shooting unit, without the need for partitioning members, and the arrowy-shaped member can smoothly and reliably be ejected one after another, and particularly can ensure hemostasis owing to their solid form. Therefore, the arrowy-shaped members are applicable to patients with unusual conditions, such as a tendency to hemorrhage, myocardial infarction, cerebral infarction, or cirrhosis, and to patients having prosthetic valves.

According to the invention of Claim 19, in addition to having effects similar to those of Claim 18, the engaging parts of the arrowy-shaped member are easily formed by cutting and spreading outward the side surfaces of bar-shaped bodies.

According to the invention of Claim 20, in addition to having effects similar to those of Claim 18, slender engaging parts are formed on the arrowy-shaped member by fixing one end of each of the linear or strip-like bodies to notch parts formed in the side surfaces of bar-shaped bodies. Accordingly, the arrowy-shaped members readily enter and engage with tissue in the hollow organ, reducing discomfort for the patient. 9

According to the invention of Claim 21, the suture-thread-insertion part provided on the rear end of the second arrowy-shaped member has a ratchet mechanism for allowing the suture thread to be pulled through, but restricting its return. Accordingly, in addition to having effects similar to those of Claims 15 through 20, the rear ends of the pair of arrowy-shaped member driven into tissue in the hollow organ around the site of the small pit can be drawn together simply by pulling the suture thread. Therefore, the tissue around the small-pit site can be quickly closed and held in a sutured state through one simple operation.

According to the invention of Claim 22, in addition to having effects similar to those of Claim 21, the insertion-hole unit of the ratchet mechanism is supported by an elastic support member capable of deforming to allow the suture thread to be pulled in the withdrawal direction when the diameter of the suture thread increases, while preventing the suture thread from returning in the return direction when the diameter of the suture thread decreases, thereby ensuring reliability of the ratchet mechanism.

According to the invention of Claim 23, the suture thread is formed of a deformable material so that when inserted through the insertion-hole unit formed slightly narrower than the diameter of the suture thread, the suture thread is freely pulled in the withdrawal direction by itself contracting in diameter when constricted in the insertion-hole unit, but is restricted from moving in the return direction because the suture thread itself expands in diameter, like raised hackles, against the outer surface adjacent to the insertion-hole unit. Accordingly, in addition to having effects similar to those of Claim 21, the structure of the insertion-hole unit can be simplified.

According to the invention of Claim 24, the inner surface of the insertion hole has a tapered shape that gradually narrows in diameter in the direction that the suture thread is pulled. Accordingly, in addition to having effects similar to those of Claim 22 or Claim 23, the invention of Claim 24 further improves the reliability of the ratchet mechanism for restricting movement of the suture thread in the return direction because the suture thread itself, when pulled in the return direction, deforms and expands in diameter, like raised hackles, against the outer surface adjacent to the insertion-hole unit.

According to the invention of Claim 25, in addition to having effects similar to those of Claims 18 through 24, suture thread having one end fixed to the rear end of one arrowy-shaped member in the pair can easily be inserted into the insertion hole provided in the side surface of the other arrowy-shaped member near the rear end thereof and passed through to the suture-thread-insertion unit that is in communication with the insertion hole. Hence, the ends of the arrowy-shaped members driven into the tissue of the hollow organ on both sides of the small-pit site can be drawn together simply and smoothly, and the tissue around the small-pit site can be quickly closed through one operation and held reliably in a sutured state.

According to the invention of Claim 26, in addition to having effects similar to those of Claims 1 through 25, multiple pairs of the arrowy-shaped members (suture members) are accommodated at substantially equal intervals in the suture-member cartridge. Accordingly, multiple pairs of suture members can be accommodated in a suture-member cartridge having a minimum diameter, configured of a minimum number of pairs (one pair) of tubular members, for example, and can be sequentially ejected one pair at a time. Hence, because multiple sutures can be formed quickly in the tissue around the small-pit site by inserting the surgical device into the hollow organ just one time, it is possible to further reduce the duration and invasiveness of surgery, to reduce discomfort to the patient, and to increase the efficiency of surgery.

According to the invention of Claim 27, in addition to having effects similar to those of Claim 26, the auxiliary shooting unit has a double-cylinder structure that includes (1) open-ended cylinders (2) inner cylinders that (a) are accommodated in the cylinders that are open at both ends, and (b) can move forward and rearward, and (3) a pair of plungers that move freely forward and rearward while maintaining a hermetic seal with the inner cylinders. Hence, the inner cylinders advance one pitch equivalent to the substantially equal intervals of the arrowy-shaped member to a new ejection starting point each time one pair of arrowy-shaped member (a suture member) is ejected, and secondary compressed air that is generated when the gas shooter discharges compressed air or high-pressure gas via the auxiliary shooting unit can efficiently eject each of the arrowy-shaped member from a nearby position, thereby achieving reliability for smoothly and stably ejecting pairs of arrowy-shaped member in sequence.

BRIEF DESCRIPTIONS OF THE DRAWINGS

FIG. 3(*b*) is a cross-sectional view taken along section line A-A shown in FIG. 3(*a*).

Figure 10:
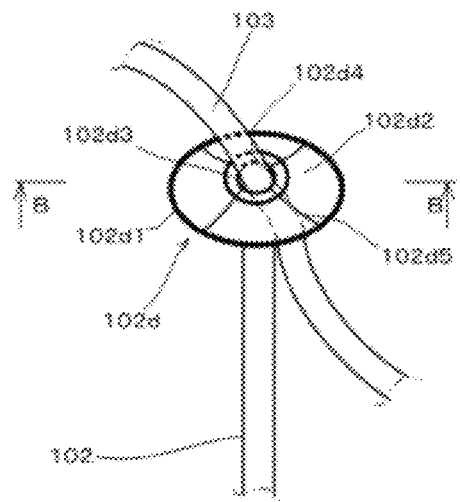
Figure 10:
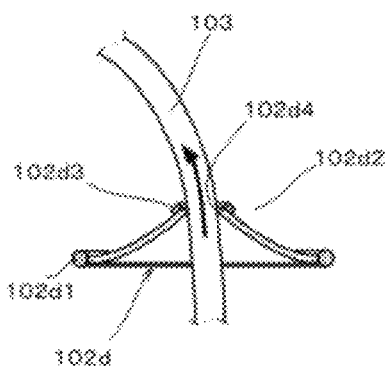
Figure 10:
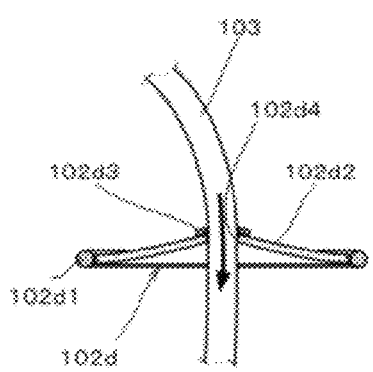

FIG. 10(*a*) is a perspective view; FIG. 10(*b*) is a vertical cross-sectional view in which a suture thread is being pulled away (upward) from the arrowy-shaped member; and FIG. 10(*c*) is a vertical cross-sectional view in which the suture thread is locked (restricted) from returning toward the arrowy-shaped member (downward), conceptually illustrating the operations of a ratchet mechanism of a suture-thread-insertion part on the rear end of an arrowy-shaped member according to a preferred embodiment of the present invention.

Figure 11:
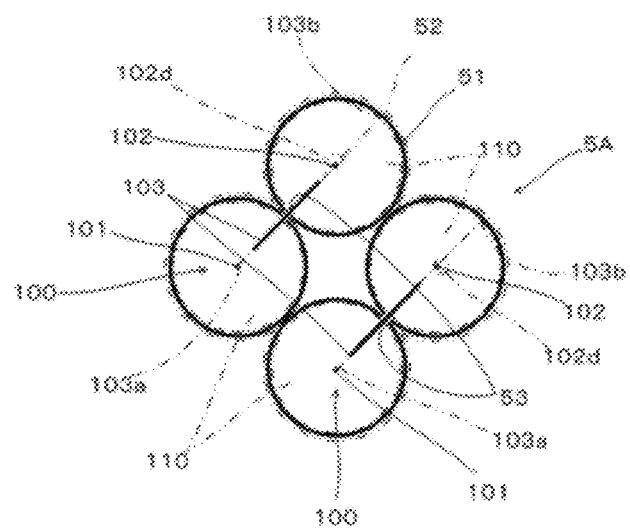

FIG. 11 is a front view showing the structure on the front end of a suture-member cartridge according to another implementation mode of the present invention.

Figure 12:
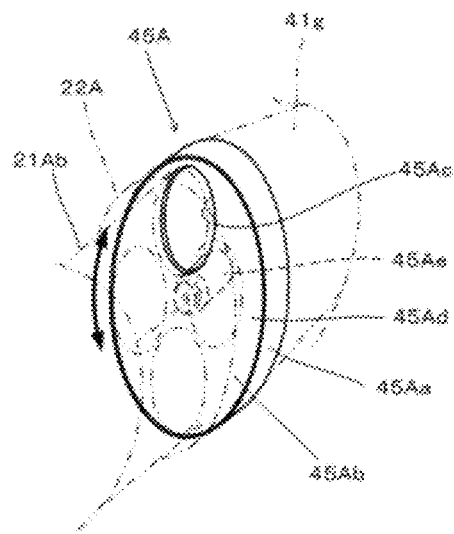

FIG. 12 is a perspective view showing the structural concept of a feed-air switching mechanism (according to a different implantation mode when using the suture-member cartridge of FIG. 11.

Figure 13:
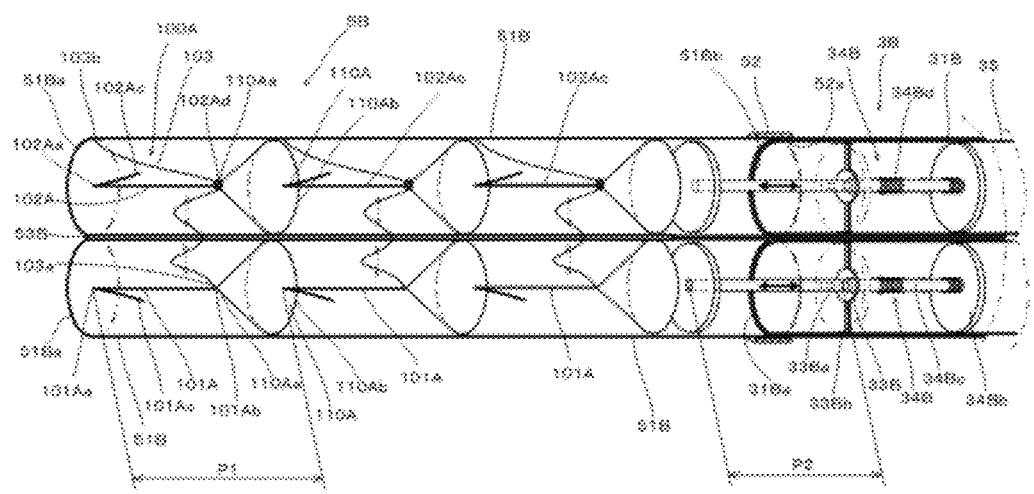

FIG. 13 is a vertical cross-sectional view showing the structural concept of a suture-member cartridge according to another implementation mode of the present invention.

Figure 14:
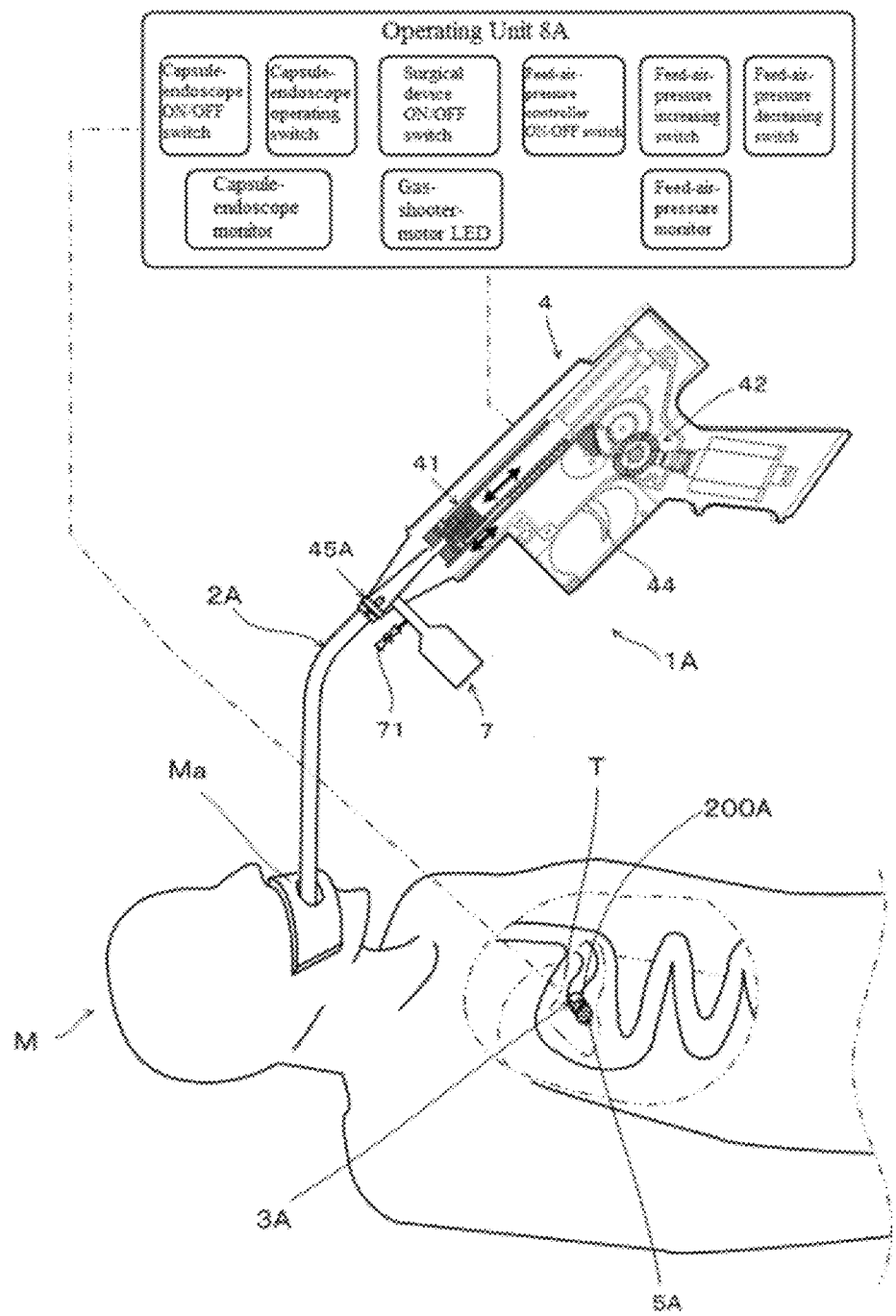

FIG. 14 is a conceptual diagram showing the principal structural concept of a surgical system for small-pit closure in hollow organs according to another embodiment (second embodiment) of the present invention.

Figure 15:
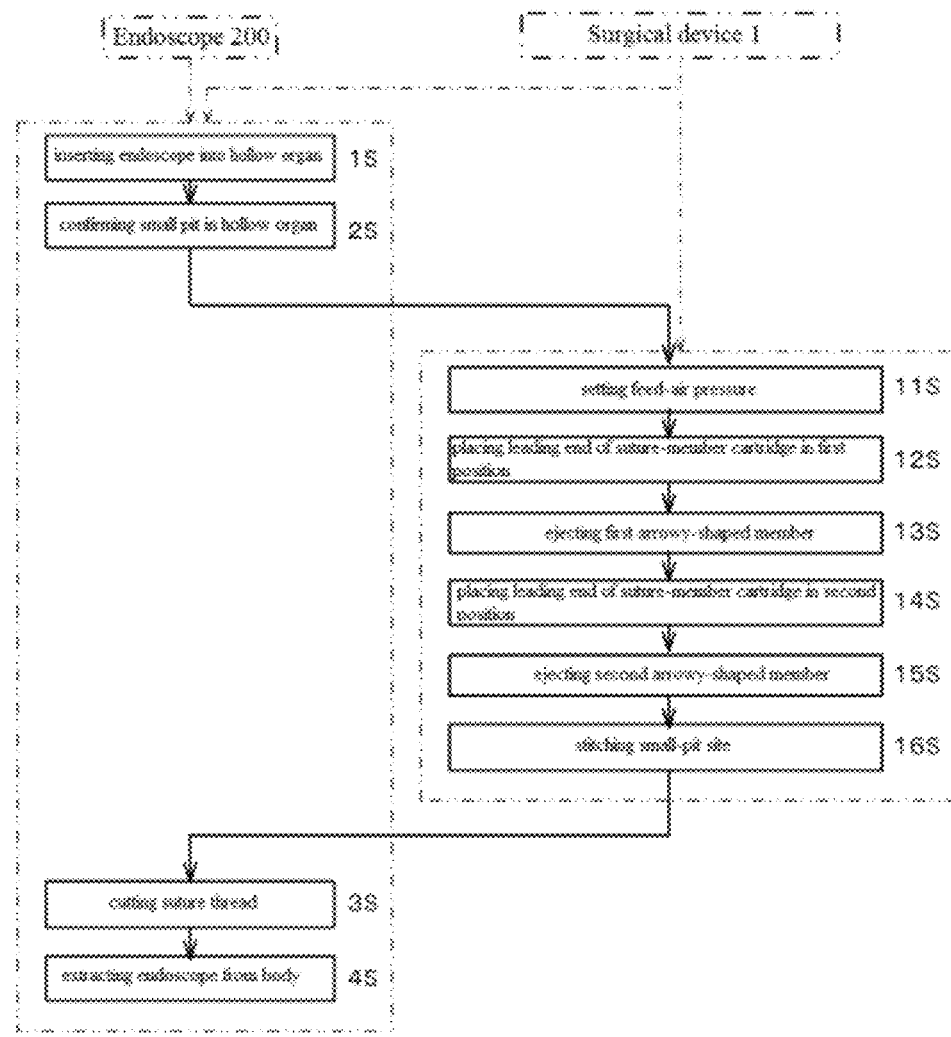

FIG. 15 is a block diagram showing the main steps in a surgical method for small-pit closure in hollow organs according to a preferred embodiment (first embodiment) of the present invention.

Figure 16:
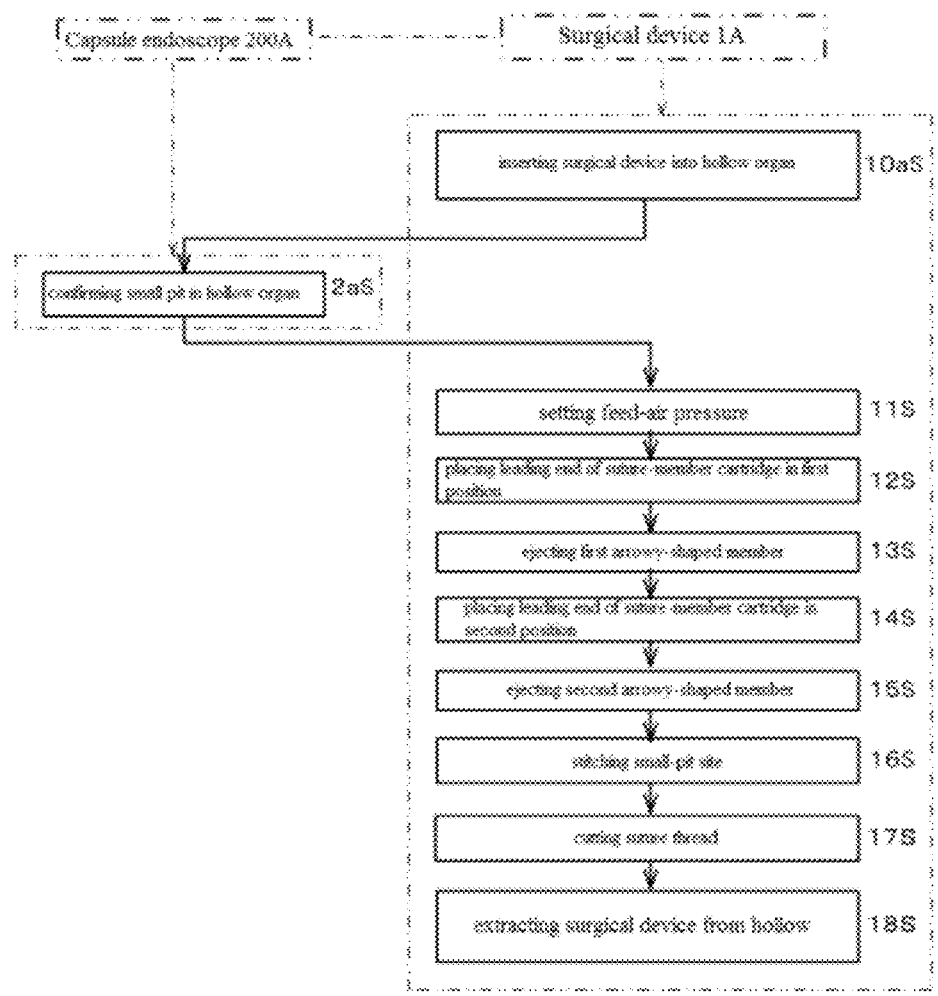

FIG. 16 is a block diagram showing the main steps in a surgical method for small-pit closure in hollow organs according to a preferred embodiment (second embodiment) of the present invention.

Figure 17:
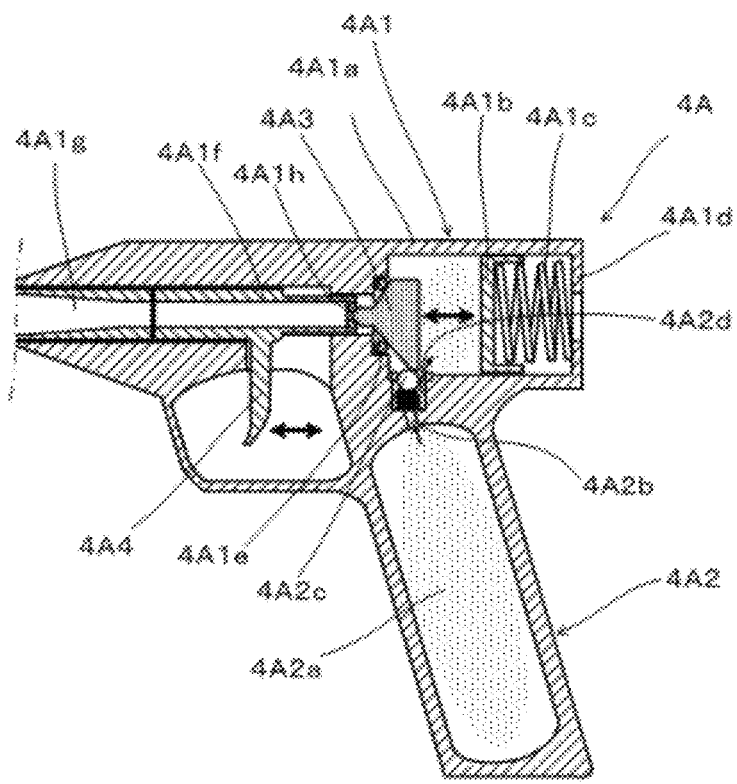
Figure 17:
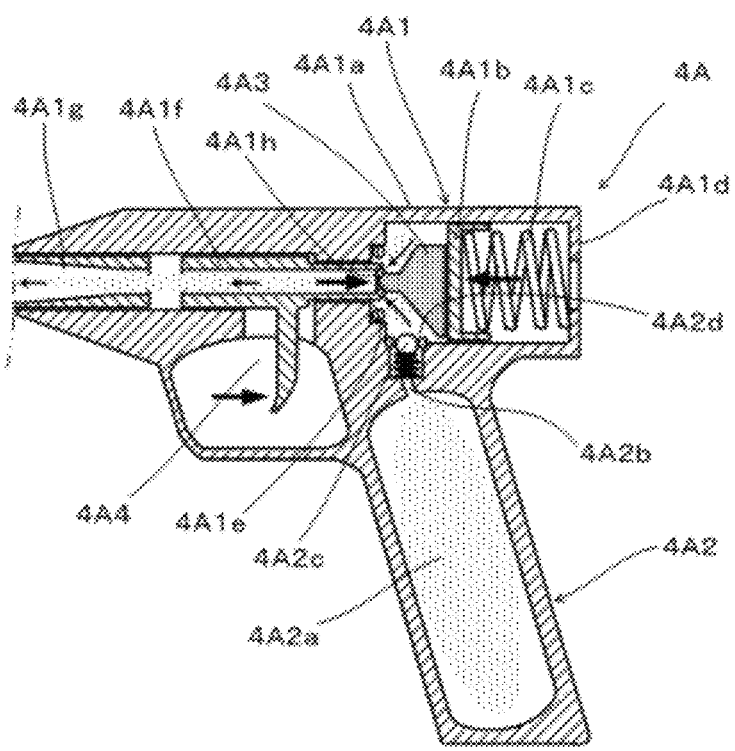

FIG. 17(*a*) is a vertical cross-sectional view showing the structural concept of a gas shooter according to another implementation mode of the present invention when the trigger is in the standby state prior to firing; and FIG. 17(*b*) is a vertical cross-sectional view of the gas shooter in FIG. 17(*a*) when the trigger has been pulled and the gas shooter has fired.

Figure 18:
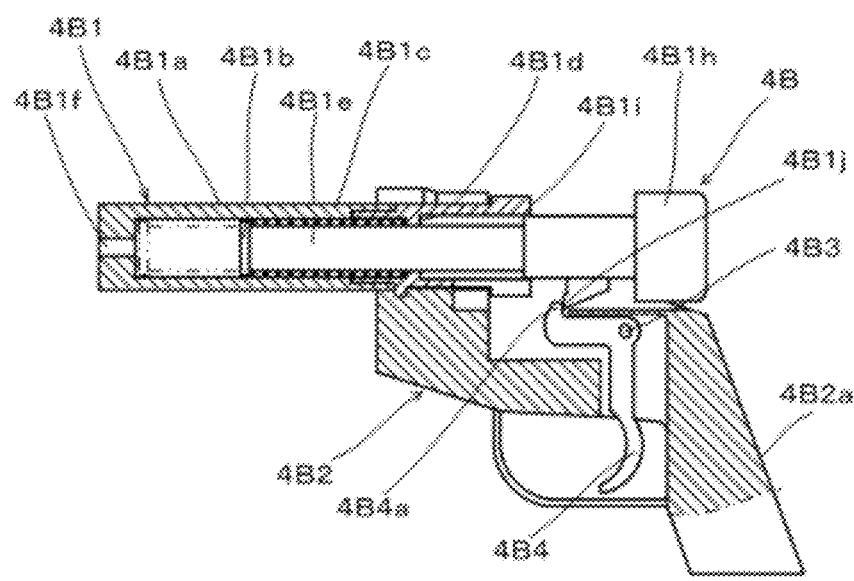
Figure 18:
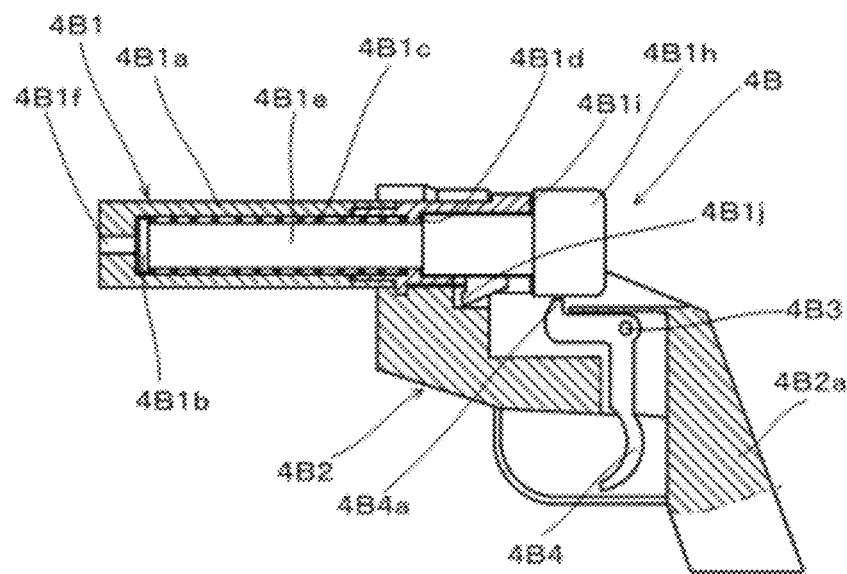

FIG. 18(*a*) is a vertical cross-sectional view showing the structural concept of a gas shooter according to yet another implementation mode of the present invention when a piston has been retracted and locked and the gas shooter is on standby prior to firing; and FIG. 18(*b*) is a vertical cross-sectional view of the gas shooter in FIG. 18(*a*) when the trigger has been pulled and the gas shooter has fired.

Figure 19:
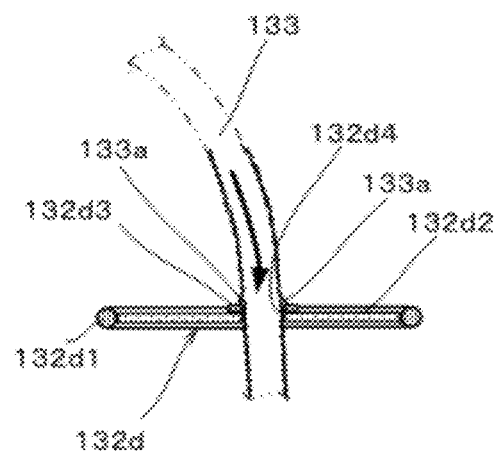
Figure 19:
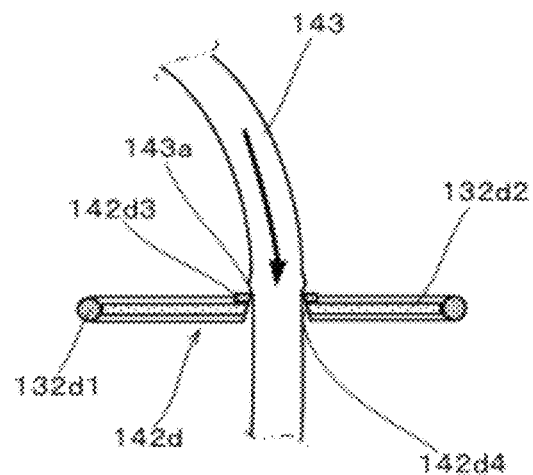

FIG. 19(*a*) is an enlarged vertical cross-sectional view of a ratchet mechanism of a suture-thread-insertion part on the rear end of an arrowy-shaped member according to another implantation mode of the present invention when the suture thread is locked (restricted) from returning toward the arrowy-shaped member (downward); and FIG. 19(*b*) is an enlarged vertical cross-sectional view conceptually showing the operations of the ratchet mechanism of a suture-thread-insertion part provided on the rear end of an arrowy-shaped member according to yet another implantation mode of the present invention when the suture thread is locked (restricted) from returning toward the arrowy-shaped member (downward).

Figure 20:
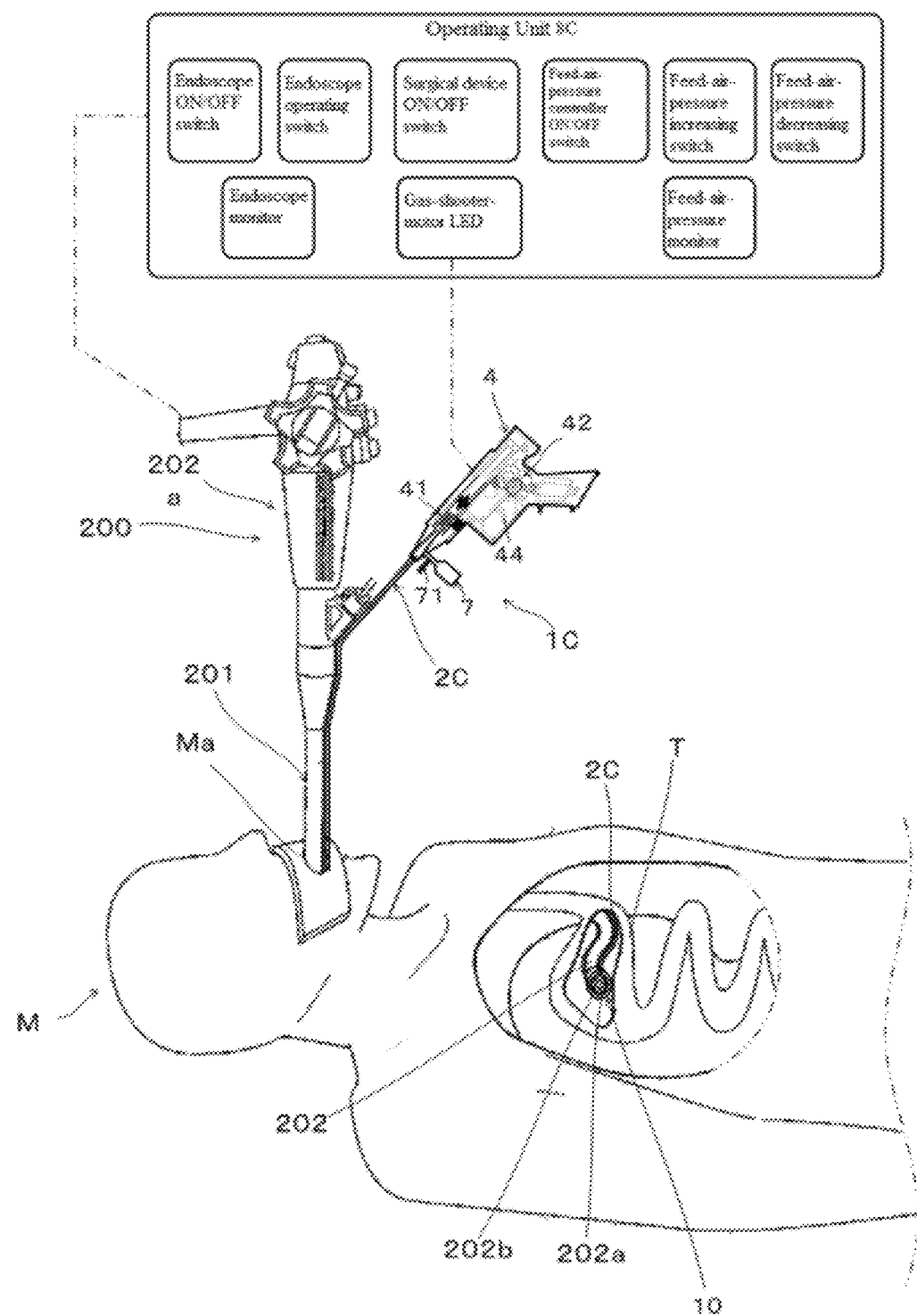

FIG. 20 is a conceptual diagram showing the main structural concept of a surgical system according to a preferred embodiment (third embodiment) of the present invention for small-pit closure in hollow organs.

Figure 21:
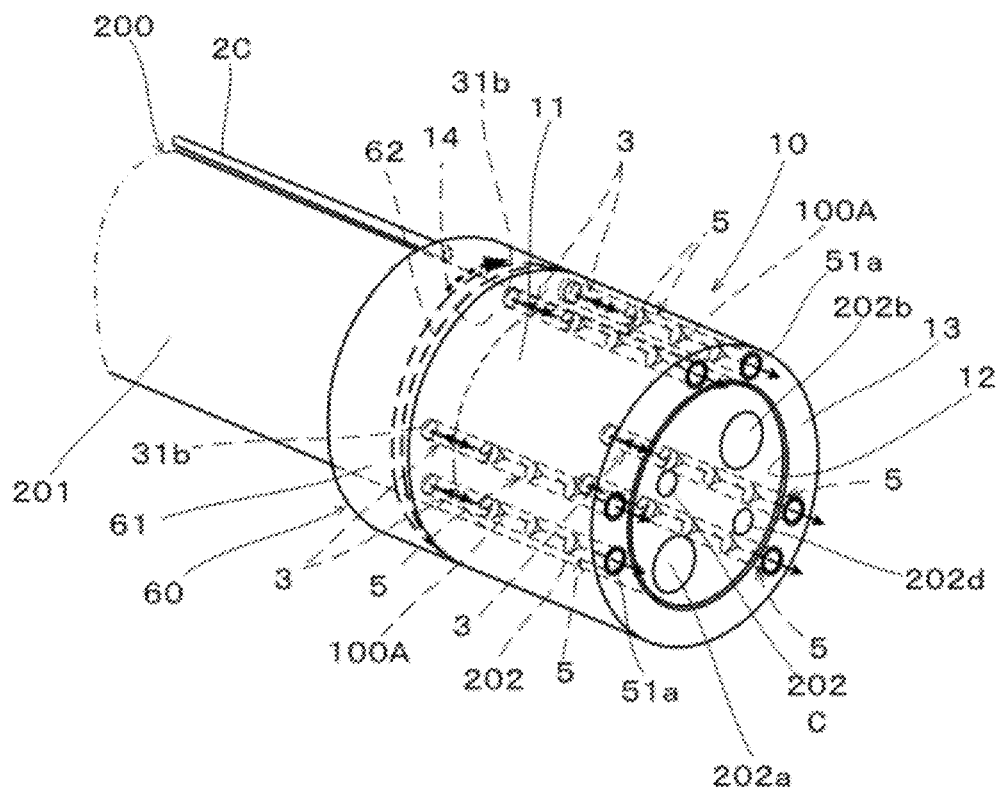

FIG. 21 is a perspective view showing the structural concept of the suture-member cartridge in FIG. 20.

Figure 22:
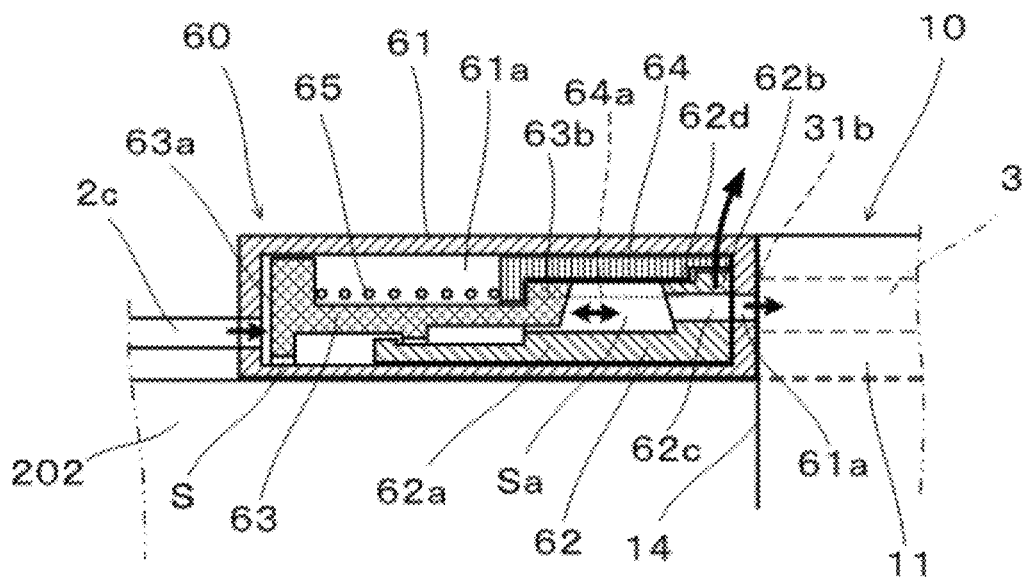

FIG. 22 is a vertical cross-sectional view showing the structural concept of the feed-air switching mechanism shown in FIG. 21.

Figure 23:
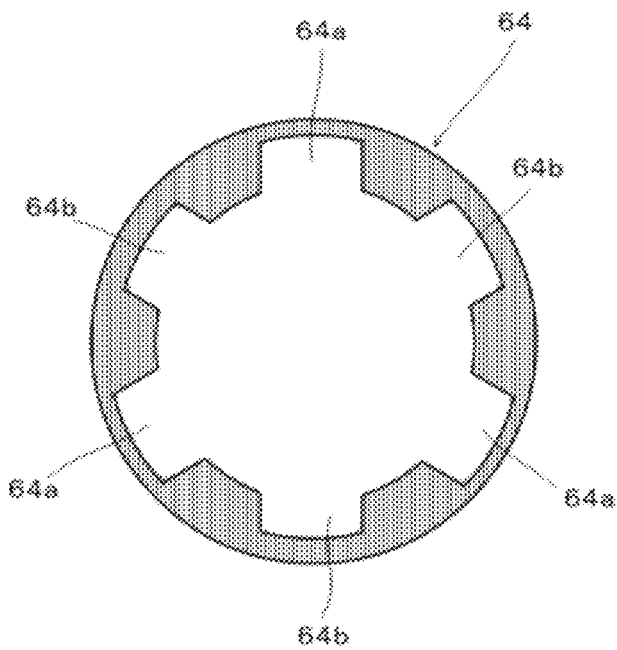

FIG. 23 is a horizontal cross-sectional view showing the structural concept of the cam cylinder in the feed-air switching mechanism of FIG. 22.

Figure 24:
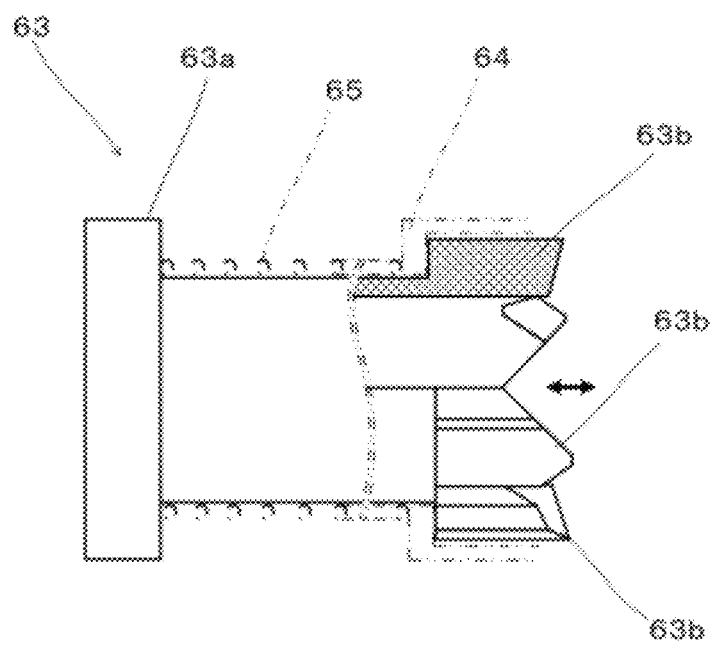

FIG. 24 is a partial vertical cross-sectional view showing the structural concept of the knock member in the feed-air switching mechanism of FIG. 23.

FIGS. 25(a) and 25(b) are development views conceptually illustrating operations of the feed-air switching mechanism shown in FIG. 23 during an inactive state and an operating state, respectively.

Figure 26:
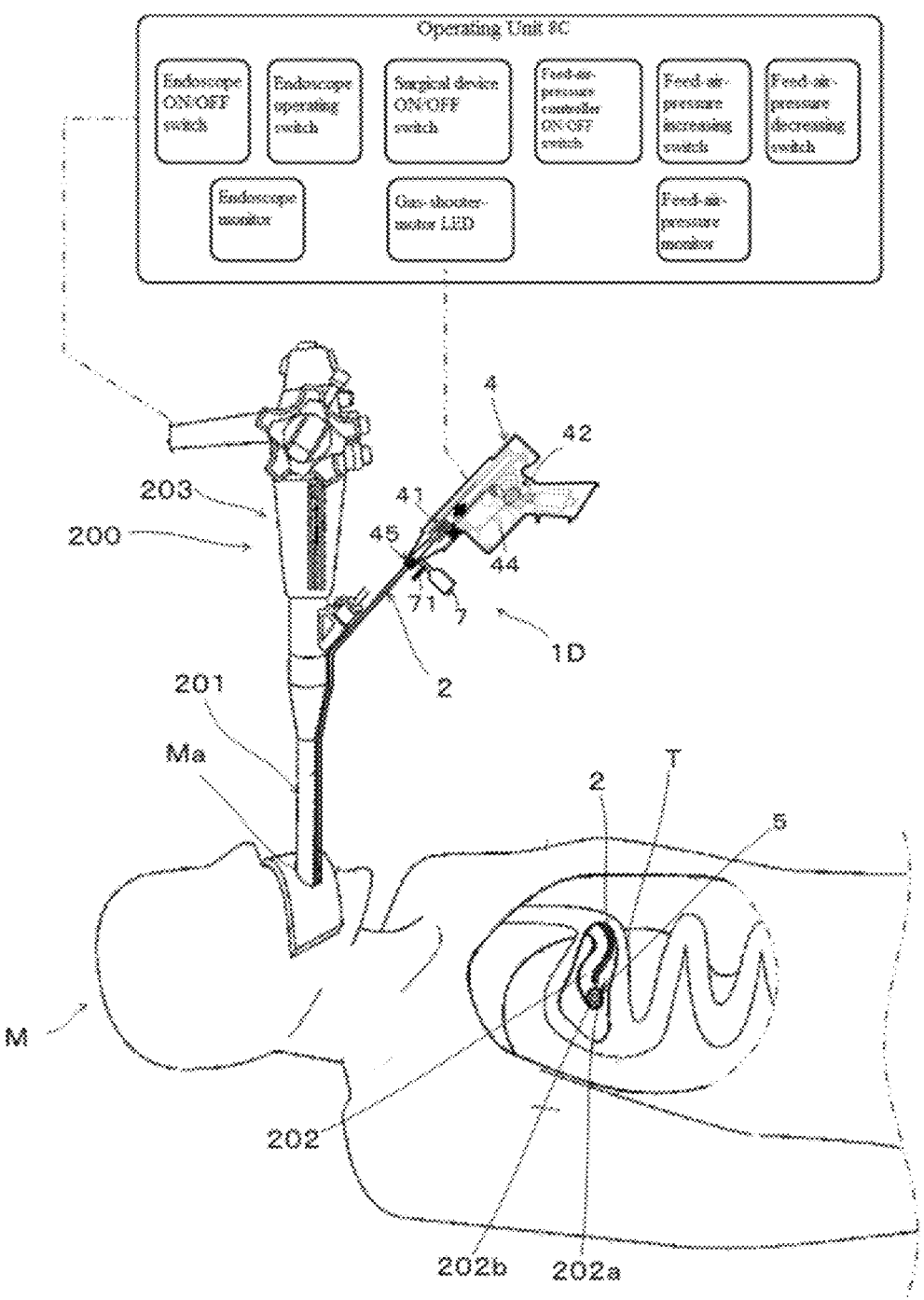

FIG. 26 is a conceptual diagram showing the main structural concept of a surgical system according to a preferred embodiment (fourth embodiment) of the present invention for small-pit closure in hollow organs.

Figure 27:
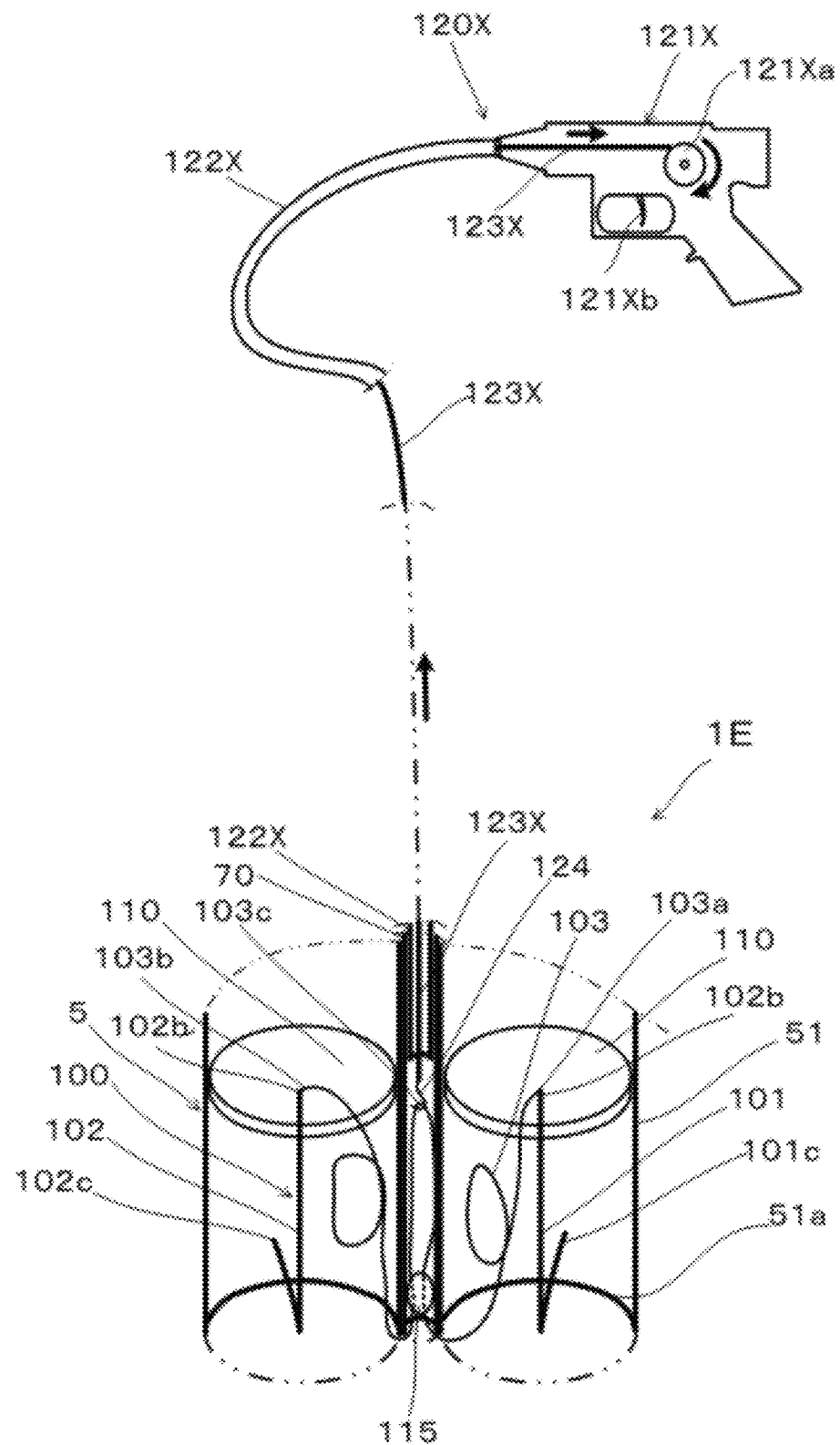

FIG. 27 is a conceptual diagram showing the main structural concept of a surgical system according to a preferred embodiment (fifth embodiment) of the present invention for small-pit closure in hollow organs.

Figure 28:
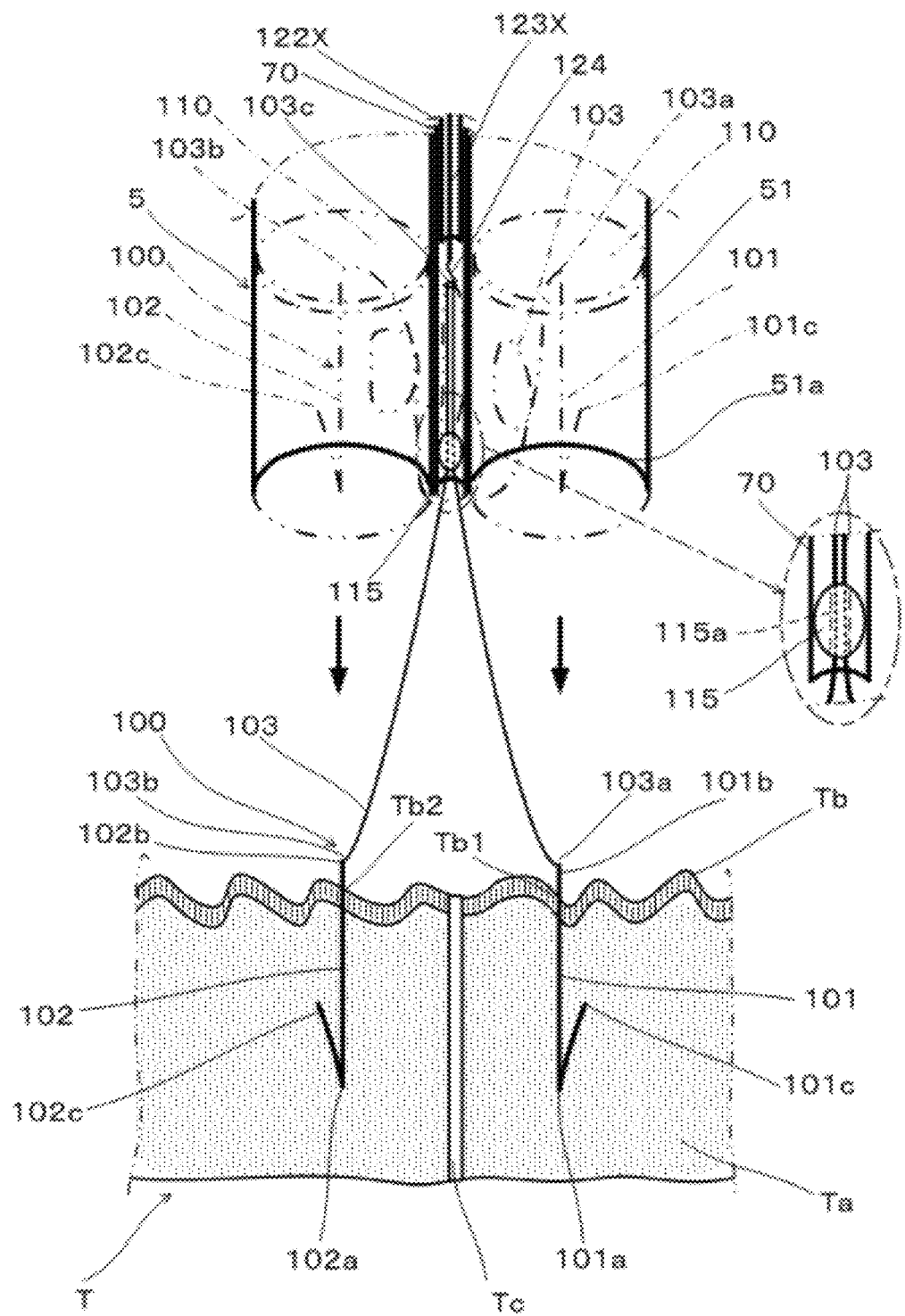

FIG. 28 is a vertical cross-sectional view showing the pair of arrowy-shaped members in FIG. 27 embedded in hollow-organ tissue at a small-pit site.

Figure 29:
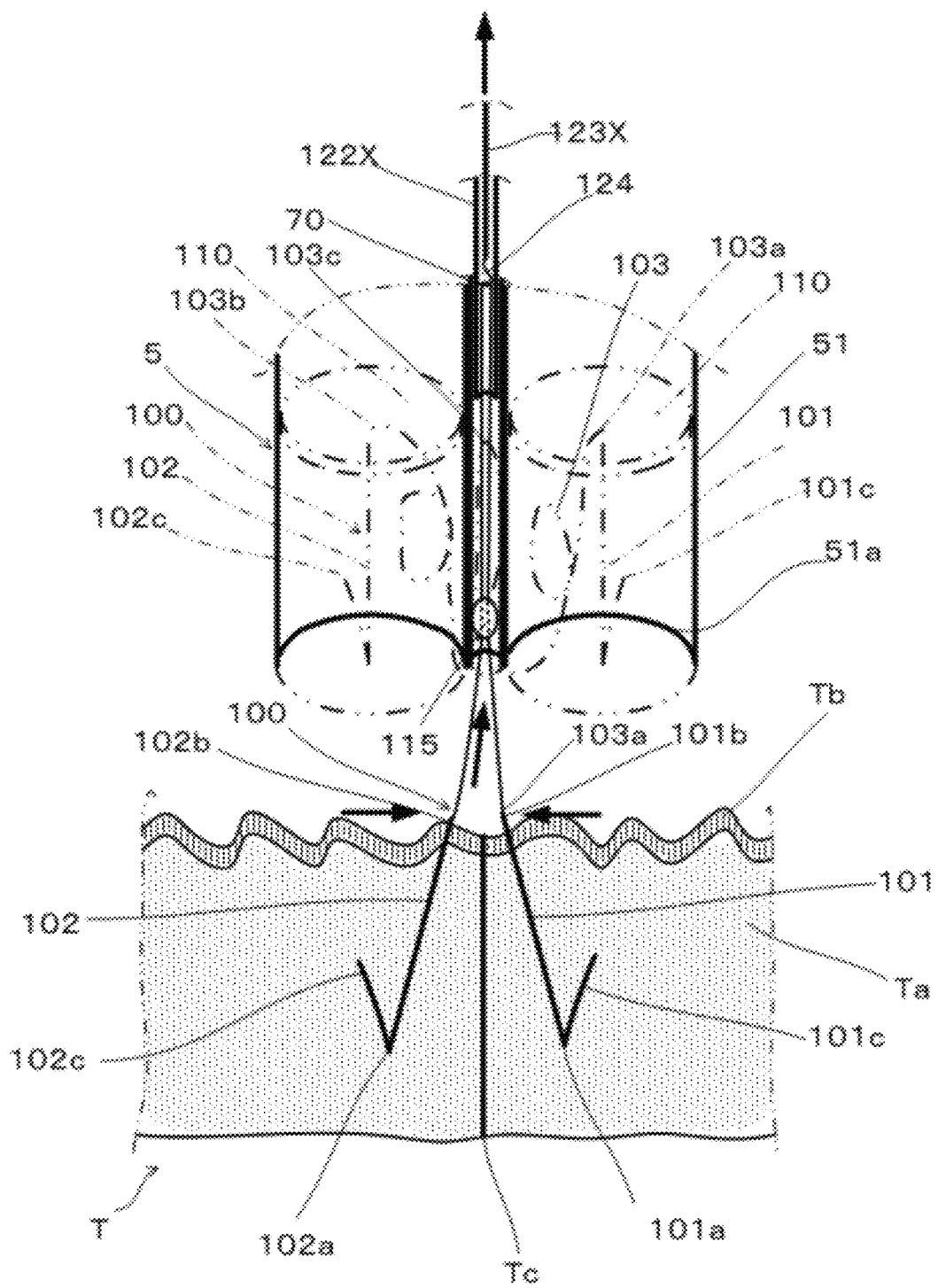

FIG. 29 is a vertical cross-sectional view illustrating a step for stitching the small-pit site as a continuation of the state shown in FIG. 28.

Figure 30:
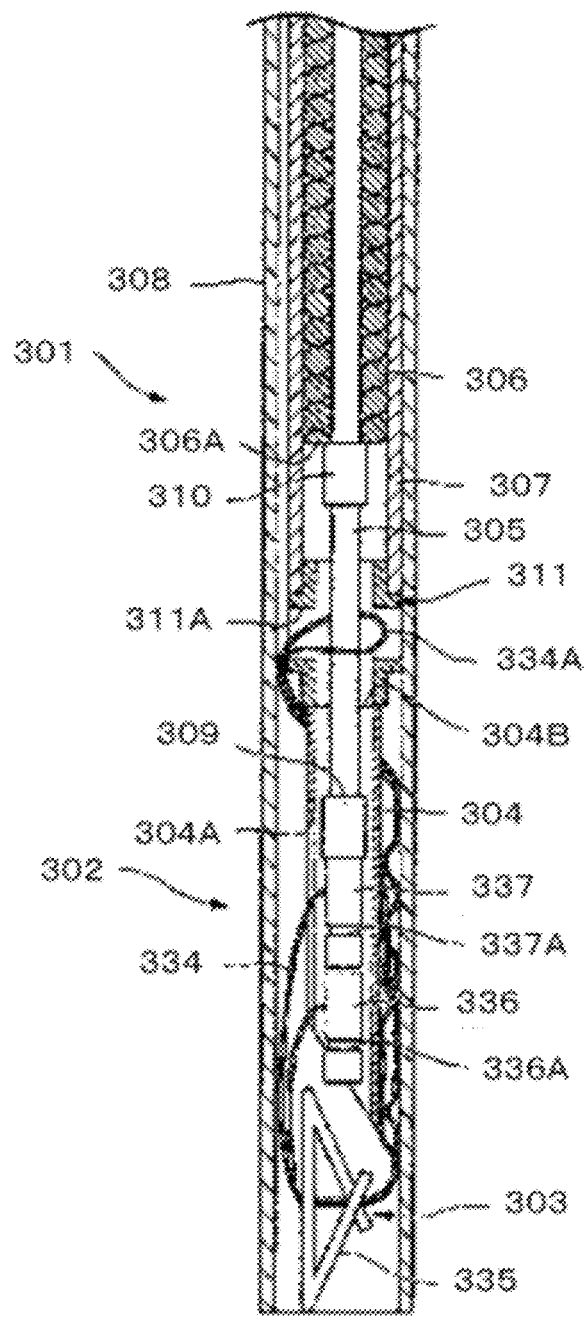

FIG. 30 is a vertical cross-sectional view showing the leading-end of a conventional suturing device (Patent Document 1).

Figure 31:
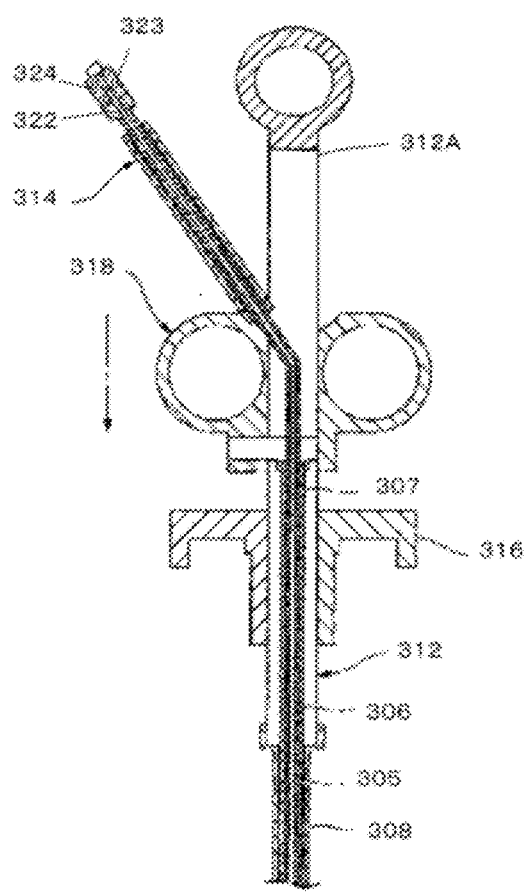
Figure 31:
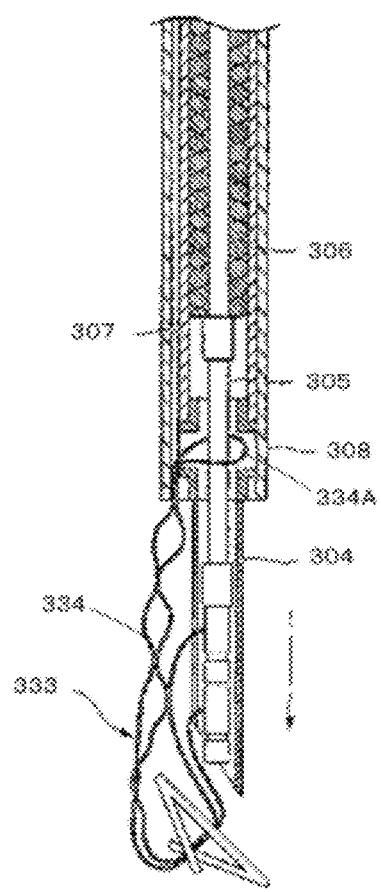

FIGS. 31(a) and 31(b) are vertical cross-sectional views showing the operating part and leading-end, respectively, for the suturing device shown in FIG. 30 when the device is in use.

Figure 32:
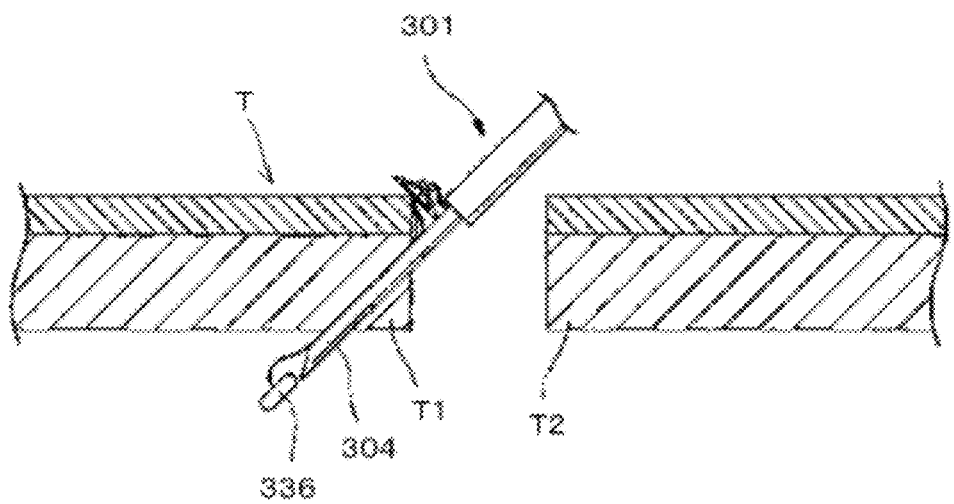

FIG. 32 is a vertical cross-sectional view showing a needle that has been inserted into tissue at the small-pit site from the leading end of the suturing device in FIG. 30 or FIG. 31(b).

Figure 33:
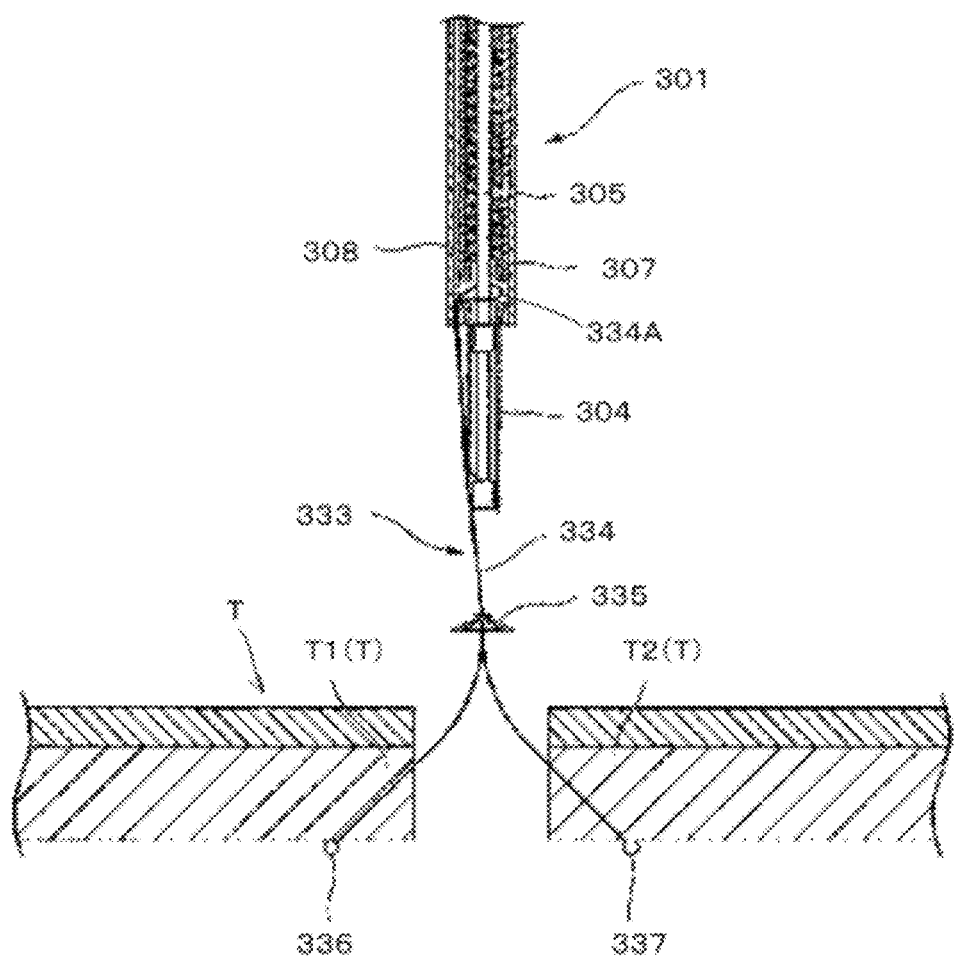

FIG. 33 is a vertical cross-sectional view showing the process of suturing tissue at the small-pit site as a continuation of the state shown in FIG. 32.

Figure 34:
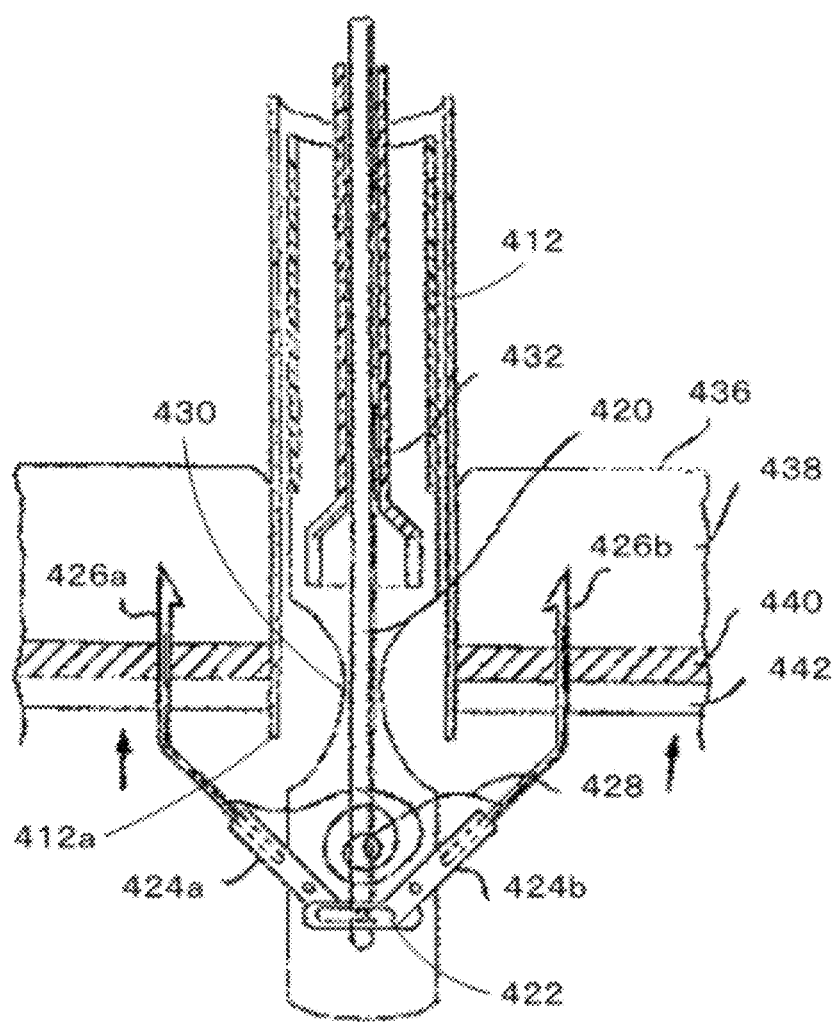

FIG. 34 is a vertical cross-sectional view showing a needle-suture complex of a conventional suture/closure instrument (Patent Document 2) when a pair of opposing needles of the needle-suture complex have pierced tissue around a port (puncture site) in the serous membrane.

Figure 35:
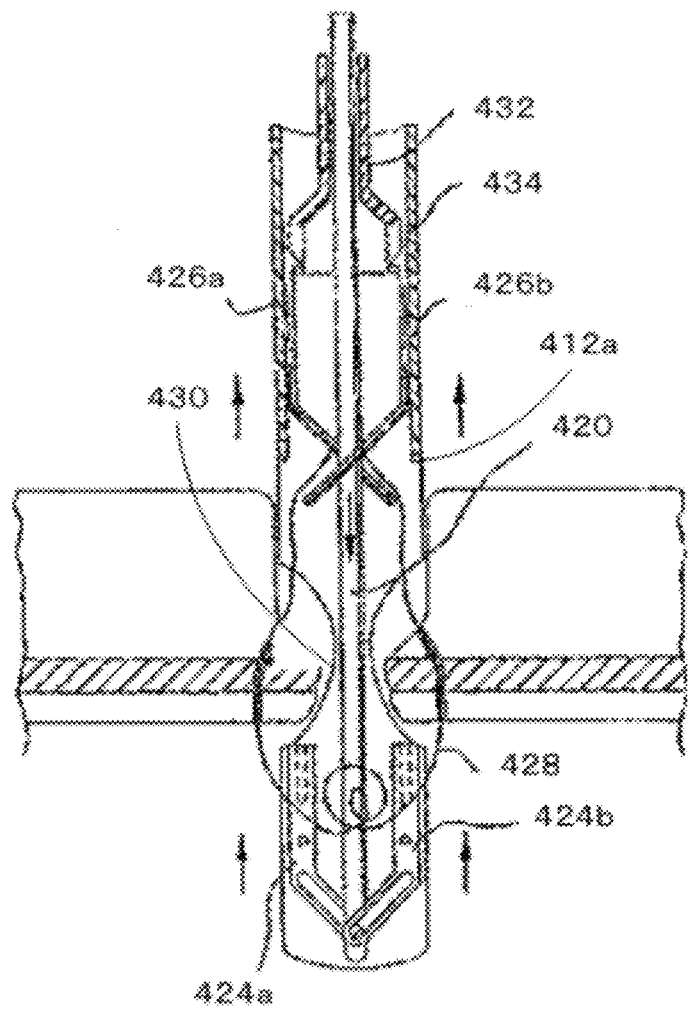

FIG. 35 is a vertical cross-sectional view showing the needle-suture complex of FIG. 34 after the needles have been pulled upward from the port and accommodated in the far end of the suture/closure instrument so as to pass through tissue in the port and become fixed at crossed positions.

Figure 36:
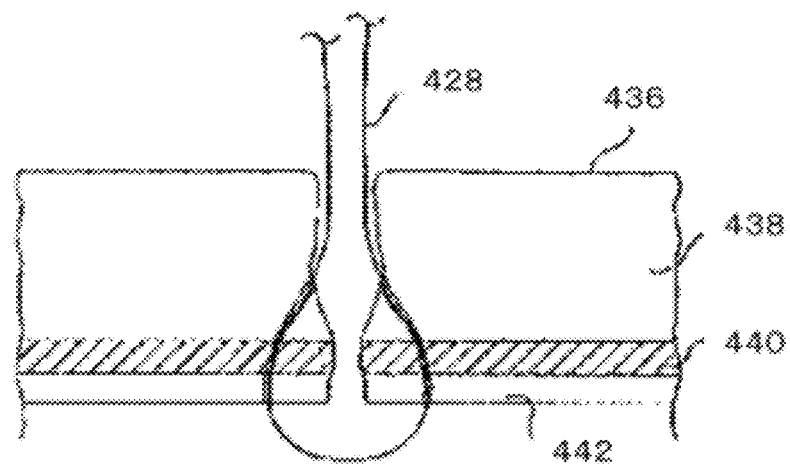

FIG. 36 is a vertical cross-sectional view showing the process for suturing the tissue at the port after the suture/closure instrument has been pulled out of the patient's body as a continuation of the state shown in FIG. 35.

BEST MODES FOR CARRYING OUT THE INVENTION

Preferred embodiments for carrying out the surgical system and method of the present invention for small-pit closure in hollow organs will be described below in detail while referring to the accompanying drawings.

All of the accompanying drawings conceptually illustrate the main structural concept of the invention and are not necessarily drawn to scale. In FIGS. 3 through 13 and 21 through 29, in particular, components are depicted with dimensions exaggerated in the radial direction compared to the axial direction or are enlarged as a whole in order to illustrate the internal structures more clearly. Further, all of the components described below are formed of medically-compatible materials well known in the art. Suture members and other components designed to be left in the body, in particular, are configured of biodegradable materials, for example.

First Embodiment

Figure 1:
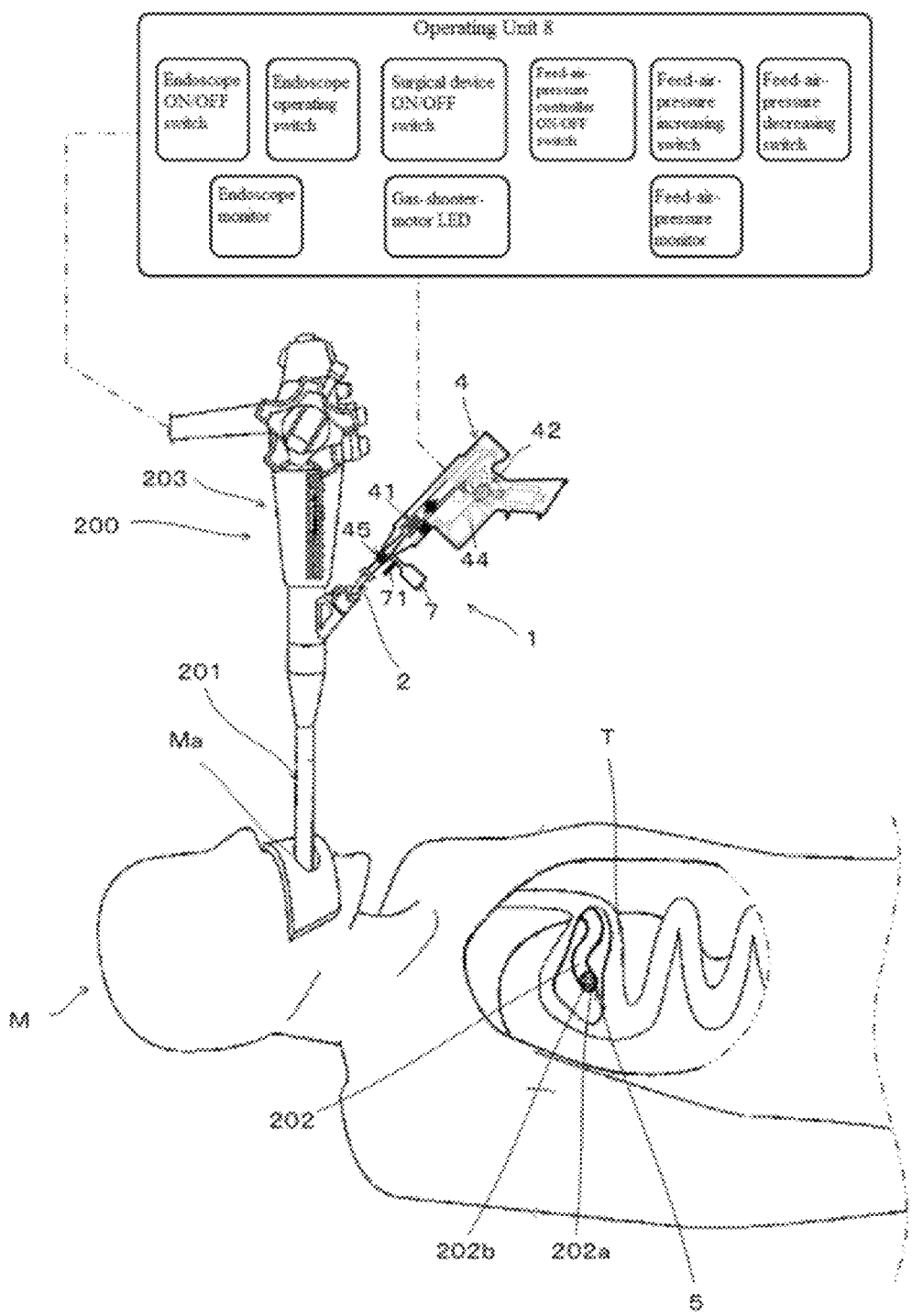
FIG. 1 is a conceptual diagram showing the main structural concept of a surgical system according to a preferred embodiment (first embodiment) of the present invention for small-pit closure in hollow organs.

As shown in FIG. 1, the surgical system for small-pit closure in hollow organs according to one mode for carrying out the invention (a first embodiment) includes: (1) a surgical device 1 for small-pit closure in hollow organs that is inserted via the mouth or other natural orifice Ma of a body M, such as a human body, through a first operating channel 202a of an endoscope 200 into a hollow organ T having a small pit Tc, so as to suture tissue at the site of the small pit Tc from within the hollow organ T; and (2) an operating unit 8 that controls and monitors operations of the endoscope 200 and surgical device 1.

Figure 2:
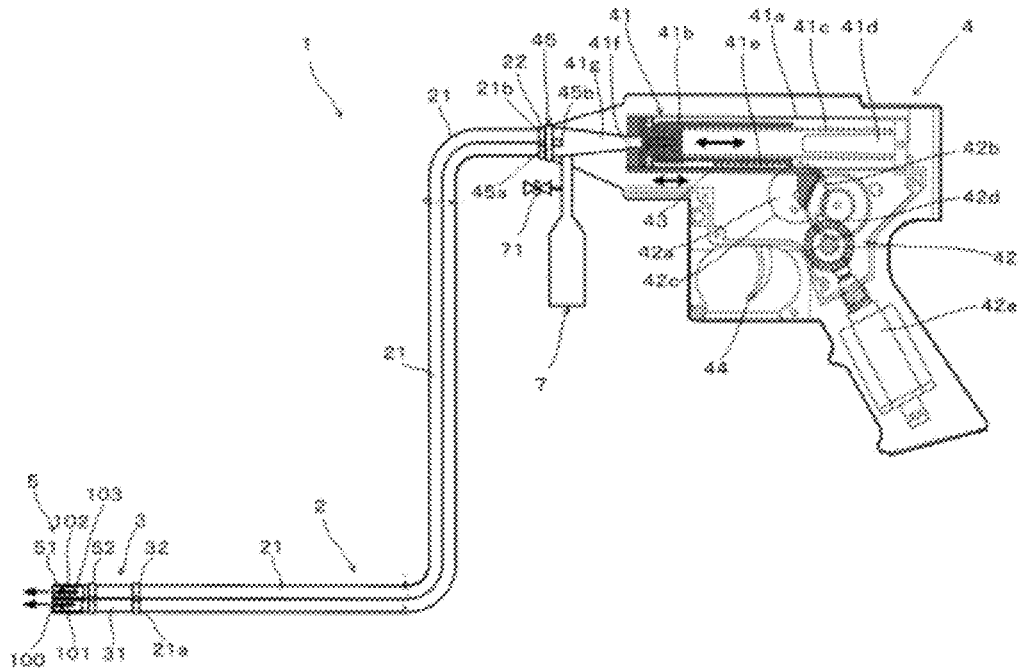
FIG. 2 is a transparent view showing the main structural concept of the surgical device according to the first embodiment.
Figure 3:
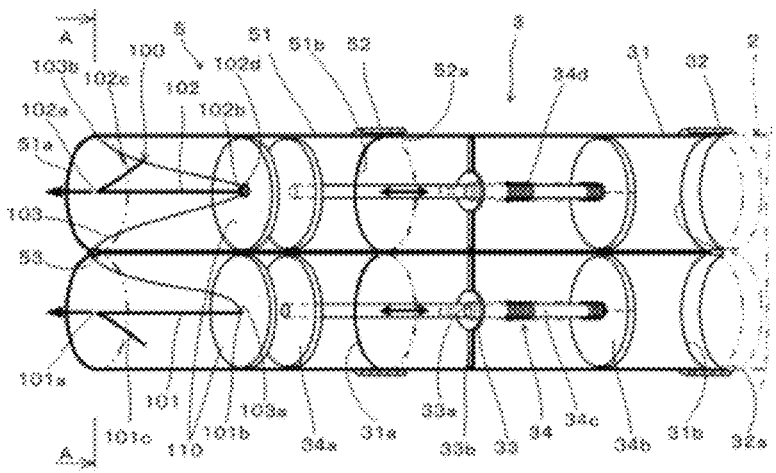
FIG. 3(*a*) is a vertical cross-sectional view showing the structure of the suture-member cartridge shown in FIG. 2.
Figure 3:
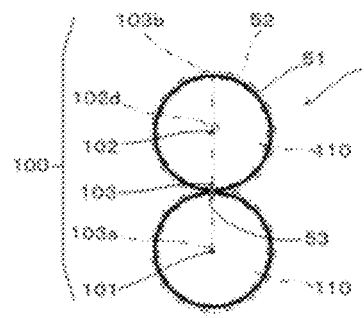

As shown in FIGS. 1 through 3, the surgical device 1 of the first embodiment is generally configured of: (1) a suture member 100 that includes (a) at least one pair of first and second arrowy-shaped members 101 and 102 having respective engaging parts 101c and 102c that engage with tissue in a hollow organ, and (b) a suture thread 103 that is attached by one of its ends (first end) 103a to the rear end 101b of the first arrowy-shaped member 101, for example, then inserted into and pulled freely through the rear end 102b of the second arrowy-shaped member 102, for example, and then fixed by its other end (second end) 103b to the inner surface of the leading end 51a of a tubular member 51 of a suture-member cartridge 5 described later; and, beginning from the leading-end side of the device; (2) a suture-member cartridge 5, in which a pair of tubular members 51 are integrally coupled in parallel, with the suture thread 103 inserted through a small opening 53 formed at the leading end in the coupled portion of the tubular members 51, and with the first and second arrowy-shaped members 101 and 102 respectively accommodated in the respective tubular members 51; (3) an auxiliary shooting unit 3, which includes (a) a pair of cylinders 31 that are open at both ends and coupled together in parallel and coupled to the rear ends of the pair of respective tubular members 51, and (b) a pair of plungers 34 accommodated in the respective cylinders 31 that move freely forward and rearward in the cylinders 31 while maintaining a hermetic seal with the cylinders 31; (4) a hollow-organ-insertable unit 2 that includes a pair of flexible air tubes 21 that are coupled together in parallel and are respectively coupled to the rear ends of the pair of cylinders 31; and (5) a gas shooter 4 that is coupled to the rear end of the hollow-organ-insertable unit 2 in which a piston 41b of a 41 gas cylinder is driven in the retracting direction by a motor 42e, storing energy in a compression spring 41c, with said piston 41b advancing rapidly when the actuation of the motor 42e is controlled through operation of a trigger 44, for example, generating compressed air that is sequentially ejected into the pair of cylinders 31 of the auxiliary shooting unit 3.

The gas shooter 4 of the first embodiment is not limited to the structure shown in the example of FIG. 2 and the like, but can have a structure almost identical to one of the various structures for electric guns or air guns known in the art. The example in FIG. 2 and the like will be only briefly described below, without going into detail.

As shown in FIG. 2, the cylinder 41a of the 41 gas cylinder has a compressed air ejection hole 41f at the leading end thereof and is disposed coaxially and rearward of a nozzle 41g that is equivalent to the barrel of an electric air gun. The piston 41b is inserted through an opening in the rear end of the cylinder 41a and can advance and retract therein. A sealing member, such as an O-ring (not shown) is provided on the front end of the piston 41b for maintaining an airtight seal with the inner wall of the cylinder 41a as the piston 41b slides. The compression spring 41c, which stores energy when the piston 41b is retracted, has one end attached to the piston 41b and its other end attached to the base part of a spindle 41d, which is fixed to the body of the gas shooter 4. The compression spring 41c possesses a strong restoring force for pushing the piston 41b instantly and rapidly when the stored energy is released. Further, a tappet 43 is provided for driving, for example, a feed-air switching mechanism 45 (described later). The tappet 43 has on its front end a cylinder part (not shown) that is slidably inserted into the periphery of the ejection hole 41f, and has on its rear end a downward-facing engaging part (not shown) that is engaged with a tappet pin (not shown) on a drive mechanism 42 and that can recede only the distance required for driving the feed-air switching mechanism 45 to switch air feeds. The erect front portion of the tappet 43 is constantly urged by a spring (not shown) to contact the front wall of the cylinder 41a.

In order to drive the piston with the drive mechanism 42, multiple rack teeth 41e are provided along the bottom surface of the piston 41b along the direction that the piston 41b moves, with the tooth at the front end formed larger than the other rack teeth so as to reliably mesh with a sector gear 42a. The sector gear 42a has a tooth portion 42b, and a toothless portion 42c that has a diameter small enough to prevent the sector gear 42a from engaging the rack teeth 41e and moving the piston 41b. That is, the rack teeth 41e are provided over the length required to retract the piston 41b exactly one stroke, and the piston 41b is retracted by the rotating sector gear 42a as the sector gear 42a is enmeshed with the rack teeth 41e from the beginning to the end of the tooth portion 42b. The sector gear 42a having this construction is linked to the motor 42e through a transmission-gear mechanism 42d configured of a set of reduction gears. A backstop mechanism (not shown) is also provided.

The sector gear 42a has a cam (not shown) provided coaxially therewith. The cam is engaged with a cutoff-detection switch and is configured to switch the cutoff-detection switch through this engagement. Specifically, the cutoff-detection switch has a pivoting member, against which the cam slides, and a movable portion.

A trigger-detection switch (also not shown in the drawings) is disposed near the trigger 44. The trigger-detection switch has a movable portion and is configured to switch when this movable portion is pressed directly by the operating part of the trigger 44. When the trigger 44 ceases to be operated, a spring (not shown) urges the trigger 44 back to a standby position.

A power supply (not shown) of any type can be provided in the gas shooter 4, but a rechargeable battery is most suitable for the gas shooter 4 from the perspectives of operability, ease of handling, and the like.

The gas shooter 4 having the above construction is operated as follows.

When the trigger 44 is pulled, the trigger-detection switch (not shown), which is positioned to engage with the trigger 44, transmits a signal current to a semiconductor controller, switching the controller so that power is supplied from the power supply to the motor 42e. The motor 42e begins to rotate, activating the drive mechanism 42. Consequently, the sector gear 42a begins rotating and the piston 41b begins retracting when the tooth portion 42b of the sector gear 42a engages with the rack teeth 41e.

The piston 41b continues to retract as the sector gear 42a rotates further. However, when the piston 41b arrives at a fixed position equivalent to the limit of its retraction, the cam (not shown), which is rotating coaxially with the sector gear 42a, slides against the pivoting member of the cutoff-detection switch and presses the movable portion of that switch, turning on the cutoff-detection switch so that the signal current is supplied to the semiconductor controller.

In the stage described above, the tappet pin (not shown in the drawings) provided on the sector gear 42a engages with the engaging part of the tappet 43, temporarily retracting the tappet 43 so as to drive the feed-air switching mechanism 45 to switch to its home position. The feed-air switching mechanism 45 is held in its home position through driving means (not shown) operated by the advance of the tappet 43.

Although not shown in the drawings, the semiconductor controller is switched by the detection of a cutoff signal, interrupting the power supply to the motor 42e. After the power supply is interrupted, the motor 42e continues to rotate by its inertia, but gradually halts. During this time, the piston 41b continues to be retracted until the tooth portion 42b of the sector gear 42a becomes disengaged from the rack teeth 41e of the piston 41b. As a result, the elastic force of the compressed compression spring 41c propels the piston 41b forward instantaneously and rapidly, generating compressed air in the cylinder 41a, with said compressed air being discharged through the ejection hole 41f into the nozzle 41g side.

At this point, the semiconductor controller is in an off state, the piston 41b is in an advanced position, and all interrelated parts have returned to their home positions; this is a state in which preparations for shooting are complete.

The force (pressure) of compressed air ejected through the ejection hole 41f can be adjusted by varying the elastic force of the compression spring 41c, and the pressure of the compressed air discharged through the nozzle 41g can be adjusted to a desired magnitude by a feed-air-pressure controller 7 that branches to and communicates with the nozzle 41g, for example. The feed-air-pressure controller 7 can easily adjust the pressure of compressed air discharged through the nozzle 41g to a desired magnitude by a pressure-regulating valve 71 that is provided for branching to and communicating with the nozzle 41g.

When in this way using the gas shooter 4 that is provided with a single compression spring 41c having a suitable elastic force, the feed-air-pressure controller 7 can easily adjust the pressure of the compressed air to a desired magnitude according to circumstances relating to the tissue at the small-pit site in the hollow organ T, the type and size of the first and second arrowy-shaped member 101 and 102, and the like.

As shown in FIG. 2, the feed-air switching mechanism 45 is interposed between the leading end of the nozzle 41g in the gas shooter 4 and the rear end 21b on the air tube 21 in the hollow-organ-insertable unit 2 in order to sequentially switch between a circulation state for supplying compressed air discharged from the gas shooter 4 and a non-circulation state for each air tube 21 in the hollow-organ-insertable unit 2. The rear end 21b of the air tube 21 is coupled to the feed-air switching mechanism 45 via a coupling tube 22.

Figure 4:
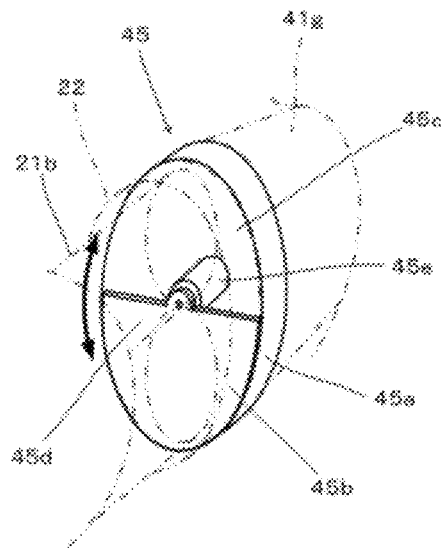
FIG. 4 is a perspective view showing the structural concept of the feed-air switching mechanism shown in FIG. 2.

As shown in FIG. 4, the feed-air switching mechanism 45 includes (1) a switching plate 45b that is rotatably supported inside a case 45a adjacent to the rear end 21b of each air tube 21, and (2) driving means 45e provided for rotating the switching plate 45b so as to switch the circulation state through an 45c and the non-circulation state by a shielding part 45d between the two positions.

The driving means 45e can be configured of a drive source, such as a link-and-crank-gear mechanism or a solenoid (not shown) well known in the art, operated by the advancing and retracting of the tappet 43 in association with the trigger 44 of the gas shooter 4 each time the trigger 44 is pulled. The switching plate 45b rotates each time the trigger 44 is pulled in order to switch the circulation state for sequentially supplying compressed air to the air tubes 21 of the hollow-organ-insertable unit 2 that communicate with the tubes 51 of the suture-member cartridge 5 that respectively accommodate the first and second arrowy-shaped members 101 and 102.

As shown in FIGS. 3(a) and 3(b), the suture-member cartridge 5 is open both on the leading end 51a and on the rear end 51b. The suture-member cartridge 5 accommodates the first and second arrowy-shaped members 101 and 102, whose rear ends 101b and 102b are linked by the suture thread 103, in the pair of integrally coupled and parallel tubular members 51; and partitioning members 110 that (a) are generally shaped like discs or short cylinders and formed of a cellulose or other material that is biocompatible with the hollow organ and that is either digestible or soluble or at least capable of being discharged from the body, and (b) freely slide in or near the rear ends 101b and 102b of the first and second arrowy-shaped members 101 and 102 in a generally hermetic state therewith. A coupling tube 52 is fitted around the outer surface of the tubular members 51 on the rear ends 51b thereof, with the leading-end of the auxiliary shooting unit 3 inserted into and coupled with the coupling tube 52.

The compressed air discharged from the gas shooter 4 via the auxiliary shooting unit 3 is received fully by the generally disc-shaped or short-cylinder-shaped partitioning members 110 and reliably ejects, one after the other, the first and second arrowy-shaped members 101 and 102, comprising linear, rod-like, or strip-like bodies.

The first and second arrowy-shaped members 101 and 102 according to the first embodiment are formed of a corrosion-resistant metal, such as stainless steel or titanium, or a suitable medically-compatible material that is harmless to and assimilable by living tissue. The first and second arrowy-shaped members 101 and 102 can each be configured of a linear, rod-like, or strip-like (not shown) body having the same general shape and having the engaging parts 101c and 102c, respectively formed on or near respective leading ends 101a and 102a, for latching onto tissue in the hollow organ T. The engaging parts 101c and 102c are elastic and angle outward toward the rear in a hook-like shape.

With their slender linear, rod-like, or strip-like shape, the first and second arrowy-shaped members 101 and 102 of the preferred embodiment readily enter tissue in the hollow organ when ejected, thereby reducing discomfort for the patient.

A suture-thread-insertion part 102d having a type of ratchet mechanism is provided on the rear end 102b of the second arrowy-shaped member 102. As shown in the example of FIGS. 10(a)-10(c), the suture thread 103 that is inserted through the suture-thread-insertion part 102d can be freely pulled outward in the withdrawal direction as the diameter of the insertion hole 102d4 (FIG. 10(b)) expands, but is restricted from being pulled back in a return direction as the diameter of the insertion hole 102d4 decreases (FIG. 10(c)).

The suture-thread-insertion part 102d includes a generally-annular outer frame 102d1 that is fixed to the rear end 102b of the second arrowy-shaped member 102, an inner frame 102d3 in which the generally circular insertion hole 102d4 is formed, and an elastic support member 102d2 that is generally disc-shaped, for example, is flexible, and is provided between the outer frame 102d1 and inner frame 102d3. The suture-thread-insertion part 102d is configured with multiple slit parts 102d5 formed radially to positions in the elastic support member 102d2 or inner frame 102d3 so that the elastic support member 102d2 easily deforms, and the insertion hole 102d4 easily expands or shrinks in diameter.

Hence, the rear ends 101b and 102b of the first and second arrowy-shaped members 101 and 102 that have been driven into the tissue in the hollow organ T around the site of the small pit Tc can be drawn together simply by pulling out the suture thread 103, while the suture thread 103 is prevented from slipping backward. Thus, the tissue in the hollow organ T around the small pit Tc site can be quickly closed through one simple operation and held in a sutured state.

The auxiliary shooting unit 3 includes (1) a pair of cylinders 31 integrally coupled together in parallel and respectively coupled to the rear ends 51b of the tubular members 51 in the suture-member cartridge 5 by the inner surface 52a of the coupling tube 52 through insertion into the coupling tube 52; and (2) a pair of plungers 34 respectively accommodated in the respective cylinders 31 and capable of moving freely forward and rearward while maintaining hermetic contact with the cylinders 31.

Each of the plungers 34 has front and rear plunger parts 34a and 34b, whose center portions are coupled by a coupling shaft 34c. The coupling shaft 34c is slidably inserted through a through-hole 33a formed in the center of a plunger support 33 that is fixed to the inner surface of the cylinder 31 through a fixed frame 33b. A return spring 34d configured of a compression spring is fitted around the coupling shaft 34c and interposed between the plunger support 33 and the rear plunger part 34b.

Hence, the plungers 34 are constantly urged in the retracting direction by the elastic force of the return springs 34d. When compressed air is released from the gas shooter 4 toward one of the plungers 34, the plunger 34 overcomes the urging force of the return spring 34d and advances rapidly, generating secondary compressed air in the suture-member cartridge 5. The secondary compressed air strikes the nearby partitioning member 110, ejecting the first or second arrowy-shaped member 101 or 102 from the opening in the leading end 51a of the tubular member 51 toward the tissue in the hollow organ T. The first or second arrowy-shaped member 101 or 102 is ejected in this way from the suture-member cartridge 5 by the compressed air according to the principle of a blowgun. After one emission of compressed air from the gas shooter 4 is completed, causing one arrowy-shaped member to be ejected, the plunger 34 is returned to its home position, that is, its starting point, by the elastic force of the return spring 34d. By repeating the above operation, both the first and second arrowy-shaped members 101 and 102 are sequentially ejected from the suture-member cartridge 5.

As illustrated conceptually in FIG. 1, the operating unit 8 according to the first embodiment includes at least an endoscope monitor, a feed-air pressure monitor, a surgical device ON/OFF switch (a power switch for the surgical device 1), a gas shooter motor LED (an operation-indicating lamp for the motor 42e), an endoscope ON/OFF switch (a switch for operating the endoscope 200), an endoscope operating switch (a switch for a solenoid valve or the like in the endoscope 200), a feed-air-pressure controller ON/OFF switch (a power switch for the feed-air-pressure controller 7), a feed-air pressure increasing switch, and a feed-air pressure decreasing switch. Although not shown in the drawings, the operating unit 8 further includes a transceiver and image-processing unit for the endoscope 200.

Next, a method for suturing tissue in a hollow organ T, such as a stomach around the site of a small pit Tc, using the surgical system for small-pit closure in hollow organs of the first embodiment described above, including the surgical device 1, endoscope 200, and operating unit 8, will be described with reference to FIGS. 1 through 10, 15, and the like.

The surgical method of the first embodiment for suture closure of small pit in hollow organs has the following main steps when the hollow organ is a stomach T in a human body M or other living body and when suturing tissue that includes a mucosa Tb and submucosa Ta in the site of a small pit Tc.

First, the leading end of the suture-member cartridge 5 and the auxiliary shooting unit 3 attached to the leading end of the hollow-organ-insertable unit 2 are inserted into the first operating channel 202*a* of the endoscope 200, for example, and the leading-end 202 of the endoscope 200 is inserted into the stomach T to a position near the site of the small pit Tc, which has been identified through various procedures and diagnostics (Step 1S: inserting endoscope into hollow organ).

From inside the stomach T, the endoscope 200 is used to observe and confirm the site of the small pit Tc in the stomach T (Step 2S: confirming small pit in hollow organ). Surgical procedures for small-pit closure in all subsequent steps are performed cautiously while carefully observing and confirming the site of the small pit Tc in the stomach T through the various monitors, operation-indicating LEDs, and the like on the endoscope 200 and operating unit 8.

After confirming the small pit in the hollow organ, the pressure of compressed air to be discharged from the gas shooter 4 is set to a desired magnitude using the feed-air-pressure controller 7, based on conditions relating to the tissue around the small pit Tc, the type and size of the suture member 100, and the like (Step 11S: setting feed-air pressure).

Figure 5:
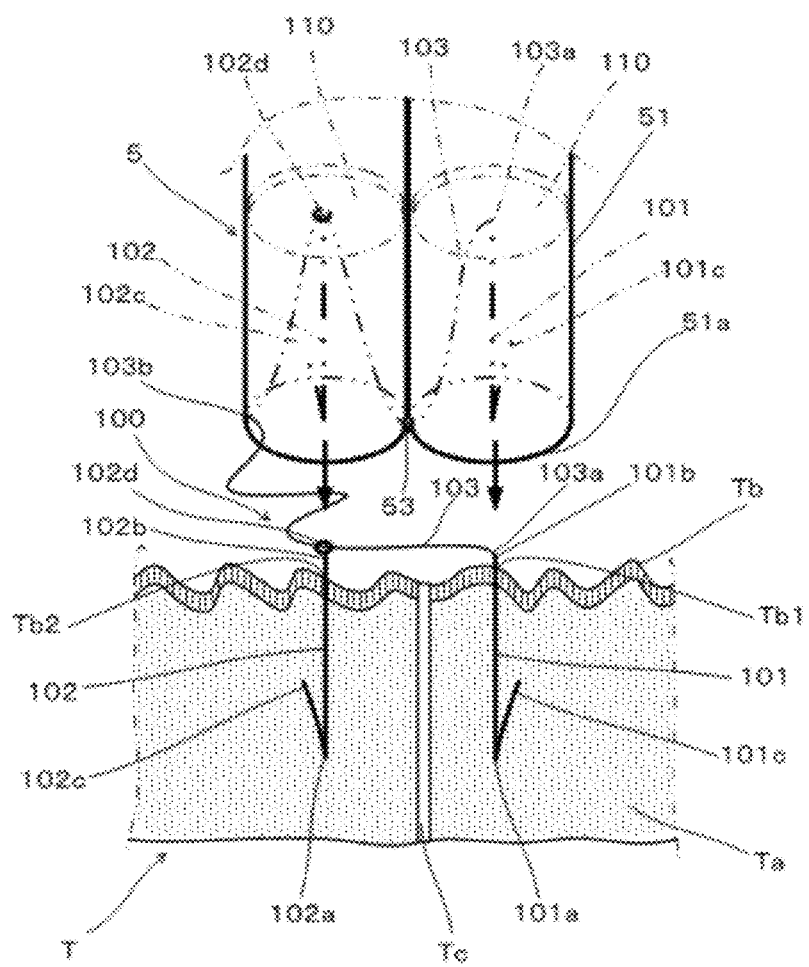
FIG. 5 is a vertical cross-sectional view in which the pair of arrowy-shaped members shown in FIG. 2 are embedded in hollow-organ tissue at a small-pit site.

Next, with the suture-member cartridge 5 protruding a suitable distance from the leading-end 202 of the endoscope 200, the leading-end 202 and the leading end 51*a* of the suture-member cartridge 5 on the side of the tubular member 51 accommodating the first arrowy-shaped member 101 are moved to a prescribed distance from the surface of the mucosa Tb at a first position Tb1 near the small pit Tc (Step 12S: placing leading end of suture-member cartridge in first position; see FIG. 5).

The trigger 44 of the gas shooter 4 is then pulled so as to eject the first arrowy-shaped member 101 toward the first position Tb1 (Step 13S: ejecting first arrowy-shaped member). As a result, the first arrowy-shaped member 101 is driven into the submucosa Ta near the first position Tb1, as shown in FIG. 5.

Next, the leading-end 202 of the endoscope 200 and the leading end 51*a* of the suture-member cartridge 5 on the side of the tubular member 51 accommodating the second arrowy-shaped member 102 are moved and placed a prescribed distance from the surface of the mucosa Tb at a second position Tb2 near the small pit Tc on the side opposite the first position Tb1 (Step 14S: placing leading end of suture-member cartridge in second position; see FIG. 5).

The trigger 44 of the gas shooter 4 is again pulled, so as to eject the second arrowy-shaped member 102 toward the second position Tb2 (Step 15S: ejecting second arrowy-shaped member). As a result, the second arrowy-shaped member 102 is driven into the submucosa Ta near the second position Tb2, as shown in FIG. 5. When both the first and second arrowy-shaped member 101 and 102 are ejected, the midway portion of the suture thread 103 that was inserted into the small opening 53 formed at the leading end of the suture-member cartridge 5 in the coupled part of the tubular members 51 separates from the small opening 53. Although the first and second arrowy-shaped members 101 and 102 are driven such that a portion of the leading ends 101*a* and 102*a* pierce the submucosa Ta at this time, this is not particularly problematic.

Figure 6:
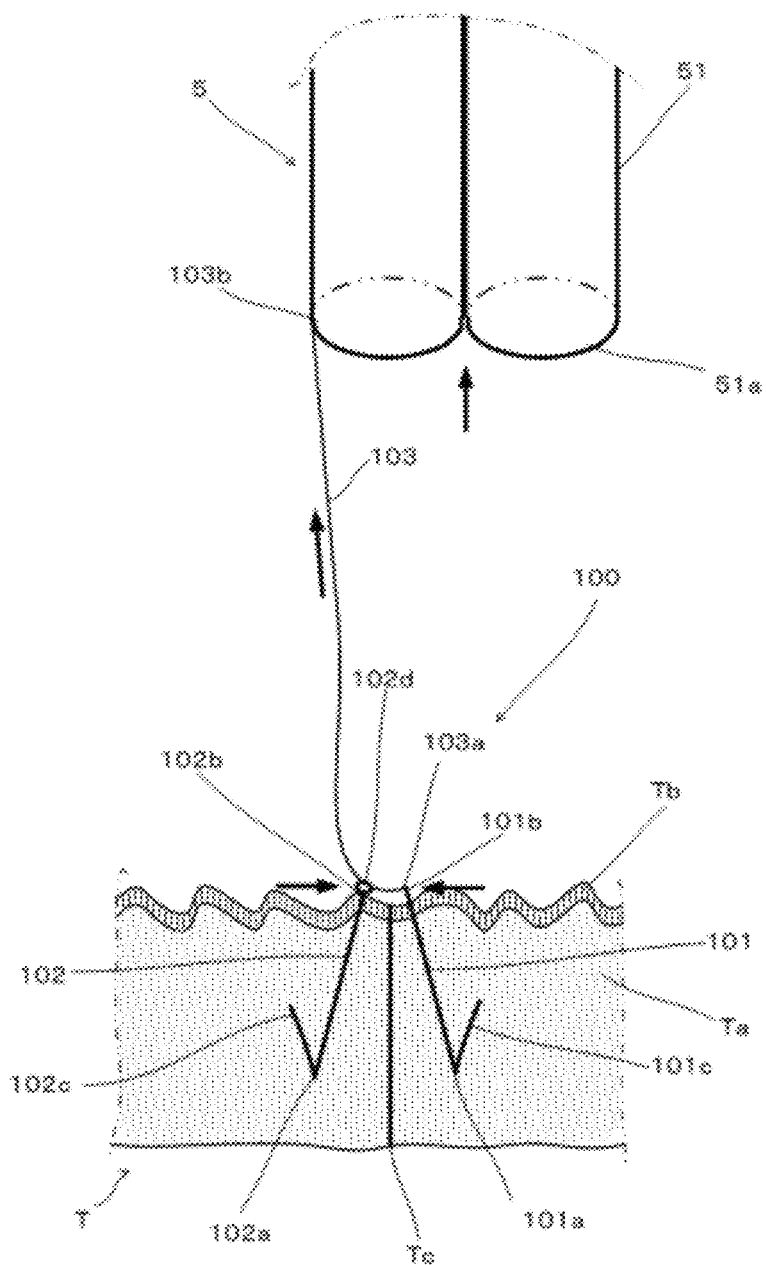
FIG. 6 is a vertical cross-sectional view illustrating a step for stitching the small-pit site as a continuation of the state shown in FIG. 5.

The surgical device 1 is then retracted (pulled outward) while the endoscope 200 is used to monitor the embedded states of the first and second arrowy-shaped members 101 and 102. By retracting the surgical device 1, the suture thread whose second end 103*b* is fixed inside the leading end 51*a* of the tubular member 51, draws the rear end 101*b* of the first arrowy-shaped member 101 on which the suture thread's first end 103*a* is fixed toward the rear end 102*b* of the second arrowy-shaped member 102, as shown in FIG. 6, thereby forming a tight suture in the tissue around the small pit Tc (Step 16S: stitching small-pit site).

Here, with the ratchet mechanism of the suture-thread-insertion part 102*d* that is provided at the rear end 102*b* of the second arrowy-shaped member 102 allowing the suture thread 103 that has been inserted through the suture-thread-insertion part 102*d* to be pulled outward in the withdrawal direction due to the expansion of the diameter of the insertion hole 102*d*4 (FIG. 10(*b*)) while restricting the suture thread 103 from slipping backward in the return direction due to the decreasing diameter of the insertion hole 102*d*4 (FIG. 10(*c*)), the rear ends 101*b* and 102*b* of the first and second arrowy-shaped members 101 and 102 that are embedded in the tissue around the small pit Tc can be drawn together simply by pulling the suture thread 103 outward, with the suture thread 103 also being locked and prevented from slipping backward. Thus, in one motion, the tissue in the stomach T around the small pit Tc can be brought together and held in a sutured state.

The pulled suture thread 103 is cut near the rear end 102*b* of the second arrowy-shaped member 102 by an endoscopic tool (not shown) in a second operating channel 202*b* of the endoscope 200, for example (Step 3S: cutting suture thread). After the suture thread 103 is cut, the first and second arrowy-shaped members 101 and 102 remain in the tissue of the stomach T with the tissue around the small pit Tc closed.

Once the suture thread has been cut, the surgical device 1 is extracted from the mouth Ma of the human body M together with the endoscope 200, completing one operation for small-pit closure in a hollow organ (Step 4S: extracting endoscope from body).

There are other modes for implementing the suture member of the present invention that differ from the suture member 100 according to the first embodiment described above, some of which will be described below.

Figure 7:
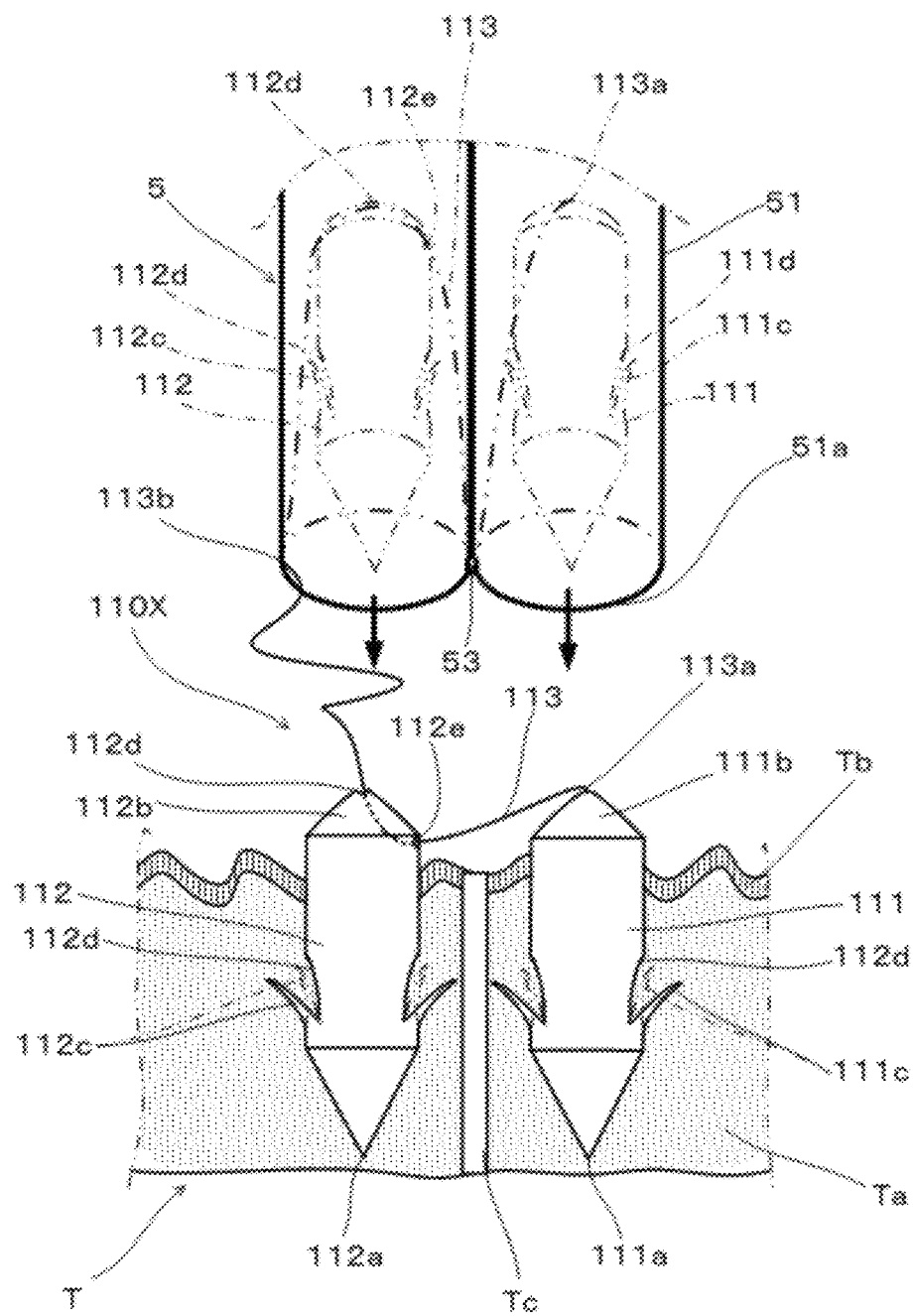
FIG. 7 is a vertical cross-sectional view showing arrowy-shaped members embedded in hollow-organ tissue at a small-pit site according to another implementation mode of the present invention.

As shown in FIG. 7, a suture member 110X according to a different mode for carrying out the present invention includes: (1) first and second arrowy-shaped members 111 and 112 that are configured of generally round bar-shaped or cylindrical bodies of substantially the same shape, and that have (a) respective leading ends 111*a* and 112*a* that are formed in sharp points, (b) side surfaces adjacent to and extending rearward from each of the leading ends 111*a* and 112*a*, and (c) engaging parts 111*c* and 112*c* that are cut and spread outward from the respective side surfaces to form elastic, angled hook-like members for latching onto tissue in the stomach T; and (2) a suture thread 113 that is attached by one of its ends (first end) 113*a* to, for example, the rear end 111*b* of the first arrowy-shaped member 111, and is then inserted into and pulled freely through an insertion hole 112*e* and a suture-thread-insertion part 112*d* that communicates with the insertion hole 112*e* and is provided, for example, in the side surface of the second arrowy-shaped member 112 near the rear end 112*b* of the second arrowy-shaped member 112 and fixed by the other end (second end) 113*b* of the suture thread 113 to the inner surface of the leading end 51*a* of the tubular member 51 in the suture-member cartridge 5.

While not shown in the drawings, a ratchet mechanism similar to the suture-thread-insertion part 102*d* of FIG. 10 in the suture member 100 according to the first embodiment is provided on the suture-thread-insertion part 112*d* for allowing the suture thread 113 to be drawn outward but restricting its return.

While the first and second arrowy-shaped members 111 and 112 are depicted in FIG. 7 to be considerably narrower than the inner diameters of the tubular members 51, in reality the first and second arrowy-shaped members 111 and 112 are formed only slightly narrower than the inner diameters of the tubular members 51. Accordingly, the first and second arrowy-shaped members 101 and 102, which have round bar-shaped or cylindrical bodies, can fully receive the compressed air discharged from the gas shooter 4 via the auxiliary shooting unit 3 and can smoothly and reliably be ejected one after the other, thereby eliminating the need for the generally disc-shaped or short-cylinder-shaped partitioning members 110 shown in FIG. 3 of the first embodiment. Alternatively, the round bar-shaped or cylindrical bodies can be replaced with generally conical bodies.

Therefore, excluding the difference in the shape of the first and second arrowy-shaped members 111 and 112, the suture member 110X according to the modified implementation mode of the invention can perform nearly the same process shown in FIGS. 5 and 6 with the suture member 100 according to the first embodiment for driving the first and second arrowy-shaped members 111 and 112 into the tissue of the hollow organ T and suturing tissue around the small pit Tc.

Figure 8:
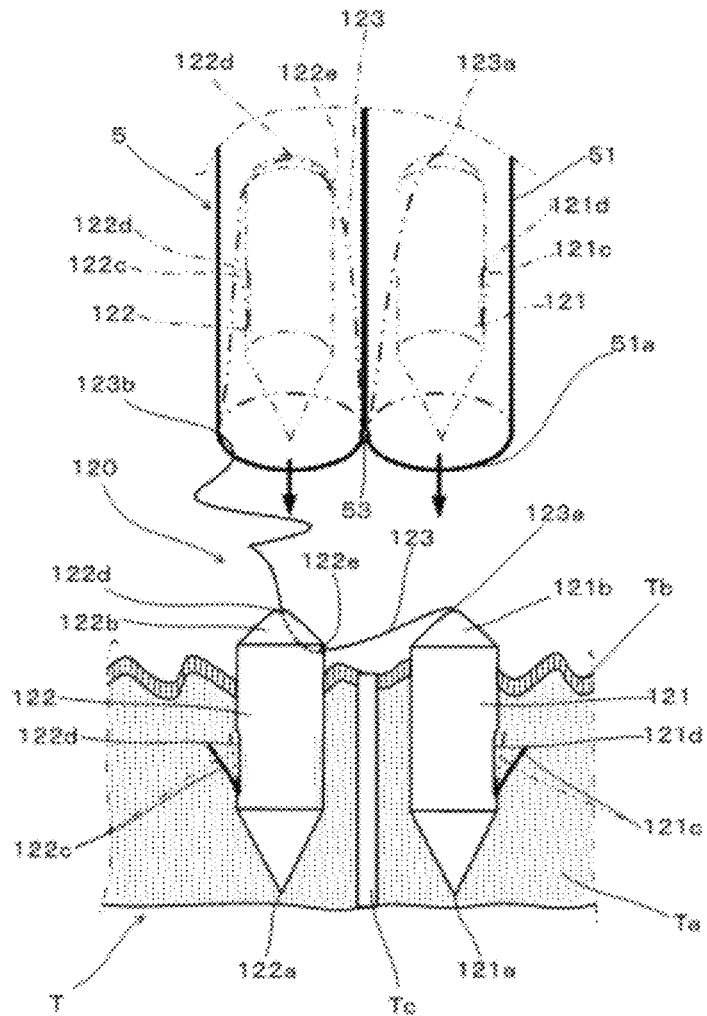
FIG. 8 is a vertical cross-sectional view showing arrowy-shaped members embedded in hollow-organ tissue at a small-pit site according to another implementation mode of the present invention.

As shown in FIG. 8, a suture member 120 according to another mode for carrying out the invention is identical to the suture member 110X of the implementation mode described above, except that a side surface on each of first and second arrowy-shaped members 121 and 122, which have generally round bar-shaped or cylindrical bodies (or generally conical bodies, not shown), is partially cut to form respective notch parts 121*d* and 122*d*, and engaging parts 121*c* and 122*c* are formed by fixing one end of a linear or strip-like body to each of the notch parts 121*d* and 122*d*.

Due to their slender linear or strip-like shape, the engaging parts 121*c* and 122*c* of the first and second arrowy-shaped members 121 and 122 according to the present implementation mode of the invention can easily enter and engage with tissue in the hollow organ T, thereby reducing discomfort to the patient.

Further, because the first and second arrowy-shaped members 111 and 112 and first and second arrowy-shaped members 121 and 122 of the hollow-organ-insertable unit 2 modified modes described above are configured of generally round bar-shaped or cylindrical bodies or generally conical bodies (not shown), the arrowy-shaped members themselves receive the full impact of compressed air discharged from the gas shooter via the auxiliary shooting unit and are smoothly and reliably ejected one after the other, and in particular can easily ensure hemostasis owing to their solid form and, therefore, are applicable to patients with unusual conditions, such as hemorrhaging tendencies, myocardial infarction, cerebral infarction, and cirrhosis, and to patients having prosthetic valves.

Figure 9:
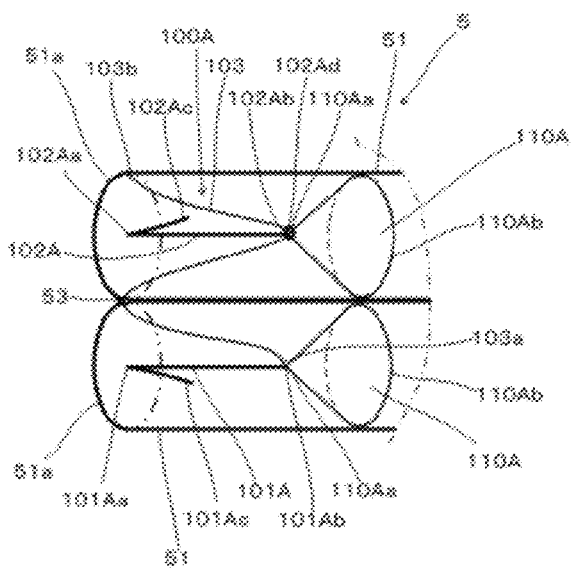
FIG. 9 is a vertical cross-sectional view showing a suture member according to another implementation mode of the present invention.

As shown in FIG. 9, a suture member 100A according to yet another mode for carrying out the invention is identical to the suture member 100 according to the first embodiment, except for vanes 110A that are provided on the rear ends 101Ab and 102Ab of the first and second arrowy-shaped members 101A and 102A. The vanes 110A are (a) formed of a film-like biocompatible material that is either digestible or soluble or at least capable of being discharged from the body, (b) are generally conical-shaped, expanding outward from their leading ends 110Aa to their rear ends 110Ab, and (c) are freely slidable in the tubular members 51 while maintaining a generally hermetic state therewith.

The leading ends 110Aa of the vanes 110A are respectively fixed to the rear ends of the first and second arrowy-shaped members 101A and 102A, while the rear ends 110Ab are generally circular or short-cylinder shaped (not shown) and are slidably held by the inner surfaces of the tubular members 51 in a generally hermetic state. Accordingly, the compressed air discharged from the gas shooter 4 via the auxiliary shooting unit 3 is received fully by the generally conical-shaped vanes 110A and can—in a manner similar to a blowgun—reliably eject, one after the other, the first and second arrowy-shaped members 101A and 102A, comprising slender linear, rod-like, or strip-like bodies.

There are other modes for implementing the suture-member cartridge of the present invention that differ from the suture-member cartridge 5 according to the first embodiment described above, some of which will be described below.

Although the suture-member cartridge 5 according to the first embodiment has one pair of tubular members 51 arranged parallel to each other, a suture-member cartridge 5A according to another mode for implementing the present invention is integrally provided with multiple pairs of the tubular members 51 and, as shown in FIG. 11, two pairs, or four tubular members 51, coupled in parallel. As in the first embodiment described above, each pair of the tubular members 51 accommodates the first and second arrowy-shaped members 101 and 102, which are linked at their rear ends 101*b* and 102*b* by the suture thread 103, and the partitioning members 110 are generally shaped like discs or short cylinders or generally conical vanes and are hermetically and slidably retained in or near the rear ends 101*b* and 102*b* of the first and second arrowy-shaped members 101 and 102.

In the current mode for implementing the invention, therefore, the suture-member cartridge 5A is coupled to multiple pairs (two pairs each in this example) of the auxiliary shooting units and hollow-organ-insertable units (not shown) having four each of cylinders and air tubes integrally coupled in parallel. As shown in FIG. 12, a feed-air switching mechanism 45A interposed between a coupling tube 22A on the rear end of the hollow-organ-insertable units and the nozzle 41*g* of the gas shooter includes a switching plate 45Ab that is rotatably supported inside a case 45Aa and that has a single circular opening 45Ac for producing a circulation state, and a driving means 45Ae for rotating the switching plate 45Ab so as to switch the position for the circulation state, in which compressed air is supplied sequentially to each of the four air tubes in the hollow-organ-insertable unit, and the position of the non-circulation state achieved by a shielding part 45Ad.

Because multiple suture members 100 are ejected from the suture-member cartridge 5A having multiple pairs of tubular members 51, multiple sutures can be quickly formed in tissue around the small pit Tc site by inserting the surgical device into the hollow organ T just one time, thereby further reducing the duration and invasiveness of surgery, improving the efficiency of small-pit closure surgery in a hollow organ, and reducing pain and discomfort to the patient.

As shown in FIG. 13, a suture-member cartridge 5B according to another mode for carrying out the present invention is longer than the suture-member cartridge according to the first embodiment and has (1) a pair of tubular members 51B, (2) a small opening that penetrates the coupled portion of the tubular members 51B over a prescribed length from the leading end of the coupled portion for inserting the suture threads 103, and (3) multiple pairs of first and second arrowy-shaped members 101 and 102 arranged in series at substantially regular intervals and accommodated in the tubular members 51B. In this case, the second end 103b of each suture thread 103 is fixed to the inner surface of the tubular member 51B near the leading end 102a of the respective second arrowy-shaped member 102, and the length of the suture threads 103 is set increasingly longer for each suture member 100 positioned farther rearward in the tubular members 51B in order that the respective first and second arrowy-shaped members 101 and 102 can reliably reach and become embedded in the tissue around the target small pit Tc site.

An auxiliary shooting unit 3B is coupled via the coupling tubular member 52 to the rear end 51Bb of the tubular members 51B in the suture-member cartridge 5B according to the current mode for implementing the invention and has a double-cylinder structure that includes a pair of open-ended cylinders 31B and inner cylinders 35 in the cylinders 31B so as to be capable of moving forward and rearward, with the inner cylinders 35 themselves accommodating a pair of plungers 34B that move freely forward and rearward while maintaining a hermetic seal with the inner cylinders 35.

As with the plungers 34 according to the first embodiment described above, each of the plungers 34B has front and rear plunger parts 34Bc and 34Bb, whose center portions are coupled by a coupling shaft 34Bc. The coupling shaft 34Bc is slidably inserted through a through-hole 33Ba in the center of a plunger support 33B that is fixed to the inner surface of the cylinder 31B. A return spring 34Bd configured of a compression spring is fitted around the coupling shaft 34Bc and interposed between the plunger support 33B and the rear plunger part 34Bb.

Hence, the plungers 34B are constantly urged in the retracting direction by the elastic force of the return springs 34Bd. When compressed air is released from the gas shooter 4 toward the plungers 34B, the plungers 34B overcome the elastic force of the return springs 34Bd and advance rapidly, generating secondary compressed air in the suture-member cartridge 5B. The secondary compressed air strikes the nearby vanes 110A, sequentially ejecting the first and second arrowy-shaped members 101A and 102A from the openings in leading ends 51Ba of the tubular members 51B toward the tissue in the hollow organ T.

In this case, the inner cylinders 35 accommodated in the plungers 34B advance one pitch P1 equivalent to the substantially regular intervals of the first and second arrowy-shaped members 101A and 102A each time one pair of the first and second arrowy-shaped members 101A and 102A is ejected, establishing a new ejection starting point. A stroke P2 for the reciprocating motion of the plungers 34B is substantially equivalent to the pitch P1 (P2≈P1) but is adjusted to a suitable stroke length based on conditions relating to the tissue of the hollow organ T around the small pit Tc, the shape of the first and second arrowy-shaped members, and the like.

Hence, because the plungers 34B advance one pitch P1 equivalent to the substantially equal intervals of the pairs of first and second arrowy-shaped members 101A and 102A each time a pair of suture members 100 is ejected to establish a new ejection starting point, compressed air generated secondarily in the suture-member cartridge 5B when the gas shooter 4 discharges compressed air can efficiently eject the first and second arrowy-shaped members 101A and 102A, thereby reliably and smoothly ejecting the first and second arrowy-shaped members 101A and 102A one after another.

Further, in the current implementation mode of the present invention, multiple suture members 100 can be accommodated in series in the suture-member cartridge 5B, having a minimum diameter, configured of one pair of tubular members 51B, which is the minimum number of pairs, and the suture members 100 are individually ejected sequentially. Hence, because multiple sutures can be formed quickly in the tissue around the small pit Tc site by inserting the surgical device into the hollow organ T just one time, it is possible to further reduce the duration and invasiveness of surgery, reduce the pain to the patient, and increase the efficiency of small-pit closure surgery in hollow organs.

Second Embodiment

A surgical system for small-pit closure in hollow organs according to a second embodiment differs in configuration from the first embodiment in that a capsule endoscope 200A is used in place of the endoscope 200; and the surgical device 1A for small-pit closure in hollow organs that is inserted directly through the mouth Ma of a human body M into a stomach T or other hollow organ having a small pit is almost identical in structure to the surgical system in the first embodiment, except that the surgical device 1A accommodates the capsule endoscope 200A at the leading end of the suture-member cartridge 5A (variation of the first embodiment), for example. Therefore, components in FIG. 14 of the second embodiment that have the same function as components in the first embodiment are assigned the same reference numerals, even when differing slightly in form, and duplicate descriptions of these components are omitted.

Next, a method of suturing tissue in a hollow organ, such as a stomach T, around the site of a small pit using the surgical system for small-pit closure in hollow organs having the surgical device 1A according to the second embodiment will be described with reference to FIGS. 14 and 16.

As shown in FIG. 16, the surgical method for small-pit closure in hollow organs according to the second embodiment of the present invention has only minor differences from the surgical method according to the first embodiment (FIG. 15) in the initial Step 10aS for inserting the surgical device into the hollow organ, in Step 2aS for confirming the small pit in the hollow organ using the capsule endoscope 200A in the leading end of the suture-member cartridge 5A, in Step 17S for cutting the suture thread after stitching the small-pit site, and in Step 18S for extracting the surgical device from the hollow organ, while all the other Steps 11S-16S are identical to the steps described in the first embodiment. Hence, only Steps 10aS, 2aS, 17S, and 18S that differ from the first embodiment will be described below.

First, the leading end of the suture-member cartridge 5A that accommodates the capsule endoscope 200A in the leading end thereof, and the auxiliary shooting unit (not shown) that is attached to the leading end of a hollow-organ-insertable unit 2A are inserted into the stomach T to a position near the small-pit site (not shown), which has been identified through various procedures and diagnostics (Step 10aS: inserting surgical device into hollow organ).

Next, the capsule endoscope 200A inside the leading end of the suture-member cartridge 5A is used to observe and confirm the site of the small pit in the stomach T (Step 2aS: confirming small pit in hollow organ). All subsequent steps in the surgical procedure for small-pit closure are performed cautiously, while carefully observing and confirming the small-pit site in the stomach T through the various monitors, operation-indicating LEDs, and the like on the capsule endoscope 200A and the operating unit 8.

After confirming the small pit in the hollow organ, the following steps are executed sequentially, as described in the first embodiment: Step 11S for setting the feed-air pressure, Step 12S for placing the leading end of the suture-member cartridge in a first position, Step 13S for ejecting the first arrowy-shaped members, Step 14S for placing the leading end of the suture-member cartridge in a second position, Step 15S for ejecting the second arrowy-shaped members, and Step 16S for stitching the small-pit site.

The pulled suture thread is cut near the suture-thread-insertion part of the second arrowy-shaped member (not shown) using a tool accommodated in an operating channel (not shown) that is provided from the hollow-organ-insertable unit 2A to the leading ends of the auxiliary shooting unit and the suture-member cartridge 5A, (Step 17S: cutting suture thread). After the suture thread has been cut, the first and second arrowy-shaped members remain in the tissue of the stomach T, with the tissue at the small-pit site closed. Although not shown in the drawings, a separate endoscope can be inserted into the stomach T after first extracting the surgical device 1A from the human body M through the mouth Ma, to cut the suture thread using an endoscope tool accommodated in one of the endoscope's operating channels.

Once the suture thread has been cut, the surgical device 1A and the capsule endoscope 200A that is in the leading end thereof are extracted from the human body M through the mouth Ma, completing one operation for small-pit closure in a hollow organ (Step 18S: extracting surgical device from hollow organ).

In the surgical method for small-pit closure in a hollow organ according to the second embodiment described above, the compact capsule endoscope 200A is used in place of the usual large endoscope 200; the hollow-organ-insertable unit 2A on which the suture-member cartridge 5A and auxiliary shooting unit are coupled on the leading end of the surgical device 1A is inserted directly through a natural orifice into the hollow organ T having a small pit; compressed air discharged from the gas shooter 4 sequentially advances the plungers in the auxiliary shooting units into which the compressed air was released, generating secondary compressed air in the suture-member cartridge 5A for sequentially ejecting the adjacent first and second arrowy-shaped members; and the rear ends of the first and second arrowy-shaped members that have been driven into the tissue in the hollow organ T on both sides of the small-pit site are drawn together via the suture thread linking the same rear ends. In this way, the tissue around the small-pit site can easily be closed and held in a sutured state through one simple and quick operation. Hence, the present invention can provide a surgical system and method for small-pit closure in hollow organs that can reduce the duration and invasiveness of surgery by eliminating the need for conventional surgical procedures, such as an abdominal incision; that can further reduce pain and discomfort to the patient; and that is excellent in operability, reliability, and safety.

With the surgical device 1 according to the first embodiment, the hollow-organ-insertable unit 2, auxiliary shooting unit 3, and suture-member cartridge 5 have an outer diameter of only about 2 mm, for example, in order to be inserted into the first operating channel 202a of the endoscope 200, for example. However, in the surgical device 1A of the second embodiment, which employs the capsule endoscope 200A in place of the usual endoscope 200, the hollow-organ-insertable unit 2A, an auxiliary shooting unit 3A, and the suture-member cartridge 5A can have larger outer diameters approximately equivalent to the outer diameter of the hollow-organ-insertable units 201 and 202 of a usual endoscope 200 or the like, thereby greatly enhancing the freedom for designing the surgical device for small-pit closure in hollow organs.

Although the surgical devices 1 and 1A for small-pit closure in hollow organs in the preferred embodiments have been described above with reference to the drawings, each member and mechanism in these surgical devices is not limited to the shape, material, configuration, and the like described in the embodiments, but can be modified as desired.

As shown in FIGS. 17(a) and 17(b), a gas shooter 4A according to another mode for carrying out the invention is provided with a high-pressure-gas reservoir 4A2a that stores high-pressure gas. Through the operation of a trigger 4A4, for example, the high-pressure gas in the high-pressure-gas reservoir 4A2a is drawn in through an ejection hole 4A1h of an ejection nozzle 4A1f in a controlled manner and released toward the nozzle 4A1g. The gas shooter 4A according to this implementation mode is not limited to the structural example shown in FIG. 17, but can be configured similar to any type of gas gun well known in the art. Therefore, the configuration shown in FIG. 17 will only be briefly described below without going into detail.

A gas-discharge valve 4A3 is provided in a gas cylinder 4A1 of the gas shooter 4A so as to close the ejection hole 4A1h when the trigger 4A4 is returned to the standby state shown in FIG. 17(a). The high-pressure-gas reservoir 4A2a is provided in the handle 4A2 and has a gas inlet 4A2b that is opened and closed by a gas-injection valve 4A2c. By pressing the gas-injection valve 4A2c open to open the gas inlet 4A2b, high-pressure gas in the high-pressure-gas reservoir 4A2a is injected into the cylinder 4A1a of the gas cylinder 4A1. When the pressure within the cylinder 4A1a becomes sufficiently high, a piston 4A1b is retracted, compressing a compression spring 4A1c.

When the trigger 4A4 is pulled, as shown in FIG. 17(b), the ejection nozzle 4A1f that is directly attached to the trigger 4A4 also moves rearward, retracting the gas-discharge valve 4A3 to an open state. At this time, high-pressure gas injected from the high-pressure-gas reservoir 4A2a and stored in the cylinder 4A1a is ejected through the ejection hole 4A1h and is emitted toward the nozzle 4A1g. Because the internal pressure in the cylinder 4A1a drops at the same time that high-pressure gas is emitted toward the nozzle 4A1g, the elastic force of the compression spring 4A1c, which was compressed by the retracted piston 4A1b, propels the piston 4A1b rapidly forward, compressing the gas in the cylinder 4A1a, thereby generating high-pressure compressed gas. In this way, the gas shooter 4A in this example can eject, in combination, both the high-pressure gas stored in the high-pressure-gas reservoir 4A2a and high-pressure gas generated by the rapid advancement of the piston 4A1b from the cylinder 4A1a toward the nozzle 4A1g.

The gas shooter 4A of this variation is configured to draw high-pressure gas from the high-pressure-gas reservoir 4A2a into the ejection hole 4A1h automatically with just one touch of the trigger 4A4. This configuration not only improves the operability and efficiency of small-pit closure surgery in hollow organs, but also enables a simpler structure in the gas shooter 4A than that in a gas shooter 4 having a control system for driving the motor 42e, as described in the first embodiment.

As shown in FIGS. 18(a) and 18(b), a gas shooter 4B according to another mode for carrying out the invention has a different configuration from the drive-control system in the gas shooter 4 of the first embodiment that used the motor 42e. In the gas shooter 4B, the piston 4B1b of the gas cylinder device 4B1 is pulled manually in the retracting direction, storing energy in the compression spring 4B1c and being locked in this position. When the piston is released through an operation of a trigger 4B4, for example, the piston 4B1b advances rapidly, generating compressed air.

The piston 4B1b is slidably retained in a cylinder 4B1a and has an O-ring or other sealing member (not shown) provided on its front end for maintaining a hermetic seal with the inner wall of the cylinder 4B1a. The compression spring 4B1c, which accumulates energy when the piston 4B1b is retracted, is fitted over a piston rod 4B1e and interposed between the piston 4B1b and an end plate 4B1d of the cylinder 4B1a. When compressed, the compression spring 4B1c has a strong force for pushing the piston 4B1b rapidly and instantly when the stored energy is released.

A rod grip 4B1h is provided on the rear-end portion of the piston rod 4B1e and extends outward from the rear end-face 4B1i of the cylinder 4B1a. An engaging protrusion 4B1j protrudes downward from the bottom surface of the piston rod 4B1e in front of the rod grip 4B1h.

The gas shooter body 4B2 of the gas shooter 4B has a handle 4B2a. The trigger 4B4 is pivotably supported on a shaft 4B3 provided in the gas shooter body 4B2 in front of the top portion of the handle 4B2a. A hook-like engaging part 4B4a extends from the upper-front edge of the trigger 4B4 so as to engage with the lower-front surface of the engaging protrusion 4B1j formed on the piston rod 4B1e.

A return spring (not shown) returns the trigger 4A4 to a standby state shown in FIG. 18(a). By gripping and manually retracting the rod grip 4B1h when the trigger 4A4 is in this standby state, the engaging protrusion 4B1j of the piston rod 4B1e slides over the engaging part 4B4a of the trigger 4B4 and the lower-front surface of the engaging protrusion 4B1j contacts and engages with the engaging part 4B4a, locking the piston 4B1b by energy stored in the compression spring 4B1c.

As shown in FIG. 18(b), pulling the trigger 4B4 disengages the engaging part 4B4a from the lower-front surface of the engaging protrusion 4B1j, thereby unlocking the piston 4B1b and releasing the compression spring 4B1c. Consequently, the piston 4B1b is instantly and rapidly propelled forward by the elastic force of the compressed compression spring 4B1c. Consequently, compressed air generated in the cylinder 4B1a is ejected through an ejection hole 4B1f, discharging compressed air into a nozzle (not shown) that is coupled to the front end of the gas shooter 4B.

With the gas shooter 4B according to this example, the piston 4B1b of the 4B1 gas cylinder is manually pulled in the retracting direction and locked, with energy being stored in the compression spring 4B1c. The piston 4B1b advances rapidly forward when released by an operation of the trigger 4B4, generating compressed air. This simple construction makes the structure of the gas shooter 4B simpler and more economical than the gas shooter 4 or 4A described above.

FIGS. 19(a) and 19(b) show a ratchet mechanism according to another mode for carrying out the invention in which a suture thread 133 inserted through a suture-thread-insertion part 132d attached to the rear end of an arrowy-shaped member can be freely pulled outward, but is restricted from returning inward. The suture thread 133, which is made of a deformable material, is inserted through an insertion hole 132d4 whose diameter is slightly narrower than the diameter of the suture thread 133. The suture thread 133, being constricted within the insertion hole 132d4, itself contracts in diameter and, hence can be freely pulled in the withdrawal direction. However, an inner frame 132d3 adjacent to the insertion hole 132d4 restricts the suture thread 133 from moving backward in the return direction, because the suture thread 133 itself expands in diameter when contacting the outer surface of the inner frame 132d3.

The deformable material used for the suture thread 133 of the above example can have small protuberances 133a or the like that are formed integrally therewith or through interwoven fibers to produce folds in the surface of the suture thread 133, as shown in the example of FIG. 19(a). The suture thread 133 contracts when moving in the withdrawal direction by deforming axially when constricted by the insertion hole 132d4, but expands in diameter when moving in the return direction by deforming radially outward, much like raised hackles.

As shown in the example of FIG. 19(a), the suture-thread-insertion part 132d of the current mode has a simple form that integrally includes a generally-annular outer frame 132d1 fixed to the rear end of the second arrowy-shaped member, an inner frame 132d3 in which the generally-circular insertion hole 132d4 is formed, with a generally-disc-shaped support member 132d2 disposed between the outer frame 132d1 and inner frame 132d3.

In another example of a ratchet mechanism for the suture-thread-insertion part 142d shown in FIG. 19(b), an insertion hole 142d4 formed in the inner frame 142d3 has a tapered inner surface that gradually narrows in the direction in which a suture thread 143 is pulled. The suture thread 143 is integrally formed of an elastically deformable material. Thus, the suture thread 143 can be easily and smoothly pulled in the withdrawal direction by itself contracting in diameter when constricted by the insertion hole 142d4. However, the suture thread 143 is restricted from moving in the return direction because when the suture thread 143 moves in the return direction, the diameter of the suture thread 143 expands (swells) much like raised hackles, against the outer surface of the inner frame 142d3 adjacent to the insertion hole 142d4.

Although not shown in the drawings, a narrow channel can be provided alongside the outer surfaces of the coupled portions of the tubes 51, air tubes 21, and the like, extending from the tubes 51 of the suture-member cartridge 5 to the rear ends 21b of the air tubes 21 in the hollow-organ-insertable unit 2. One end (first end) 103a of the suture thread 103 is attached to the rear end 101b of the first arrowy-shaped member 101, and the other end (second end) 103b of the suture thread 103 is inserted into and pulled freely through the rear end 102b of the second arrowy-shaped member 102 and inserted through the channel; and a suture-thread-take-up device provided near the gas shooter 4 can be configured to take up or release the suture thread 103. Unlike the configuration in the embodiments described above, the suture-thread-take-up device can take up the suture thread 103 without the surgical device 1 being withdrawn and, hence, a endoscope 200 or capsule endoscope 200A can be used to closely monitor and verify the small-pit site while the suture thread 103 is taken up. The rear ends 101b and 102b of the first and second arrowy-shaped members 101 and 102 embedded in the tissue around the small pit Tc can be drawn together, and the suture thread 103 can be locked so as not to loosen. Accordingly, through a single operation, the tissue in the stomach T around the small pit Tc can be quickly brought together and held in a sutured state.

Although not shown in the drawings, driving means for advancing the inner cylinders 35 of the auxiliary shooting unit 3B in the implementation mode shown in FIG. 13 can be accommodated in a linkage member that links the inner cylinders 35 to the switching plate 45b of the feed-air switching mechanism 45, for example, and can be configured either of a link-and-crank-gear mechanism well-known in the art or of a separate driving source for sequentially advancing the linkage member each time the switching plate 45*b* rotates in association with a trigger operation for pulling the trigger 44 of the gas shooter 4. Alternatively, the structure can be simplified so that the linkage member is sequentially advanced by hand.

Third Embodiment

As shown in FIGS. 20 and 21, a surgical system for small-pit closure in hollow organs according to a third embodiment differs from the first embodiment in that a surgical device 1C for small-pit closure in hollow organs is arranged along the outer surface of the endoscope 200, extending to the leading-end 202 thereof, and particularly in that multiple pairs of suture-member cartridges 5, multiple pairs of auxiliary shooting units 3, and a feed-air switching mechanism 60 are connected in sequence from the leading end of the surgical device 1C along the outer circumference of the leading-end 202, with the leading-end portion constituting a head unit 10; and a hollow-organ-insertable unit 2C configured of a single air tube is connected to the rear end of the feed-air switching mechanism 60. The individual structures of the suture-member cartridges 5 and auxiliary shooting units 3 are identical to those in the first embodiment. Therefore, components in FIGS. 20 and 21 of the third embodiment that have the same function as components in the first embodiment are assigned the same reference numerals, even when differing partially in form, and duplicate descriptions of these components are omitted.

As shown in FIG. 21, the multiple pairs (three pairs in FIG. 21) of the suture-member cartridges 5 and auxiliary shooting units 3 in the third embodiment are configured of films formed of medically compatible material, such as elastomer or a resin-based material, and are accommodated in a hollow double-cylinder structure that includes an inner cylinder 12 removably fitted around the outside of the leading-end 202, an outer cylinder 11, and front and rear walls 13 and 14 such that the space between the inner cylinder 12 and outer cylinder 11 is hermetically sealed. That is, the suture-member cartridges 5 and auxiliary shooting units 3 are juxtaposed axially with each other and disposed in the space between the inner cylinder 12 and the outer cylinder 11 at substantially regular intervals between the pairs of the suture-member cartridges 5 and auxiliary shooting units 3 in the circumferential direction of the inner cylinder 12 and the outer cylinder 11. The leading-ends 51*a* of the suture-member cartridges 5 and rear ends 31*b* of the auxiliary shooting units 3 are respectively inserted through openings formed in the front and rear walls 13 and 14.

Although not shown in the drawing, the outer cylinder 11 is a flexible member that is deformed to conform to the outer shapes of the suture-member cartridges 5, the auxiliary shooting units 3, and the inner cylinder 12, which is fitted over the leading-end 202 so as to be in fairly close contact with the same. If at least the outer cylinder 11 is formed of material with a heat-shrinkable property, the outer cylinder 11 can be deformed so that its intermediate portion is in complete contact with the suture-member cartridges 5, the auxiliary shooting units 3, and the outer circumference of the inner cylinder 12.

As a variation of the embodiment (not shown), the outer cylinder 11 can be omitted, and the suture-member cartridges 5 and auxiliary shooting units 3, which extend axially and are arranged side by side in pairs at substantially equal intervals in the circumferential direction around the outer surface of the inner cylinder 12 that is fitted over the leading-end 202, can be individually covered with a film formed of an elastomer or a resin-based material and can be fixed to the outer surface of the inner cylinder 12 in this state.

As another variation of the embodiment (not shown), the outer cylinder 11 can be omitted, and the pairs of suture-member cartridges 5 and auxiliary shooting units 3 can be packaged as individual pairs, with a film formed of an elastomer or resin-based material provided around their outer surfaces, and can be arranged axially and fixed to the outer surface of the inner cylinder 12 fitted around the leading-end 202 at substantially regular intervals between each pair in the circumferential direction of the inner cylinder 12.

As shown in FIGS. 21 and 22, the feed-air switching mechanism 60 includes: (1) a generally cylindrical hollow case 61 interposed between the auxiliary shooting unit 3, which (a) is coupled to the suture-member cartridge 5 and the hollow-organ-insertable unit 2C, (b) has front and rear walls coupled to the auxiliary shooting unit 3 and the hollow-organ-insertable unit 2C, respectively, and (c) is fitted around the leading-end 202; (2) a rotary member 62 rotatably that is accommodated in the hollow case 61 and has a switching plate 62*b* formed adjacent to the front wall of the hollow case 61; and (3) a driving means that rotates the rotary member 62 in association with a trigger operation on the gas shooter in order to sequentially switch the rotary member 62 between a circulation-state position through an opening 62*c* formed in the switching plate 62*b* and a non-circulation-state position that is achieved by a shielding part constituting the portion of the rotary member 62 other than the opening 62*c*.

As shown in FIG. 22, the driving means includes the following components, which are all accommodated in the hollow case 61: (1) a knock member 63 (see FIG. 24) that has on its rear end a piston 63*a* and on its front end pressing teeth 63*b* in a number N that is equal to the number of suture-member cartridges 5 and auxiliary shooting units 3 (N=6 in this example) and that is shaped to fit around the generally cylindrical body 62*a* of the rotary member 62 while freely moving forward and rearward; (2) protruding parts 62*d* formed on the outer circumference of the cylindrical body 62*a* connected to the switching plate 62*b* of the rotary member 62; (3) a cam cylinder 64 (see FIG. 23) that has N/2 (=3 in this example) of both deep first-cam grooves 64*a* and shallow second-cam grooves 64*b* formed alternately on the inner surface thereof at circumferential intervals (pitch angles) corresponding to the placement of the suture-member cartridges 5 and auxiliary shooting units 3 for alternately engaging with the protruding parts 62*d* on the rotary member 62 while being capable of moving freely forward and rearward, and that also has a front-end face that contacts the inner surface on the front wall of the hollow case 61; and (4) a compression spring 65 interposed between the cam cylinder 64 and piston 63*a* for constantly urging the piston 63*a* toward the rear side of the hollow case 61.

The above structure constitutes a gas-pressure rotary-knock mechanism in which compressed air or high-pressure gas ejected sequentially in response to trigger operations on the gas shooter and supplied into the hollow case 61 via the hollow-organ-insertable unit 2C pushes against the piston 63*a*, causing the knock member 63 to advance while the pressing teeth 63*b* follow along the first and second-cam grooves 64*a* and 64*b*. When the pressing teeth 63*b* contact and slide over the sloped surfaces formed on the end-faces of the protruding parts 62*d* provided on the rotary member 62, the rotary member 62 rotates one pitch angle at a time.

Figure 25:
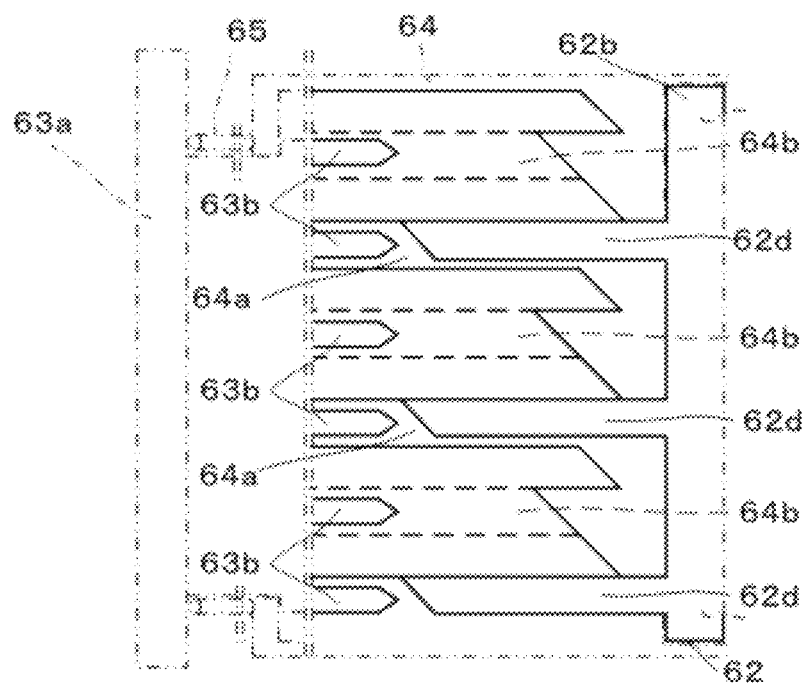
Figure 25:
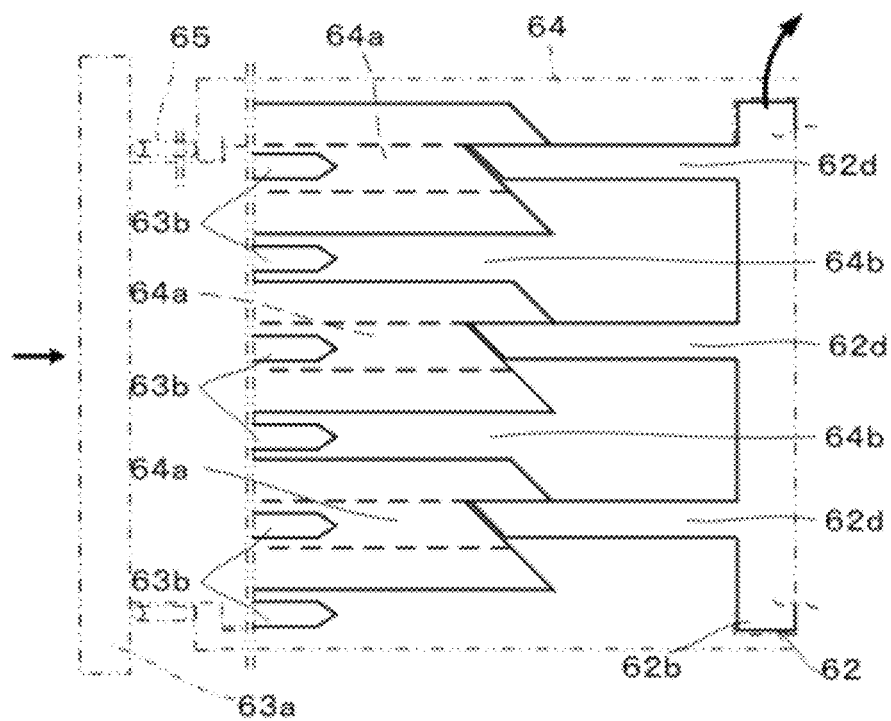

When the feed-air switching mechanism 60 having the above structure is inactive, the protruding parts 62*d* of the rotary member 62 are fitted in the first-cam grooves 64*a*, as illustrated in FIG. 25(*a*). When the trigger of the gas shooter is operated in this state, the knock member 63 is advanced by compressed air or high-pressure gas pushing against the piston 63*a*, and the pressing teeth 63*b* advance along the first-cam grooves 64*a* until they contact the end-faces of the protruding parts 62*d* provided on the rotary member 62. Because the end-faces of the protruding parts 62*d* are sloped, the rotary member 62 rotates in the direction of the arrow shown in FIG. 25(*b*) when the knock member 63 reaches the end of its advancement.

For the sake of description, FIGS. 25(*a*) and 25(*b*) are similar to development views that are not drawn to scale and are modeled after explanatory diagrams for the operations of a common rotary-knock mechanism well known in the art.

With this construction, compressed air or high-pressure air introduced into the hollow case 61 flows from a space S—that is defined by the knock member 63, inner cylindrical surface of the hollow case 61, cylindrical body 62*a* of the rotary member 62, and the like—into a space Sa near the switching plate 62*b* through the opening 62*c* formed in the switching plate 62*b*, through one of N (N=6 in this example) circulation holes 61*a* formed in the front wall of the hollow case 61 at locations corresponding to the auxiliary shooting units 3, and flows sequentially into the corresponding auxiliary shooting units 3. Because the surface area on the rear end-face of the piston 63*a* is greater than the surface area on the front-end face on the space Sa side, the knock member 63 can overcome the lesser force of the compression spring 65 and advance when the compressed air or high-pressure gas pushes against the piston.

The surgical system for small-pit closure in hollow organs according to the third embodiment differs from the first embodiment in that the surgical device 1C is arranged along the outer surface of the endoscope 200, extending to the leading-end 202 thereof; the head unit 10 includes multiple pairs of the suture-member cartridges 5 that accommodate the suture members 100A and multiple pairs of the auxiliary shooting units 3; the feed-air switching mechanism 60 is provided on the outer surface of the leading-end 202; and the hollow-organ-insertable unit 2C configured of a single air tube is arranged along the outer surface of the hollow-organ-insertable tube 201 of the endoscope 200. Therefore, in addition to the effects described in the first embodiment, the surgical system according to the third embodiment is provided with multiple pairs of the suture-member cartridges 5 and configured with a narrow hollow-organ-insertable unit 2C, making it possible to form multiple sutures efficiently in the tissue of the hollow organ T around the small pit Tc (the mucosa Tb and submucosa Ta; see FIG. 5), so as to further reduce the duration and invasiveness of surgery, and to eliminate the potential for internal damage to the operating channels 202*a* and 202*b* of the endoscope 200. This configuration also improves the freedom for designing the surgical device 1C of the surgical system for small-pit closure in hollow organs, because the device is not constrained by usual conditions of endoscope usage, such as the internal dimensions of the operating channels 202*a* and 202*b*.

Fourth Embodiment

As shown in FIG. 26, a surgical system for small-pit closure in hollow organs according to a fourth embodiment is nearly identical in structure to the surgical device described in the first embodiment, except that a surgical device 1D for small-pit closure in hollow organs is arranged alongside the outer surface of the endoscope 200, extending to the leading-end 202 thereof. Therefore, components in FIG. 26 of the fourth embodiment that have the same function as components in the first embodiment are assigned the same reference numerals, even when differing partially in form, and duplicate descriptions of these components are omitted.

Because the surgical system for small-pit closure in hollow organs according to the fourth embodiment differs from the first embodiment only in that in the fourth embodiment the surgical device 1D for small-pit closure in hollow organs is arranged alongside the outer surface of the endoscope 200 to the leading-end 202 thereof, so that, in addition to the effects described in the first embodiment, the surgical system according to the fourth embodiment eliminates the potential for internal damage to the operating channels of the endoscope and increases the freedom for designing the surgical device 1D without being restricted by the internal dimensions of the operating channels or the like.

Fifth Embodiment

In a surgical system for small-pit closure in hollow organs according to a fifth embodiment, a surgical device 1E for small-pit closure in hollow organs is nearly identical in structure to the surgical device described in the first embodiment, except that, as shown in the structure of the leading-end portion of the surgical device 1E, which is the relevant portion in FIG. 27, the pair of tubes 51 and a narrow tube 70 interposed between the tubes 51 are arranged alongside the outer surface of an endoscope (not shown), extending to the leading-end thereof; a middle portion 103*c* of the suture thread 103 is inserted as a U-shaped loop through a threading member 115 into the narrow tube 70 and is connected to suture-thread-pulling means 120X; and the rear ends 101*b* and 102*b* of the first and second arrowy-shaped members 101 and 102 that are embedded in the tissue of the hollow organ T on both sides of the small pit Tc site are drawn together when the middle portion 103*c* of the suture thread 103 is pulled by the pulling means 120. Therefore, components in FIG. 27 of the fifth embodiment that have the same function as components in the first embodiment are assigned the same reference numerals, even when differing partially in form, and duplicate descriptions of these components are omitted.

The surgical device 1E according to the fifth embodiment has at least one pair of tubes 51, and the narrow tube 70 is interposed between the tubes 51 that form each pair arranged along the outer surface on the leading-end portion of the endoscope. The suture thread 103 is diverted around the leading ends of the tubes 51 or passed through small holes that are slit-like openings (not shown) respectively provided in the opposing side walls of the tubes 51, and the middle portion 103*c* of the suture thread 103 is inserted into a U-shaped loop through the threading member 115 and accommodated in the narrow tube 70. The first and second arrowy-shaped members 101 and 102, which form a pair that are linked by the suture thread 103, are respectively accommodated in the tubes 51. The leading-end of the surgical device 1E includes: (1) at least one pair of suture-member cartridges 5, and (2) an auxiliary shooting unit, not shown in the drawings, that is identical to that in the first embodiment and that is coupled to the rear end of each suture-member cartridge 5, (3) a hollow-organ-insertable unit (identical to that described in the first embodiment), (4) a feed-air switching mechanism (identical to that described in either the first or third embodiment), and (5) a gas shooter (identical to that described in the first embodiment).

The ends 103*a* and 103*b* of a suture thread 103 are respectively attached to the rear ends 101*b* and 102*b* of the first and second arrowy-shaped members 101 and 102 for each pair thereof.

The suture-thread-pulling means 120X has (1) a flexible guide tube 122X that can be inserted into the narrow tube 70, and (2) a wire 123 that is inserted from the leading-end portion of the pulling means 120 into the guide tube 122 and that is provided with an engaging part 124, such as a hook, that engages with the U-shaped loop formed in the middle portion 103c of the suture thread 103 accommodated in the narrow tube 70. The wire 123 pulls the middle portion 103c of the suture thread 103 through the rear end of the engaging part 124 on the side away from the hollow organ in the direction away from the hollow organ.

The suture-thread-pulling means 120X has a wire-take-up means 121X that is coupled to the rear end of the guide tube 122X outside the hollow organ and is fixed to the rear end of the wire 123X. When the trigger 121Xb is operated, for example, the wire-take-up means 121X is electrically controlled to rotate in the direction for taking up the wire 123X.

Next, a surgical method using the surgical system for small-pit closure in hollow organs according to the fifth embodiment for suturing tissue in the hollow organ T around a small pit Tc site will be described with reference to FIGS. 28 and 29.

The leading-end portion of the endoscope and the leading end of the suture-member cartridge 5 on the side of the tubular member 51 accommodating the first arrowy-shaped members 101 are moved to a prescribed distance from the surface of the mucosa Tb at a first position Tb1 near the small pit Tc (first step for positioning leading end of suture-member cartridge; see FIG. 28).

The trigger of the gas shooter (not shown) is then pulled to eject the first arrowy-shaped member 101 toward the first position Tb1 (step for ejecting first arrowy-shaped member). As a result, the first arrowy-shaped member 101 is driven into the submucosa Ta near the first position Tb1, as shown in FIG. 28.

Next, the leading-end portion of the endoscope and the leading end of the suture-member cartridge 5 on the side of the tubular member 51 accommodating the second arrowy-shaped member 102 are moved and placed at a prescribed distance from the surface of the mucosa Tb at a second position Tb2 near the small pit Tc on the side opposite the first position Tb1 (second step for positioning leading end of suture-member cartridge; see FIG. 28).

The trigger of the gas shooter (not shown) is once again pulled, to eject the second arrowy-shaped member 102 toward the second position Tb2 (step for ejecting second arrowy-shaped member). As a result, the second arrowy-shaped member 102 is driven into the submucosa Ta near the second position Tb2, as shown in FIG. 28. At this time, as the first and second arrowy-shaped members 101 and 102 are ejected, both ends 103a and 103b of the suture thread 103 are ejected out of the leading ends of the pair of tubes 51 on the side near their coupled portion. Although the first and second arrowy-shaped members 101 and 102 are driven such that a portion of the leading ends 101a and 102a pierce the submucosa Ta at this time, this is not particularly problematic.

Next, while the endoscope is used to confirm the embedded state of the first and second arrowy-shaped members 101 and 102 and the suture-member cartridge 5 of the surgical device 1E is brought closer to the surface of the mucosa Tb, the trigger 121Xb of the wire-take-up means 121X in the suture-thread-pulling means 120X is operated to take up the wire 123X while the engaging part 124 is engaged with the loop formed in the middle portion 103c of the suture thread 103 accommodated in the narrow tube 70, pulling the middle portion 103c of the suture thread 103 in the direction away from the hollow organ. As a result, the suture thread 103 that is fixed to the rear ends 101b and 102b of the first and second arrowy-shaped members 101 and 102 draws the rear end 101b of the first arrowy-shaped member 101 and rear end 102b of the second arrowy-shaped member 102 together, forming a tight suture in the tissue around the small pit Tc (step for stitching the small-pit site).

As shown in FIG. 28, the threading member 115 is provided with a thread-insertion hole 115a along its central axis and is fixed inside the leading-end portion of the narrow tube 70. By pulling the middle portion 103c of the suture thread 103 that has been inserted into a U-shaped loop through the thread-insertion hole 115a of the threading member 115, the rear ends 101b and 102b of the first and second arrowy-shaped members 101 and 102 that are embedded in the tissue of the hollow organ T around the small pit Tc can be smoothly drawn together.

The surgical system for small-pit closure in hollow organs of the fifth embodiment differs from the first embodiment in that each pair of the tubes 51 in the surgical device 1E and the narrow tube 70 interposed therebetween are arranged alongside the outer surface of the endoscope, extending to the leading end thereof; the middle portion 103c of the suture thread 103 is inserted into a U-shaped loop through the threading member 115, is accommodated in the narrow tube 70, and is connected to the suture-thread-pulling means 120X; and the rear ends 101b and 102b of the first and second arrowy-shaped members 101 and 102 that are embedded in tissue of the hollow organ T on both sides of the small pit Tc site are drawn together by pulling the middle portion 103c of the suture thread 103 with the suture-thread-pulling means 120X. Therefore, in addition to the effects of the invention described in the first embodiment, the surgical system according to the fifth embodiment, by drawing together the rear ends 101b and 102b of the first and second arrowy-shaped members 101 and 102 while the suture thread 103 is symmetrically connected to the first and second arrowy-shaped members 101 and 102, can improve operability while eliminating the need to retract the endoscope when forming a suture.

Industrial Applicability

With the surgical device for small-pit closure in hollow organs according to the present invention, the hollow-organ-insertable unit, on which the suture-member cartridge and auxiliary shooting unit are coupled on the leading end of the surgical device, is inserted through the operating channel of an endoscope or alongside the outer surface of the endoscope, or, via a natural orifice of a living body by using a capsule endoscope, is inserted directly into a hollow organ having a small pit; compressed air or high-pressure gas discharged from a gas shooter generates secondary compressed air in the auxiliary shooting unit 3 for sequentially ejecting the adjacent first and second arrowy-shaped members from the suture-member cartridge; and the rear ends of the first and second arrowy-shaped members that have been driven into the tissue in the hollow organ on both sides of the small-pit site are drawn together via the suture thread linking those same rear ends, whereby the tissue around the small-pit site can easily be closed and held in a sutured state through one simple and quick operation. Hence, the surgical system for small-pit closure in hollow organs of the present invention (1) can reduce the duration and invasiveness of surgery by eliminating the need for conventional major surgical procedures, such as abdominal incisions, and (2) is excellent in operability, safety, and reliability. Accordingly, the present invention can be applied versatilely to a wide range of surgical procedures to suture tissue around the site of a small pit in a digestive tract, such as the stomach and intestines, or in another hollow organ, including the sites of perforations in lesions caused by cancer or the like, accidental piercings (punctures and other surgical wounds) occurring during treatment, and perforations formed for performing endoscopic gall bladder surgery through the stomach.

Alphanumeric Characters Used in the Drawings and Text

| Reference | Description |
|---|---|
| 1, 1A, 1C, 1D, 1E | surgical device for small-pit closure in hollow organs |
| 2, 2A, 2C | hollow-organ-insertable unit |
| 3, 3A, 3B | auxiliary shooting unit |
| 4, 4A, 4B | gas shooter |
| 4A1, 4B1, 41 | gas cylinder device |
| 4A1a, 4B1a, 41a | cylinder |
| 4A1b, 4B1b, 41b | piston |
| 4A1c, 4B1c, 41c | compression spring |
| 4A1f | ejection nozzle |
| 4A1g, 41g | nozzle |
| 4A1h, 4B1f, 41f | ejection hole |
| 4A2, 4B2a | handle |
| 4A2a | high-pressure-gas reservoir |
| 4A2b | gas inlet |
| 4A2c | gas-injection valve |
| 4A3 | gas-discharge valve |
| 4A4, 4B4, 44 | trigger |
| 4B1d | end plate |
| 4B1e | piston rod |
| 4B1h | rod grip |
| 4B1j | engaging protrusion |
| 4B3 | shaft |
| 4B4a | engaging part |
| 5, 5A, 5B, 5C | suture-member cartridge |
| 7 | feed-air-pressure controller |
| 8, 8A, 8C | operating unit |
| 10 | head unit |
| 11 | outer cylinder |
| 12 | inner cylinder |
| 13 | front wall 13 |
| 14 | rear wall 14 |
| 21 | air tube |
| 21a, 31a, 31Ba, 51a, 51Ba, 101a, 101Aa, 102a, 102Aa, 111a, 112a, 121a, 122a | leading end |
| 21b, 21Ab, 31b, 51b, 51Bb, 101b, 101Ab, 102b, 102Ab, 111b, 112b, 121b, 122b | rear end |
| 22, 22A, 32, 52 | coupling tube |
| 31, 31B | open-ended cylinder |
| 32a, 52a | inner surface |
| 33, 33B | plunger support |
| 33a, 33Ba | through-hole |
| 33b | fixed frame |
| 34, 34B | plunger |
| 34a, 34Ba | front plunger part |
| 34b, 34Bb | rear plunger part |
| 34c, 34Bc | coupling shaft |
| 34d, 34Bd | return spring |
| 35 | inner cylinder |
| 41d | spindle |
| 41e | rack teeth |
| 42 | drive mechanism |
| 42a | sector gear |
| 42b | tooth portion |
| 42c | toothless portion |
| 42d | transmission-gear mechanism |
| 42e | motor |
| 43 | tappet |
| 45, 45A | feed-air switching mechanism |
| 45a, 45Aa | case |
| 45b, 45Ab | switching plate |
| 45c, 45Ac | opening |
| 45d, 45Ad | shielding part |
| 45e, 45A | driving means |
| 51, 51B | tubular member |
| 53, 53B | small opening or slit-like opening |
| 60 | feed-air switching mechanism |
| 61 | case |
| 61a | circulation hole |
| 62 | rotary member |
| 62a | cylindrical body |
| 62b | switching plate |
| 62c | opening |
| 62d | protruding parts |
| 63 | knock member |
| 63a | piston |
| 63b | pressing teeth |
| 64 | cam cylinder |
| 64a | first-cam grooves 64a |
| 64b | second-cam grooves 64b |
| 65 | compression spring |
| 70 | narrow tube |
| 100, 100A, 110X, 120 | suture member |
| 101, 101A, 111, 121 | first arrowy-shaped member |
| 101c, 101Ac, 102c, 102Ac, 111c, 112c, 121c, 122c | engaging part |
| 102, 102A, 112, 122 | second arrowy-shaped member |
| 102d, 132d, 142d | suture-thread-insertion part |
| 102d1, 132d1 | outer frame |
| 102d2 | elastic support member |
| 102d3, 132d3, 142d3 | inner frame |
| 102d4, 102e, 122e, 132d4, 142d4 | insertion hole |
| 102d5 | slit parts |
| 103, 113, 123, 133, 143 | suture thread |
| 103a, 113a, 123a | one (first) end |
| 103b, 113b, 123b | opposite (second) end |
| 103c | middle portion |
| 110 | partitioning member |
| 110A | vane |
| 110Aa | leading ends |
| 110Ab | rear ends |
| 115 | threading member |
| 115a | thread-insertion hole |
| 120 | suture-thread pulling means |
| 121 | wire-take-up means |
| 121Xa | wire-take-up device |
| 121Xb | trigger |
| 122X | guide tube |
| 123X | wire |
| 124 | suture-thread engaging part |
| 132d2 | support member |
| 133a | fold-like protuberances |
| 143a | expanding part |
| 200 | endoscope |
| 200A | capsule endoscope |
| 201 | hollow-organ-insertable tube |
| 202 | leading-end of endoscope |
| 202a | first operating channel |
| 202b | second operating channel |
| 202c | illumination window |
| 202d | observation window |
| 203 | operating unit of endoscope |
| M | body (e.g., human body) |
| Ma | natural orifice (e.g., mouth) |
| S | space |
| Sa | space (near switching plate) |
| T | hollow organ (e.g., stomach or other digestive tract) |
| Ta | submucosa (of stomach or other hollow organ) |
| Tb | mucosa (of stomach or other hollow organ) |
| Tb1 | first position |
| Tb2 | second position |
| Tc | small pit |

The invention claimed is:

1. A surgical system having a surgical device for small-pit closure in hollow organs with said surgical device being a suturing device formed so as to be freely insertable through an operating channel of an endoscope inserted into a hollow organ so as to suture, through the operating channel, tissue at the site of a small pit in the hollow organ by using a suture member that includes (a) at least one pair of first and second arrow-shaped members having engaging parts that engage with tissue in the hollow organ, and (b) a suture thread that is attached by one of its ends (first end) to the rear end of the first arrow-shaped member and that is inserted into and pulled freely through the rear end of the second arrow-shaped member, with said surgical device comprising:

(1) a suture-member cartridge constituting a leading-end portion of the surgical device and having at least one pair of tubes arranged parallel to each other, whereby the suture thread is diverted around leading ends of the tubes or passed through small holes or slit-like openings provided in opposing side walls of the tubes and is fixed by an opposite (second) end of the suture thread to an inner surface on the leading end side of a tube member that accommodates the second arrow-shaped member, with the arrow-shaped member linked by the suture thread forming a pair that are respectively accommodated in the tubes;

(2) a hollow-organ-insertable unit that includes flexible air tubes that are coupled to a rear end of the suture-member cartridge; and (3) a gas shooter that is coupled to a rear end of the hollow-organ-insertable unit outside the hollow organ and that includes a cylinder unit that has (a) a piston that, through its operation, generates compressed air, and (b) a high-pressure-gas reservoir that stores high-pressure gas, with said compressed air or high-pressure gas being released through an ejection hole in response to trigger operations of the gas shooter and sequentially ejected into the suture-member cartridge via the hollow-organ-insertable unit;

and the arrow-shaped members are sequentially ejected from the suture-member cartridge by compressed air or high-pressure gas sequentially ejected into the suture-member cartridge and are driven into tissue in the hollow organ on both sides of the small-pit site, with the rear ends of the arrow-shaped members being drawn together via the suture thread linking those rear ends so as to tightly suture the small-pit site.

2. A surgical system for small-pit closure in hollow organs according to claim 1, further including an auxiliary shooting unit that has (1) an open-ended cylinder that is coupled and interposed between the suture-member cartridge and the hollow-organ-insertable unit, and (2) a plunger accommodated in the open-ended cylinders that moves freely forward and rearward while being maintaining airtight;

and compressed air or high-pressure gas is sequentially ejected into the auxiliary shooting unit via the hollow-organ-insertable unit in response to a trigger operation on the gas shooter, whereby the plungers advance rapidly in sequence and generate secondary compressed air for sequentially ejecting the arrow-shaped members from the suture-member cartridge and driving the arrow-shaped members into tissue in the hollow organ on both sides of the small-pit site.

3. A surgical system for small-pit closure in hollow organs according to claim 1, wherein the surgical device for small-pit closure in hollow organs includes multiple pairs of suture-member cartridges, and the air tubes are arranged parallel to each other.

4. A surgical system for small-pit closure in hollow organs according to claim 1, wherein the feed-air switching mechanism that switches between a circulation state for supplying compressed air or high-pressure gas sequentially into each air tube in the hollow-organ-insertable unit and a non-circulation state for blocking the compressed air or high-pressure gas is interposed between the rear end of the hollow-organ-insertable unit on the outside of the hollow organ and the gas shooter.

5. A surgical system for small-pit closure in hollow organs according to claim 1, wherein the gas shooter generates compressed air by driving the piston of a gas cylinder device in the retracting direction by a motor, thereby storing energy in a compression spring, and then rapidly advancing the piston by the repelling force of the compression spring by controlling, through a trigger operation, the actuation of the motor.

6. A surgical system for small-pit closure in hollow organs according to claim 1, wherein the piston of the gas cylinder device in the gas shooter is manually pulled in a retracting direction, thereby storing energy in a compression spring, and is then locked, with the piston rapidly advancing due to the repelling force of the compression spring when the lock is released through a trigger operation.

7. A surgical system for small-pit closure in hollow organs according to claim 1 further provided with a feed-air-pressure controller on a side of the gas shooter, for adjusting the pressure of the compressed air or high-pressure gas so that the compressed air or high-pressure gas is ejected to a desired magnitude.

8. A surgical system for small-pit closure in hollow organs according to claim 1, wherein each arrow-shaped member includes a linear, rod-like, or strip-like body having an engaging part that is elastic and formed in a hook shape on or near the leading end of the arrow-shaped member and that is angled outward and rearwardly.

9. A surgical system for small-pit closure in hollow organs according to claim 8, further including partitioning members that are provided on or near the rear ends of the arrow-shaped members, that are generally shaped like discs or short cylinders, that are formed of a material that is biocompatible with the hollow organ or that is either digestible or soluble or capable of being discharged from the body, and that freely slide in the tubular members in a generally hermetic state therewith.

10. A surgical system for small-pit closure in hollow organs according to claim 8, further including vanes that (1) have a generally conical shape, (2) are connected to the rear ends of the arrow-shaped members, (3) are formed of a film-like material that is biocompatible with the hollow organ or that is either digestible or soluble or capable of being discharged from the body, (4) expand outward toward the rear and (5) are freely slidable in the tubular members while maintaining a generally hermetic state therewith.

11. A surgical system for small-pit closure in hollow organs according to claim 1, wherein each of the paired arrow-shaped members has a generally round bar-shaped or cylindrical body with a sharply formed leading end, with one or multiple elastic engaging parts formed on side surfaces near said leading end and angling outward toward the rear in a hook shape for engaging with tissue in the hollow organ.

12. A surgical system for small-pit closure in hollow organs according to claim 11, wherein the engaging parts of the arrow-shaped members are formed by cutting and spreading outward side surfaces of generally round bar-shaped, cylindrical, or conical bodies.

13. A surgical system for small-pit closure in hollow organs according to claim 11, wherein the arrow-shaped members are generally round bar-shaped, cylindrical, or conical bodies whose side surfaces are partially cut out to form notches, and the engaging parts of the arrow-shaped members are formed by fixing one end of a linear or strip-like body to each of the notch parts.

14. A surgical system for small-pit closure in hollow organs according to claim 11, wherein an insertion hole for inserting the suture thread is provided in a side surface of the second arrow-shaped member near the rear end thereof and communicates with the suture-thread-insertion unit.

15. A surgical system for small-pit closure in hollow organs according to claim 1, and further including a suture-thread-insertion part provided on the rear end of the second arrow-shaped member, and having a ratchet mechanism through which the suture thread is inserted so that the suture thread can be pulled freely in a withdrawal direction, but restricts the suture thread from being pulled back in the return direction.

16. A surgical system for small-pit closure in hollow organs according to claim 15, wherein the ratchet mechanism includes an insertion-hole unit through which the suture thread is inserted and that is supported by an elastic support member that is capable of deforming to allow the suture thread to be pulled in the withdrawal direction when the diameter of the insertion-hole increases, while preventing the suture thread from moving in the return direction when the diameter of the insertion-hole decreases.

17. A surgical system for small-pit closure in hollow organs according to claim 16, wherein the inner surface of the insertion-hole unit is tapered and gradually narrows in diameter in the direction that the suture thread is pulled.

18. A surgical system for small-pit closure in hollow organs according to claim 15, wherein the ratchet mechanism includes a suture thread formed of a deformable material that is inserted through an insertion-hole unit formed slightly narrower than a diameter of the suture thread so that the suture thread is freely pulled in the withdrawal direction by contracting in diameter when constricted in the insertion-hole unit, but is restricted from moving in the return direction because the suture thread expands in diameter when the suture thread moves in the return direction, much like raised hackles, against the outer surface adjacent to the insertion-hole unit.

19. A surgical system for small-pit closure in hollow organs according to claim 1, wherein a slit-like opening for inserting each of the suture threads penetrates the tube walls in a coupled portion of the tubes from a leading end of the suture-member cartridge, and multiple pairs of the arrow-shaped members are arranged in series at substantially regular intervals and accommodated in the tubular members; and plungers in the auxiliary shooting unit advance rapidly in sequence at a prescribed stroke when compressed air or high-pressure gas is sequentially ejected in response to a trigger operation on the gas shooter, ejecting each pair of arrow-shaped members sequentially.

20. A surgical system for small-pit closure in hollow organs according to claim 19, wherein the auxiliary shooting unit has a double-cylinder structure, including open-ended cylinders, with the inner cylinders being accommodated in the open-ended cylinders and being capable of moving forward and rearward, with the inner cylinders accommodating a pair of plungers that move freely forward and rearward while maintaining a hermetic seal with the inner cylinders; and the inner cylinders advance one pitch equivalent to the substantially regular intervals of the arrow shaped arrow-shaped members each time one pair of the arrow-shaped members is ejected, establishing a new ejection starting point.

21. A surgical system having a surgical device for small-pit closure in hollow organs, with said surgical device being a suturing device formed to be directly and freely inserted into a hollow organ so as to suture tissue at the site of a small pit in the hollow organ by using a suture member that includes (a) at least one pair of first and second arrow-shaped members having engaging parts that engage with tissue in the hollow organ, and (b) a suture thread that is attached by one of its ends (first end) to a rear end of the first arrow-shaped member and that is inserted into and pulled freely through a rear end of the second arrow-shaped member; with said system also having a capsule endoscope that either is accommodated inside a leading end of the surgical device or is inserted directly into the hollow organ; and with said surgical device comprising:

(1) a suture-member cartridge constituting a leading-end portion of the surgical device and having at least one pair of tubes arranged parallel to each other, whereby the suture thread is diverted around the leading ends of the tubes or passed through small holes or slit-like openings provided in opposing side walls of the tubes and is fixed by the opposite end (second end) of the suture thread to an inner surface of the leading-end side of a tubular member that accommodates the second arrow-shaped member, with the arrow-shaped member, which are linked by the suture thread to form a pair, being respectively accommodated in the tubes;

(2) a hollow-organ-insertable unit that includes flexible air tubes that are coupled to a rear end of the suture-member cartridge; and (3) a gas shooter that is coupled to a rear end of the hollow-organ-insertable unit outside the hollow organ and that includes a cylinder unit having either (a) a piston that, through its operation, generates compressed air, or (b) a high-pressure-gas reservoir that stores high pressure gas, with said compressed air or high-pressure gas being released through an ejection hole in response to trigger operations of the gas shooter and sequentially ejected into the suture-member cartridge via the hollow-organ-insertable unit;

and the arrow-shaped members are sequentially ejected from the suture-member cartridge by compressed air or high-pressure gas sequentially ejected into the suture-member cartridge and are driven into tissue in the hollow organ on both sides of a small-pit site, with the rear ends of the arrow-shaped members being drawn together via the suture thread linking those rear ends so as to tightly suture the small-pit site.

22. A surgical system having a surgical device for small-pit closure in hollow organs, with said surgical device being a suturing device mounted along the outer surface of an endoscope inserted into a hollow organ and extending to the leading-end portion of the endoscope so as to suture tissue at the site of a small pit in the hollow organ, by using a suture member that includes (a) at least one pair of first and second arrow-shaped members having engaging parts that engage with tissue in the hollow organ, and (b) a suture thread that is attached by one of its ends (first end) to a rear end of the first arrow-shaped member and is then inserted into and pulled freely through a rear end of the second arrow-shaped member, and with said surgical device comprising:

(1) a suture-member cartridge constituting a leading-end portion of the surgical device and having at least one pair of tubes arranged alongside the outer surface of an leading-end portion of the endoscope, and whereby the suture thread is diverted around the leading ends of the tubes or passed through small holes or slit-like openings provided in opposing side walls of the tubes and is fixed by an opposite end (second end) of the suture thread to an inner surface of the leading-end side of the tubular member that accommodates the second arrow-shaped member, with the arrow-shaped members, which are linked by the suture thread to form a pair, being respectively accommodated in the tubes;

(2) a hollow-organ-insertable unit that includes flexible air tubes that are coupled to a rear end of the suture-member cartridge; and (3) a gas shooter that is coupled to a rear end of the hollow-organ-insertable unit outside the hollow organ and that includes a cylinder unit having either (a) a piston that, through its operation, generates compressed air, or (b) a high-pressure-gas reservoir that stores high-pressure gas; with said compressed air or high-pressure gas being released through an ejection hole in response to trigger operations of the gas shooter and sequentially ejected into the suture-member cartridge via the hollow-organ-insertable unit;

and the arrow-shaped members are sequentially ejected from the suture-member cartridge by compressed air or high-pressure gas sequentially ejected into the suture-member cartridge and are driven into tissue in the hollow organ on both sides of the small-pit site, with the rear ends of the arrow-shaped members drawn together via the suture thread linking those rear ends, so as to tightly suture the small-pit site.

23. A surgical system having a surgical device for small-pit closure in hollow organs, with said surgical device being a suturing device mounted along an outer surface of an endoscope inserted into a hollow organ and extending to a leading-end portion of the endoscope so as to suture tissue at a site of a small pit in the hollow organ, by using a suture member that includes (a) multiple pairs of first and second arrow-shaped members having engaging parts that engage with tissue in the hollow organ, and (b) a suture thread that is attached by one of its ends (first end) to a rear end of the first arrow-shaped member and then is inserted into and pulled freely through a rear end of the second arrow-shaped member; with said surgical device comprising:

(1) multiple pairs of suture-member cartridges constituting a leading-end portion of the surgical device and having multiple pairs of tubes arranged alongside an outer surface of a leading-end portion of the endoscope, whereby the suture thread for each pair of arrow-shaped members is diverted around the leading ends of the corresponding pair of tubes or passed through small holes or slit-like openings provided in opposing side walls of the tubes and is fixed by an opposite end (second end) of the suture thread to the inner surface of the leading-end side of a tubular member that accommodates the second arrow-shaped member, with the arrow-shaped members, which are linked by the suture thread to form a pair, being respectively accommodated in the tubes;

(2) a feed-air switching mechanism coupled to the respective rear ends of the suture-member cartridges, for switching between a circulation state for supplying compressed air or high-pressure gas sequentially into each suture-member cartridge and a non-circulation state for blocking the compressed air or high-pressure gas;

(3) a hollow-organ-insertable unit that includes at least one flexible air tube that is coupled to a rear end of the feed-air switching mechanism and is arranged alongside an outer surface of a hollow-organ-insertable tube of the endoscope; and (4) a gas shooter that is coupled to a rear end of the hollow-organ-insertable unit outside the hollow organ, and that includes a cylinder unit that has either (a) a piston that, through its operation, generates compressed air, or (b) a high-pressure-gas reservoir that stores high-pressure gas; with said compressed air or high-pressure gas being released through an ejection hole in response to trigger operations of the gas shooter and sequentially ejected into the suture-member cartridges via the hollow-organ-insertable unit and the feed-air switching mechanism;

and the arrow-shaped members are sequentially ejected from the suture-member cartridge by compressed air or high-pressure gas sequentially ejected into the suture-member cartridge and are driven into tissue in the hollow organ on both sides of the small-pit site, with the rear ends of the arrow-shaped members drawn together via the suture thread linking those rear ends, so as to tightly suture the small-pit site.

24. A surgical system for small-pit closure in hollow organs according to claim 23, wherein the feed-air switching mechanism includes:

a generally cylindrical hollow case that is interposed between the hollow-organ-insertable unit and the suture-member cartridge or the gas shooter that has front and rear walls coupled to the hollow-organ-insertable unit and the suture-member cartridge or the gas shooter and that is fitted around the leading-end of an endoscope;

a rotary member rotatably accommodated in the case and having a switching plate formed adjacent to the front wall of the case; and a driving means for rotating the rotary member in association with a trigger operation on the gas shooter in order to switch sequentially the two positions for the circulation state achieved with an opening provided in the switching plate and a non-circulation state achieved through a shielding part constituting an area of the switching plate other than the opening.

25. A surgical system for small-pit closure in hollow organs according to claim 24, wherein the driving means includes the following, all of which are accommodated in the case:

a knock member fitted around a generally cylindrical body of the rotary member while freely moving forward and rearward and having a piston formed on a end of the knock member, with pressing teeth in a number (N) equal to the number of suture-member cartridges formed on a front end of the knock member;

protruding parts formed on the outer circumference of the cylindrical body that is connected to a switching plate of the rotary member;

a cam cylinder having N/2 each of both deep first-cam grooves and shallow second-cam grooves formed alternately on the inner surface of said cam cylinder at circumferential intervals (pitch angles) corresponding to placement of the suture-member cartridges for alternately engaging with the protruding members on the rotary member while being freely movable forward and rearward, and having a front-end face that contacts an inner surface on a front wall of the case; and a compression spring interposed between the cam cylinder and the piston, for constantly urging the piston toward a back side of the case;

and wherein said surgical system the driving means constitutes a gas-pressure rotary-knock mechanism in which compressed air or high-pressure gas ejected sequentially through the hollow-organ-insertable unit in response to trigger operations on the gas shooter pushes against the piston and advances the knock member while the pressing teeth follow along the cam grooves, and the rotary member rotates one pitch angle at a time when the pressing teeth contact and slide over the sloped surfaces formed on the end-faces of the protruding parts.

26. A surgical system having a surgical device for small-pit closure in hollow organs, with said surgical device being a suturing device mounted along an outer surface of an endoscope that is inserted into a hollow organ and that extends to a leading-end portion of the endoscope, so as to suture tissue at a site of a small pit in the hollow organ by using a suture member that includes (a) at least one pair of first and second arrow-shaped members having engaging parts that engage with tissue in the hollow organ, and (b) a suture thread whose two ends are respectively attached to the rear ends of the arrow-shaped members, with said surgical device comprising:

(1) at least one pair of suture-member cartridges constituting a leading-end portion of the surgical device and having at least one pair of tubular members and a narrow tube interposed between the pair of tubular members arranged alongside the outer surface of the leading-end portion of the endoscope, whereby the suture thread is diverted around leading ends of the tubular members or passed through small holes or slit-like openings provided in opposing side walls of the tubular members, with a middle portion of the suture thread inserted as a U-shaped loop through a threading member and accommodated in the narrow tube, with the arrow-shaped members, which are linked by the suture thread so as to form a pair, respectively accommodated in the tubular members;

(2) a hollow-organ-insertable unit that includes flexible air tubes that are coupled to a rear end of the suture-member cartridge;

(3) a gas shooter that is coupled to a rear end of the hollow-organ-insertable unit outside the hollow organ and that includes a cylinder unit having either (a) a piston that, through its operation, generates compressed air, or (b) a high-pressure-gas reservoir that stores high-pressure gas, whereby the compressed air or high-pressure gas is released through an ejection hole in response to trigger operations and is sequentially ejected into the suture-member cartridge via the hollow-organ-insertable unit; and (4) pulling means having (a) a flexible guide tube whose leading-end portion can be inserted into the narrow tube, and (b) a wire on the leading end of which is provided an engaging part for engaging the U-shaped middle portion of the suture thread in the narrow tube for pulling the middle portion of the suture thread by a rear-end portion of the wire outside the hollow organ in a direction away from the hollow organ;

and the arrow-shaped members are sequentially ejected from the suture-member cartridge by compressed air or high-pressure gas sequentially ejected into the suture-member cartridge and are driven into tissue in the hollow organ on both sides of the small-pit site, with the rear ends of the arrow-shaped members drawn together via the suture thread linking those rear ends, so as to tightly suture the small-pit site.

27. A surgical system for small-pit closure in hollow organs according to claim 26, wherein the pulling means further includes a wire-take-up means that is coupled to the guide tube on a rear end outside the hollow organ, is fixed to the rear end of the wire, and that, in response to a trigger operation, rotates in the direction for taking up the wire.

* * * * *